(12) United States Patent
Chi et al.

(10) Patent No.: US 10,227,592 B2
(45) Date of Patent: Mar. 12, 2019

(54) NUCLEIC ACID INDUCING RNA INTERFERENCE MODIFIED FOR PREVENTING OFF-TARGET, AND USE THEREOF

(71) Applicant: ENCODEGEN CO., LTD, Seoul (KR)

(72) Inventors: Sung Wook Chi, Seoul (KR); Eun-Sook Jang, Seoul (KR)

(73) Assignee: ENCODEGEN CO., LTD., Seoul (KR)

( * ) Notice: Subject to any disclaimer, the term of this patent is extended or adjusted under 35 U.S.C. 154(b) by 0 days.

(21) Appl. No.: 15/104,454

(22) PCT Filed: Dec. 8, 2014

(86) PCT No.: PCT/KR2014/011994
§ 371 (c)(1),
(2) Date: Jun. 14, 2016

(87) PCT Pub. No.: WO2015/093769
PCT Pub. Date: Jun. 25, 2015

(65) Prior Publication Data
US 2016/0304878 A1 Oct. 20, 2016

(30) Foreign Application Priority Data

Dec. 17, 2013 (KR) ........................ 10-2013-0157498
Dec. 4, 2014 (KR) ........................ 10-2014-0173038

(51) Int. Cl.
| | | |
|---|---|---|
| C12N 15/113 | (2010.01) | |
| A61K 31/712 | (2006.01) | |
| A61K 31/7115 | (2006.01) | |
| C12N 15/11 | (2006.01) | |

(52) U.S. Cl.
CPC ........ *C12N 15/1137* (2013.01); *C12N 15/111* (2013.01); *C12N 15/113* (2013.01); *C12N 2310/14* (2013.01); *C12N 2310/141* (2013.01); *C12N 2310/31* (2013.01); *C12N 2310/332* (2013.01); *C12N 2310/344* (2013.01); *C12N 2310/531* (2013.01); *C12N 2310/533* (2013.01); *C12N 2320/53* (2013.01)

(58) Field of Classification Search
None
See application file for complete search history.

(56) References Cited

U.S. PATENT DOCUMENTS

| | | | |
|---|---|---|---|
| 7,595,387 B2 | 9/2009 | Leake et al. | |
| 2007/0203084 A1* | 8/2007 | Weiler ................... | C12N 15/111 514/44 A |
| 2012/0142011 A1* | 6/2012 | Hahn ..................... | C12N 15/111 435/6.12 |

FOREIGN PATENT DOCUMENTS

| | | | |
|---|---|---|---|
| CN | 103140582 A | 6/2013 | |
| JP | 2007-531520 A | 11/2007 | |
| JP | 2011-500003 A | 1/2011 | |
| JP | 2013-511990 A | 4/2013 | |
| KR | 10-2011-0049733 A | 5/2011 | |
| WO | 2009/044392 A2 | 4/2009 | |
| WO | 2010/145778 A1 | 12/2010 | |
| WO | 2011/085056 A1 | 7/2011 | |

OTHER PUBLICATIONS

Cottonham et al (J. Biol. Chem. 285(46): 35293-35302, 2010).*
International Searching Authority, International Search Report of PCT/KR2014/011994 dated Mar. 13, 2015.
Aimee L Jackson et al., Expression profiling reveals off-target gene regulation by RNAi, Nature Biotechnology, Jun. 2003, vol. 21, No. 6.
Aimee L. Jackson et al., Widespread siRNA "off-target" transcript silencing mediated by seed region sequence complementarity, RNA, 2006, pp. 1179-1187, Cold Spring Harbor Laboratory Press.
Amanda Birmingham et al., 3' UTR seed matches, but not overall identity, are associated with RNAi off-targets, Nature Methods, Mar. 2006, pp. 199-204, vol. 3, No. 3.
Xiaoyu Lin et al., siRNA-mediated off-target gene silencing triggered by a 7 nt complementation, Nucleic Acids Research, 2005, pp. 4527-4535, vol. 33, No. 14.
Emily M. Anderson et al., Experimental validation of the importance of seed complement frequency to siRNA specificity, RNA, 2008, pp. 853-861, vol. 14, No. 5, Cold Spring Harbor Laboratory Press.
David P. Bartel, "MicroRNAs: Target Recognition and Regulatory Functions", Cell, Jan. 23, 2009, pp. 215-233, vol. 136, Elsevier Inc.
Nitin Puri et al., "LNA incorporated siRNAs exhibit lower off-target effects compared to 2'-OMethoxy in Cell Phenotypic Assays and Microarray Analysis", Nucleic Acids Symposium Series, Sep. 8, 2008, pp. 25-26, No. 52, Oxford University Press.
Jesper B. Bramsen et al., A screen of chemical modifications identifies position-specific modification by UNA to most potently reduce siRNA off-target effects, Nucleic Acids Research, 2010, pp. 5761-5773, vol. 38, No. 17.
Pooja Dua et al., "Modified siRNA Structure With a Single Nucleotide Bulge Overcomes Conventional siRNA-mediated Off-target Silencing", Molecular Therapy, Sep. 2011, pp. 1676-1687, vol. 19, No. 9.
Sung Wook Chi et al., An alternative mode of microRNA target recognition, Nat Struct Mol Biol., Jan. 10, 2013, pp. 321-327.

(Continued)

*Primary Examiner* — Richard A Schnizer
(74) *Attorney, Agent, or Firm* — Sughrue Mion, PLLC

(57) ABSTRACT

Provided is an RNA interference-inducing nucleic acid comprising at least one nucleic acid strand, the at least one nucleic acid strand comprising a modification substituted to a spacer, which is unable to form a base pair, in the 5' end or the 3' end region. The RNA interference-inducing nucleic acid is a modified form of nucleotide provided to prevent off-target effects, offering a method to selectively repress target gene expression. The RNA interference-inducing nucleic acid provides modified forms with target selectivity and specificity as a method to block the off-target effects while silencing the target gene expression, whereas the usage of conventional RNA interference-inducing nucleic acids cause inaccuracy and adverse effects through off-targets, thereby the RNA interference-inducing nucleic acid was offered to solve the problem, wherein it will be widely used as a method for repressing gene expression in research and for gene therapy without concerning the off-target effects.

16 Claims, 46 Drawing Sheets

Specification includes a Sequence Listing.

(56) References Cited

OTHER PUBLICATIONS

Nicole T. Schirle et al. "The crystal structure of human Argonaute2", Science, May 25, 2012, (6084), pp. 1037-1040, vol. 336.
Maria Frank-Kamenetsky et al., "Therapeutic RNAi targeting PCSK9 acutely lowers plasma cholesterol in rodents and LDL cholesterol in nonhuman primates", PNAS, Aug. 19, 2008, pp. 11915-11920, vol. 105, No. 33.
Christopher D Armour et al., "Digital transcriptome profiling using selective hexamer priming for cDNA synthesis", Nature Methods, Sep. 2009, pp. 647-649, vol. 6, No. 9.
Da Wei Huang et al., "Systematic and integrative analysis of large gene lists using DAVID bioinformatics resources", 2009, Nature Protocols, pp. 44-57, vol. 4, No. 1.
Rui Shi et al., "Facile means for quantifying microRNA expression by real-time PCR", BioTechniques, pp. 519-524, 2005, vol. 39, No. 4.
Korea Intellectual Property Office, Office Action of Korean Application No. 10-2014-0173038 dated Oct. 21, 2015.
Korea Intellectual Property Office, Office Action of Korean Application No. 10-2014-0173038 dated May 26, 2016.
Japanese Patent Office; Communication dated Jul. 11, 2017 in counterpart Japanese application No. 2016-541157.
European Patent Office; Communication dated Jun. 19, 2017 in counterpart European application No. 14872036.0.
Australian Patent Office; Communication dated Jun. 5, 2017 in counterpart Australian application No. 2014367550.
State Intellectual Property Office of People's Republic of China, Communication dated Oct. 15, 2018 in Counterpart Application No. 201480068785.4.

* cited by examiner

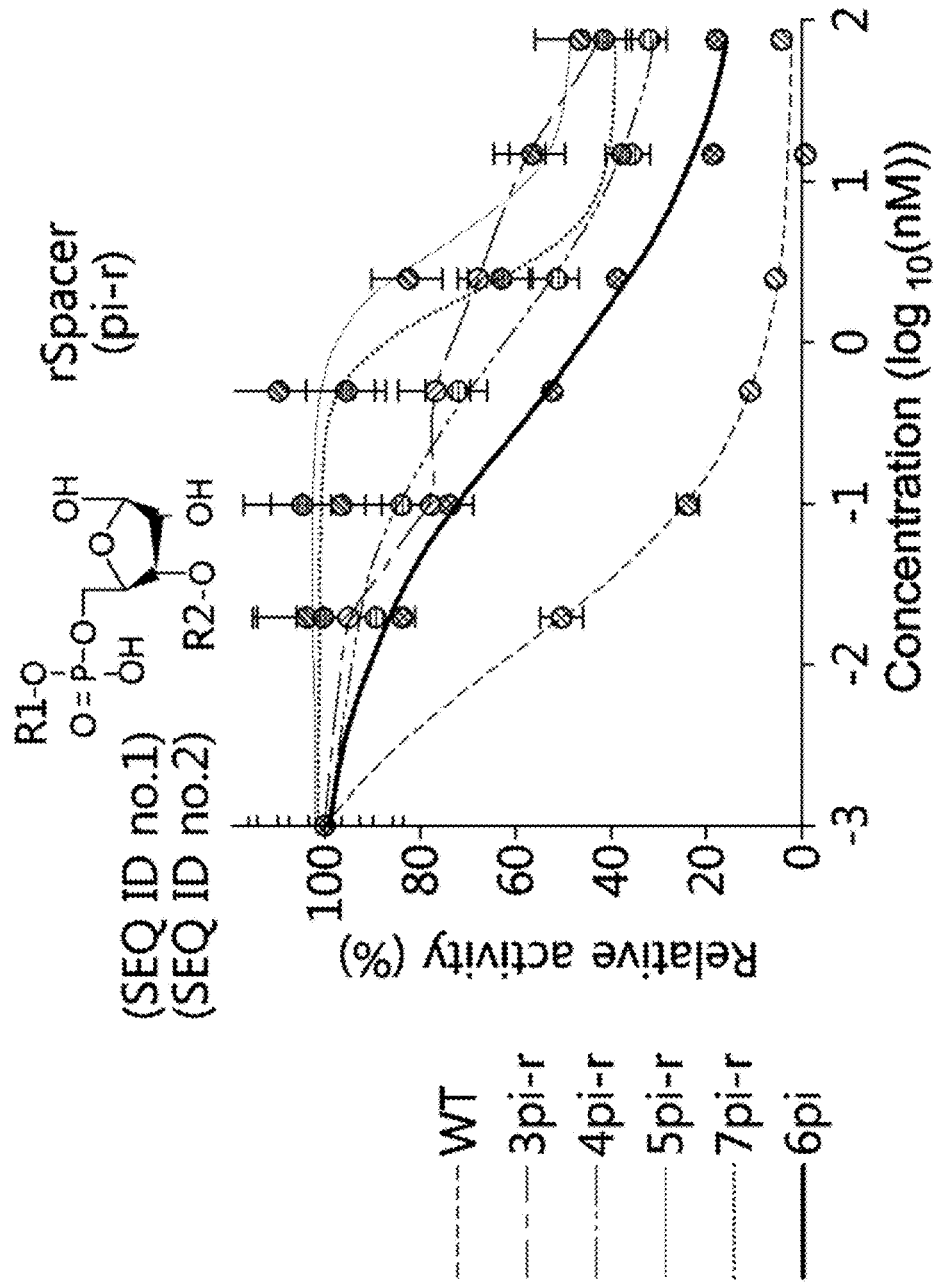

| siRL | IC$_{50}$(nM) | I$_{max}$(%) |
|---|---|---|
| WT | 0.01 | 100 |
| 2pi-r | 0.41 | 94 |
| 3pi-r | NA | 57 |
| 4pi-r | 0.99 | 68 |
| 5pi-r | 4.01 | 54 |
| 6pi-r | 3.17 | 70 |
| 7pi-r | 1.91 | 58 |
| 6pi | 0.41 | 78 |

(SEQ ID no.1)
(SEQ ID no.2)

(SEQ ID no.1)
(SEQ ID no.2)

| siRL | IC$_{50}$(nM) | I$_{max}$(%) |
|---|---|---|
| WT | 0.01 | 100 |
| 2pi-I | 0.18 | 93 |
| 3pi-I | 0.08 | 86 |
| 4pi-I | 3.06 | 34 |
| 5pi-I | N/D | 19 |
| 6pi-I | N/D | 48 |
| 7pi-I | N/D | 53 |
| 6pi | 0.41 | 78 |

(SEQ ID no.1)
(SEQ ID no.2)

(SEQ ID no.3,4)
(SEQ ID no.9)
(SEQ ID no.10)
Total cholesterol (SEQ ID no.3,4)
(SEQ ID no.9)
(SEQ ID no.10)
A2 6pi

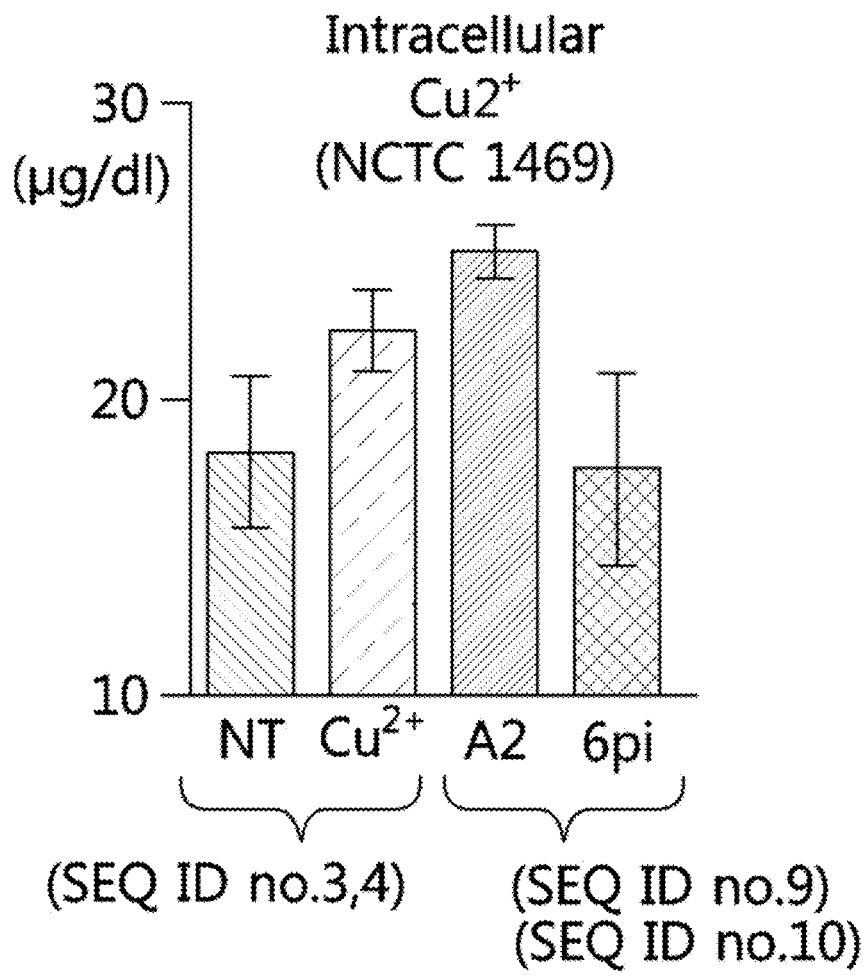

FIG. 11a
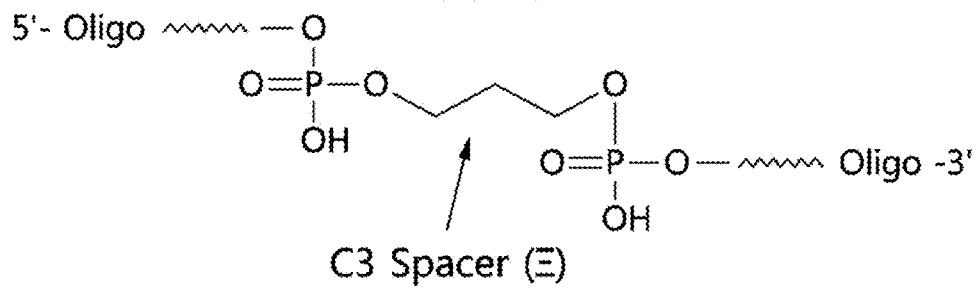
FIG. 11b
(SEQ ID no.11)
miR-124    5' –UAAGGCACGCGGUGAAUGCdTdT -3'
           3' – dTdTAUUCCGUGCGCCACUUACG -5'
(SEQ ID no.12)
miR-124-6c3    5' –UAAGGΞACGCGGUGAAUGCdTdT-3'
               3' – dTdTAUUCCGUGCGCCACUUACG -5'
FIG. 11c
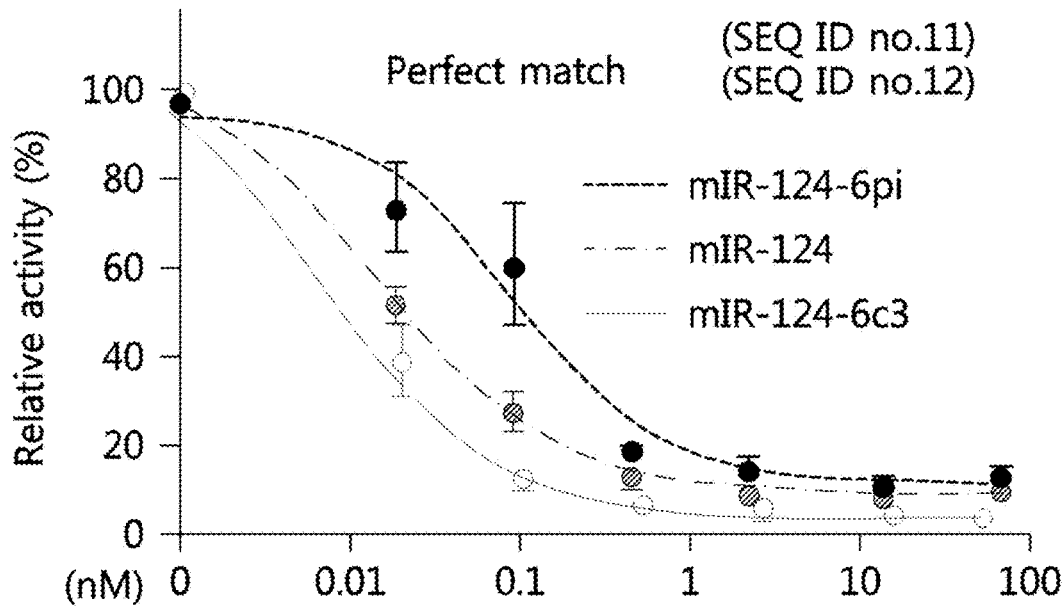

NUCLEIC ACID INDUCING RNA INTERFERENCE MODIFIED FOR PREVENTING OFF-TARGET, AND USE THEREOF

CROSS REFERENCE TO RELATED APPLICATIONS

This application is a National Stage of International Application No. PCT/KR2014/011994 filed Dec. 8, 2014, claiming priority based on Korean Patent Application Nos. 10-2013-0157498 filed Dec. 17, 2013 and 10-2014-0173038 filed Dec. 4, 2014, the contents of all of which are incorporated herein by reference in their entirety.

TECHNICAL FIELD

The present invention relates to an RNA interference-inducing nucleic acid and the use thereof, and more particularly to an RNA interference-inducing nucleic acid comprising at least one single strand of double strands, the at least one single strand comprising a modification substituted to a spacer in the 5' end and the 3' end region.

BACKGROUND ART

The siRNA (small interfering RNA) has been widely used as a method to repress expression of a desired target gene through RNA interference, but it also causes non-specific repression of other genes, off target effects, as an inevitable disadvantage, raising the serious concern of leading to faulty research results or side effects in therapeutic treatments. The off-target effects are occurred since Argonaute protein, the core effector in RNA interference, treats siRNA, which is artificially introduced in order to induce RNA interference, as a miRNA (microRNA) existing in a cell. Therefore, it is called miRNA-like off-target effect. The miRNA recognizes a target gene majorly through base-pairing with a seed region (positions 2-7 from the 5' end) for suppression, and the off-targets caused by siRNAs are also induced depending on sequences of the seed regions as well. The miRNA-like off-target effects in siRNAs have been already reported in several studies (Jackson, A. L., et al., Nat. Biotechnol., 21(6): 635, 2003; Jackson, A. L., et al., Rna, 12(7): 1179, 2006; Birmingham et al., Nat. Methods, 3(3): 199, 2006; Lin et al., Nucleic Acids Res., 33(14): 4527, 2005; Anderson et al., RNA, 14(5): 853, 2008), and affect expression of at least hundreds and at most ~1500 of genes depending on sequences of the seed regions and are serious enough to cause up to 30% of the positive hits in siRNA based phenotype screening. Additionally, in the case of miRNAs, they are also reported to silence target genes through compensatory pairings within their 3' end regions (3'-compensatory pairing) when the interactions between seed regions and targets become weak (Cell. 2009; 136:215-233), implicating that the miRNA-like off-target effects are likely to be mediated by such mechanism.

In addition, due to such widespread off-target silencing effects mediated by siRNAs, several chemical and structural modifications have been attempted to reduce the off-target silencing while maintaining the efficiency of suppressing an intended target. A modification adding methyl groups to a 2' position of a ribosyl ring of the nucleotide (2'OMe) was studied and used by Dharmacon Research (Lafayette, Colo.) to suppress the off-target effects, initially found to be effective in reducing both the number of off-targets and the extent of off-target effects especially when the 2'OMe is at a position 2 from the 5' end region, but the silencing of the intended target gene is also somewhat reduced. Since then, another kinds of modifications such as LNA modification (Puri et al., Nucleic Acids Symp. Ser 0.2008), UNA modification (Bramsen et al., Nucleic Acids Res. 2010; 38, 5761-73), and bulge modification introducing a single nucleotide bulge (Mol Ther. 2011 September; 19(9):1676-87) also have been developed.

However, all such chemical modifications were applied to a nucleotide backbone rather than to a base of which sequence is critical to cause off-targets, unable to affect a fundamental base-pairing. Because of this reason, they cannot completely block off-target effect albeit somewhat can be reduced, also having a problem to reduce efficiency of on-target silencing.

DISCLOSURE OF THE INVENTION

Technical Problem

Accordingly, the present inventors have developed modified RNA interference-inducing nucleic acids to overcome the problems of conventional methods, wherein the modified RNA interference-inducing nucleic acids can completely block the off-target effects while enhancing efficiency of repressing target gene, thereby have completed the present invention.

An object of the present invention is to provide an RNA interference-inducing nucleic acid comprising at least one single strand of double strands, the at least one single strand comprising a modification in which at least one of
    the sixth nucleotide from the 5' end, and
    each of the first and second nucleotides from the 3' end is substituted with a spacer.

Another object of the present invention is to provide a gene silencing composition comprising the RNA interference-inducing nucleic acid.

Another object of the present invention is to provide a gene silencing kit comprising the RNA interference-inducing nucleic acid.

Another object of the present invention is to provide a method for target gene silencing in a cell, the method comprising a step of introducing or expressing the RNA interference-inducing nucleic acid into the cell.

Another object of the present invention is to provide a method for suppressing off-target effects mediated by a guide strand or a passenger strand of the RNA interference-inducing nucleic acid, the method comprising a step of introducing or expressing the RNA interference-inducing nucleic acid into a cell.

However, the object of the present invention is not limited to the objects discussed above, and other objects which are not discussed above may be clearly understood from the following disclosures.

Technical Solution

To achieve the objects above, the present invention provides a RNA interference-inducing nucleic acid comprising at least one single strand of double strands, the at least one single strand comprising a modification in which at least one of the sixth nucleotide from the 5' end and each of the first and second nucleotides from the 3' end is substituted with a spacer.

In an embodiment of the present invention, the at least one single strand may bind to Argonaute protein in the same manner as ss-siRNA (single strand siRNA) which exists as a single strand and induces RNA interference.

In another embodiment of the present invention, the spacer may be a compound which affords to maintain the space of a nucleotide, preferably an organic compound, and more preferably a hydrogen carbon chain containing a phosphoryl group or a sulfuryl group, wherein the hydrogen carbon may be an alkyl group having 3 carbons (C3 Spacer).

In another embodiment of the present invention, the spacer may be one that cannot base-pair to any other physiological base, wherein the spacer may be an abasic deoxyribonucleotide (dSpacer) or an abasic ribonucleotide (rSpacer) as a backbone.

In another embodiment of the present invention, the RNA interference-inducing nucleic acid may further comprise a mismatch base pairing with an RNA of a target gene by a substitution or a bulge by an insertion.

In another embodiment of the present invention, the RNA interference-inducing nucleic acids may include any nucleotide inducing RNA interference such as siRNA, miRNA, shRNA, DsiRNA, IsiRNA, ss-siRNA, asiRNA, piRNA, and endo-siRNA.

In another embodiment of the present invention, as in miRNA (microRNA), in a case where a complementary target gene to a whole sequence of the RNA-interference-inducing nucleic acid is not existed in vivo, wherein the RNA-interference-inducing nucleic acid may have no function, and in such a case, the RNA interference-inducing nucleic acid may be provided as a control.

In another embodiment of the present invention, the target gene which the RNA interference-inducing nucleic acid is to repress can be of any genes, which can be a coding or non-coding gene mediated by RNA, transcribed in an organism including virus.

In another embodiment of the present invention, the RNA interference-inducing nucleic acid may be used for silencing target gene expression, and the double strand may be a product from artificial synthesis or a further processed product from in vivo modification.

The present invention provides a compound and/or a kit containing the RNA interference-inducing nucleic acid for silencing gene expression.

Additionally, the present invention provides a method for silencing target gene expression in a cell, the method comprising a step of introducing or expressing the RNA interference-inducing nucleic acid into the cell.

Furthermore, the present invention provides a method for suppressing off-target effects mediated by the guide strand or the passenger strand of the RNA interference-inducing nucleic acid, the method comprising a step of introducing the RNA interference-inducing nucleic acid.

Moreover, the present invention provides a method for suppressing off-target effects mediated by the guide strand or the passenger strand of the RNA interference-inducing nucleic acid, the method comprising a step of expressing the RNA interference-inducing nucleic acids in a cell.

Advantageous Effects

The present invention provides a RNA interference-inducing nucleic acid, wherein the RNA interference-inducing nucleic acid contains a novel modification to prevent the off-target effects caused by RNA interference for silencing target gene expression, thereby offering a method to selectively repress expression of a target gene.

DESCRIPTION OF DRAWINGS

FIGS. 3a, 3b, 3c, 3d and 3e show the effects of modified siRNAs with ribonucleotide spacer (rSpacer) substitution on gene silencing activity and miRNA-like off-target effects

FIGS. 8a, 8b, 8c, 8d, 8e and 8f show the results evaluating off-target effects in vivo with PCSK9 siRNAs containing the modification of the present invention, 6 pi.

FIGS. 11a, 11b, 11c, 11d, 11e, 11f, 11g, 11h, 11i and 11j show the results for siRNA of which position 6 from the 5' end is substituted to the spacer with an alkyl group (C3 spacer), wherein activity of repressing gene expression and miRNA-like off-target effects are evaluated.

MODE FOR INVENTION

Figure 1:
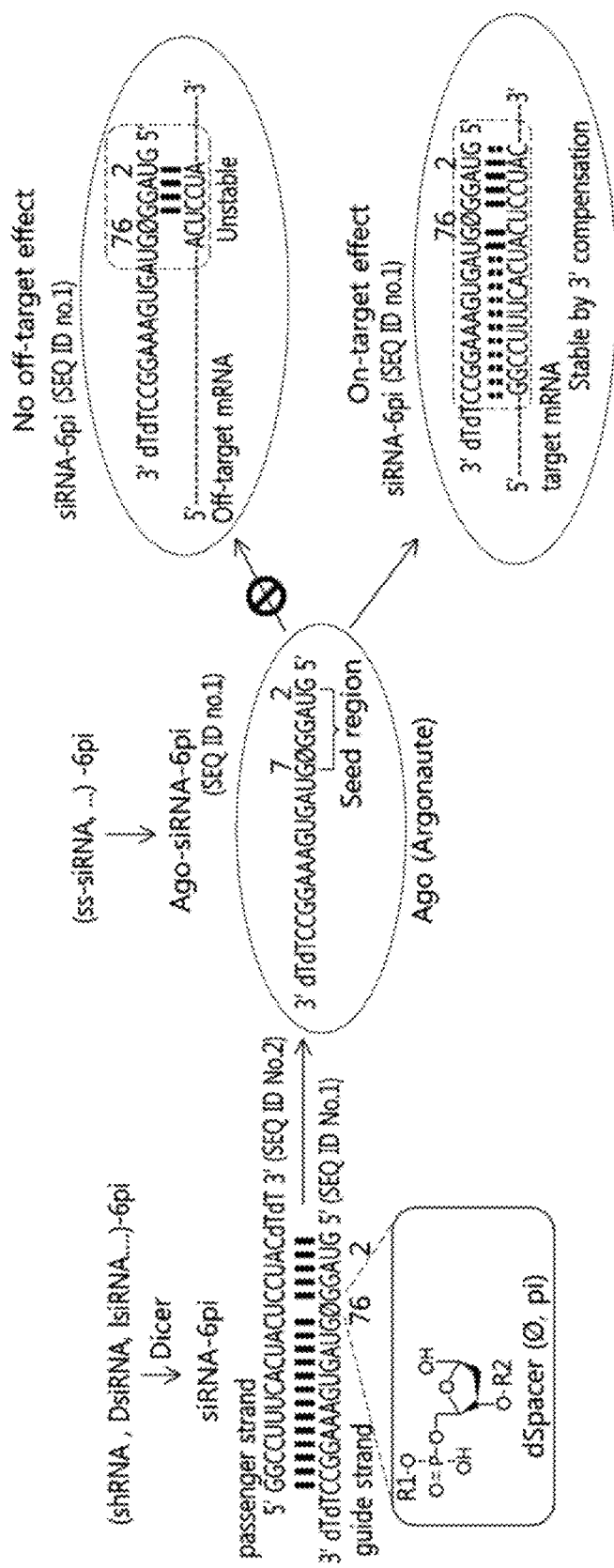
FIG. 1 is a diagram showing the activity of silencing on-target gene expression and suppressing miRNA-like off-target effects by deoxyribonucleotide spacer (dSpacer) modification.

The present invention is to provide an RNA interference-inducing nucleic acid comprising at least one single strand of double strands, the at least one single strand comprising a modification in which at least one of the sixth nucleotide from the 5' end and each of the first and second nucleotides from the 3' end is substituted with a spacer.

The present inventors have studied the RNA interference mediated by small RNAs to find a method to completely prevent the off-target effects while efficiently repress a target gene of interest, worked based on sequence specificity, wherein they validated as a result that a modification of the 5' end region of single strand from the RNA interference-inducing nucleic acid to a spacer, which contains covalent bonding with no base such as a single abasic nucleotide, showed a specific to block miRNA-like off-target effects and to efficiently repress the target gene, wherein a modification of the 3' end to contain the spacer, which is also the covalent bond with no base such as a single abasic nucleotide, also showed a specificity to block miRNA-like off-targets mediated by 3'-compensatory pairing but to effectively silence target gene, thereby completed the present invention.

In other words, in an embodiment of the present invention, the spacer modification in the position 6 from the 5' end eliminates off-targets while keeping the best efficiency of silencing the target gene. The transitional nucleation model (Nat Struct Mol Biol. 2012 Feb. 12; 19(3):321-7), elucidated by previous research of the present inventors, well accommodates these results, demonstrating that the position 6 from the 5' end, called "pivot", is a critical element to recognize miRNA-like off-targets.

In addition, expanding from using the abasic nucleotide, a nucleotide in position 6 is substituted to a spacer, wherein the spacer only has a form of covalent bonding between fifth and sixth nucleotide, thereby validated to perform the best efficiency in silencing target gene without causing off-target effects.

In other words, in examples of the present invention, the spacer modification in the position 6 from the 5' end completely block off-target effects, wherein a deoxyribonucleotide spacer (dSpacer) shows better performance in on-target activity where the dSpacer is relatively smaller than an rSpacer due to the absence of oxygen in 2' position, thereby the smallest spacer as an extreme case, alkyl spacer (C3 Spacer) was validated to perform on-target effect of which activity is similar to the activity of the unmodified form. Such superior on-target effect, shown by the small spacer located in position 6 from the 5' end, is well matched with the previous report of Ago-miRNA complex structure (Schirle et al, Science 2012, 336, 1037-40) and with the transitional nucleation model, in that, in order to silence targets, miRNA undergoes structural and functional changes after making base-pairing up to position 6 from the 5' end region.

In another embodiment of the present invention, the modification of the present invention was practically applied to miR-124, one of miRNAs functioning with seed-mediated target recognition, showing abrogation of miRNA-dependent target repression and lost in function inducing neuronal differentiation as a result, whereas a conventional 2'OMe modification, developed by Dharmacon company for reducing the off targets, was unable to block miR-124 function, induction of neuronal differentiation, wherein its effect on reducing off-targets is very modest compared with the present invention, confirmed by genome-wide examination of transcript expression.

In another embodiment of the present invention, the modification of the present invention was applied to siRNA for suppressing renilla luciferase or PCSK9 as a target gene and on-target and off-target effects were examined, wherein it is validated to show excellent performance in blocking off-target effects mediated by the guide strand and increased selectivity to the target. Especially, in the case of the application for PCSK9 siRNA, which is for reducing plasma cholesterol level, its therapeutic effect is validated to cause effective reduction of cholesterol level in mouse animal model as much as in the unmodified siRNA.

In another embodiment of the present invention, the off-target effects of PCSK9 siRNA was found to cause adverse side effects, in that it induces cell cycle stop in human liver cell, HepG2, and cell death in mouse liver tissue caused by the defect in copper metabolism, whereas such adverse side effects mediated by off-targets was shown to be eliminated in siRNA with the modification of the present invention, observed as a result of examining the side and off-target effects, thereby confirming the elimination of both the adverse side effects and the off-target effects and also the conservation of effective silencing activity to an intended target, PCSK9.

In another embodiment of the present invention, introduction of a mismatch in seed region, a conventional method proposed to reduce miRNA-like off-targets, was applied to position 6 from the 5' end of miR-124, one of miRNAs recognizing and repressing target genes through the mode of seed pairing, showing reduction of off-target effects in the validation, whereas the sequence change introduced by the mismatch responded to new matches to the altered seed, still recognizing and silencing new targets showing adverse side effects, wherein the same observation of showing the side effects was also confirmed even in the case of introducing 2'OMe modification to position 6 from the 5' end, wherein the 2'OMe modification is a conventional method for reducing off-targets.

In another embodiment of the present invention, it was validated that all conventional modification methods for suppressing off-target effects are unable to completely block off-target effects, but the present invention can completely abrogate off-target effects, wherein the conventional modification methods were 2'OMe modification in position 2 from the 5' end, UNA modification in position 7 from the 5' end, and introduction of one single nucleotide bulge in position 2 from the 5' end of double-stranded si RNA.

In another embodiment of the present invention, it is validated that spacer substitution of sixth nucleotide from the 5' end, mediating the covalent bonding between fifth and seventh nucleotide, completely abrogates off-target effects while keeping silencing of a target gene.

In another embodiment of the present invention, complete abrogation of miRNA-like off-targets mediated by 3' end compensatory pairing was observed along with superior silencing activity for gene expression, when first and second nucleotides from the 3' end were substituted to abasic spacers.

As stated above, the present invention may provide the RNA interference-inducing nucleic acid to silence target gene, wherein at least one strand from the double-stranded RNA interference-inducing nucleic acid contains a spacer substituted for a nucleotide in position 6 from the 5' end, where nucleotides in position 5 and 7 have covalent bonding with the spacer, or contains abasic nucleotides or spacers substituted for nucleotides in positions 1-2 from the 3' end.

In the disclosure above, the RNA interference-inducing nucleic acid prefers to form double strand, comprising of ~18-23 nucleotide-long guide strand and the passenger strand complementary to the corresponding guide strand, wherein the most appropriated form is 21 nucleotides, but not limited to this. Herein, the double strand can be derived from a stem-loop hairpin structure, of which stem part is processed to the double strand by Dicer protein, wherein the double strand is siRNA processed from shRNA, varied depending on strictures of nucleotides, thus not limited to only these cases. In addition, to achieve optimal suppression of off-target effects, it can include two abasic nucleotides in 3' end overhang, mismatch base-pairing to RNA of target gene by the substitution, or bulge formation by the insertion. The term 'bulge' refers to a portion in a double-stranded nucleotide, which is not paired and is gaped open due to the introduction of one or more nucleotides, and 'mismatch pair' generally refers to base pair which cannot make Watson-Crick base pairing.

In the present invention, the phrase 'guide strand' (antisense strand) refers to the single strand, which is a part of said double strand, determined to have sequence for silencing a target, wherein the guide strand majorly loads onto the Argonaute protein, plays role in guiding Argonaute complex to recognize target gene, and is a polynucleotide that is substantially or 100% complementary to mRNA of target gene of interest, thereby it is also called "antisense strand", wherein the guide strand can be the complementary polynucleotide as a whole or in part to siRNA, miRNA, shRNA, DsiRNA, IsiRNA. ss-siRNA, piRNA, endo-siRNA or asiRNA as examples, whereas the phrase 'passenger strand' refers to the strand, which forms said doublex structure with the guide strand, wherein it plays role as passenger in helping guide strand to load onto Argonaute protein, wherein it is a polynucleotide that is substantially or 100% the same sequence with target nucleic acids, thereby it is also called "sense strand", wherein the passenger strand can be the same polynucleotide as a whole or in part with siRNA, miRNA, shRNA, DsiRNA, IsiRNA, ss-siRNA, piRNA, endo-siRNA or asiRNA as examples.

In the present invention, the term 'spacer' refers to the substituent which can be the replacement of one single nucleotide and affordable to maintain single nucleotide space, not limited to the specific one but allowing anything maintaining the space, wherein the spacer prefers an organic compound, more appropriately hydrogen carbon chains containing (connected to) phosphoryl group (—$H_2PO_4$) or sulfuryl group (—$H_2PSO_4$), wherein the most appropriate one for the spacer is an alkyl group comprising at least three carbons. Additionally, the spacer includes abasic nucleotide forms such as dSpacer and rSpacer, representing single nucleotide derivatives containing no base at all, wherein the spacer also comprehensively refers any compound with modified base which cannot pair to any base including RNA present in vivo.

In the statement above, the single strand derived from the double strand has ability to bind Argonaute protein inducing RNA interference.

In the statement above, the RNA interference-inducing nucleic acid can contain spacer substitution modifications both in sixth nucleotide from the 5' end and in first and second nucleotides from the 3' end.

In addition, the present invention can provide composition and/or kit for gene silencing, including the RNA interference-inducing nucleic acid.

In the present invention, said 'composition' refers the compound which can be used for silencing expression of a target gene while suppressing off-target effects at the same time.

Herein, said 'kit' consists of the RNA interference-inducing nucleic acids for suppressing target gene expression and containers with such nucleotide components inducing RNA interference, wherein the container may take the form of bottles, tubs, sachets, envelops, tubes, ampoules, and the like, which may be formed in part or in whole from plastic, glass, paper, foil, wax, and the like. The container may be equipped with a fully or partially detachable lid that may initially be part of the container or may be affixed to the container by mechanical, adhesive, or other means, wherein the container may also be equipped with a stopper, allowing access to the contents by a syringe needle. The kit may comprise an exterior package which may include instructions regarding the use of the components.

Additionally, according to the present invention, the RNA interference-inducing nucleic acid effectively represses expression of a target gene, validated by the examples of the present invention, thereby providing a method for silencing expression of the target gene into a cell, wherein the method comprises a step of introducing the RNA interference-inducing nucleic acid into the cell, wherein also providing a method for silencing expression of the target gene into a cell, wherein the method comprises a step of expressing the RNA interference-inducing nucleic acid into the cell.

In the present invention, the target gene can be either endogenous gene or transgene, but not limited thereto.

Moreover, according to the present invention, the RNA interference-inducing nucleic acid effectively suppresses expression of a target gene while blocking off-target effects, validated by the examples, wherein the present invention is a method to inhibit off-target effect mediated either by the guide strand or the passenger strand of the RNA interference-inducing nucleic acids, wherein providing the method comprising a step of introducing the RNA interference-inducing nucleic acid into the cell. In addition, the present invention can provide a method comprising a step of expressing the RNA interference-inducing nucleic acid to abrogate off-target effects mediated by either the guide strand or the passenger strand of the RNA interference-inducing nucleic acids.

In the present invention, the phrase 'off-target effect' refers to a instance in which the guide strand of siRNA causes unexpected degradation of other mRNAs or silencing of gene expression of corresponding mRNAs, also including any instance in which the passenger strand of siRNA causes degradation of other mRNAs or silencing of gene expression of corresponding mRNAs by pairing to wrong targets, despite of the fact that siRNA is originally used only for degrading mRNA having a sequence complementary to the guide strand, thereby inhibiting the gene expression of the corresponding mRNA.

Hereinafter, examples will be provided in order to help to understand the invention. However, such examples are provided for illustrative purposes only, and the present invention is not limited thereto.

[Example 1] Comparison of Target Gene Silencing and Off-Target Effect Caused by siRNA Molecules with Deoxynucleotide Spacer (dSpacer) Substitution As examples illustrated in FIG. 1, the present inventors speculated that application of the spacer modification to the 5' end region of the RNA interference-inducing nucleic acids might be able to completely block off-target effects, while enhancing the repression of a target gene (on-target effects), wherein the spacer cannot make base-paring and the RNA interference-inducing nucleic acids includes all RNAs binding Argonaute protein, wherein the present inventors focused on the 5' end region, especially on the sixth nucleotide from the 5' end, called 'pivot', which is based on the mode of miRNA target recognition, transitional nucleation model (Nat Struct Mol Biol. 2012 Feb. 12; 19(3):321-7), thereby have invented the present RNA interference-inducing nucleic acids.

Initially, following experiments have been performed to compare the on-target and the off-target effects between modified si RNAs from the present invention and unmodified siRNAs that conventionally used. First, a guide strand RNA was synthesized where a nucleotide in the 5' end region (positions 1-11) including the seed region was substituted to deoxyribonucleotide spacer (dSpacer) (pi), and used to produce a double strand, which has two dT (deoxythymine nucleotide) overhangs with conventional 19 nucleotides structure via perfect reverse complementary to passenger strand, wherein the passenger strand was synthesized without any modification. Such RNA molecules were chemically synthesized by ST Pharma, Trilink Technologies or Bioneer company, further purified by HPLC, then a duplex between the guide strand and the passenger strand was produced as illustrated in left panel of FIG. 1 (e.g. abasic nucleotide substitution at position 6 from the 5' end, 6 pi) by following the protocol provided by the companies. While doing this, a control (NT; non-targeting, SEQ ID NOS: 3 and 4) was synthesized by using siRNA form of cel-miR-67, a microRNA (miRNA) expressed only in *C. elegans*.

The modification stated above was applied to siRNA (siRL, SEQ ID NO: 1) designed to silence *renilla* luciferase (*renilla* luciferase is derived from the insert of psi-check2 vector, Promega company). In detail, 75 nM siRNAs produced as the duplex above (SEQ ID NOS: 1 and 2) were co-transfected into HeLa cells (ATCC CCL-2) together with psi-check2 vectors, which express *renilla* luciferase, by using lipofectamine 2000 reagent (Invitrogen) according to manufacturer's protocol, then the effects were examined. In the case of measuring siRL mediated on-target effects, psi-check2 vector was used as intact, whereas in the case of measuring the off-target effects, *renilla* luciferase gene in psi-check2 vector was replaced by *renilla* luciferase in pRL-TK (promega) that was unable to respond to the on-target effects, then to construct RL-Seed and RL-Nuc, the vector included two copies of perfect complement sequences to seed region (positions 1-8 from the 5' end) of siRL (seed sites; Seed) and nucleation bulge sites which can bind to miRNA by forming bulge between positions 5 and 6, synthesized as DNA and inserted repetitively into 3'UTR (3' untranslated region). Herein, HeLa cell was cultured in Dulbecco's modified Eagle's medium (Invitrogen), supplemented with 10% FBS (fetal bovine serum), 100 U/ml penicillin, and 100 µg/ml streptomycin, whereas the transfection was performed in complete medium without antibiotics. After 24 hours from the transfection, effects of siRNA were examined by measuring luciferase activity using Dual-luciferase reporter assay system from Promega company according to manufacturer's protocol, wherein the *renilla* luciferase activity was estimated at least three times in replicates, measured by using Glomax Luminometer from Promega company, then normalized by firefly luciferase activity.

Figure 2A:
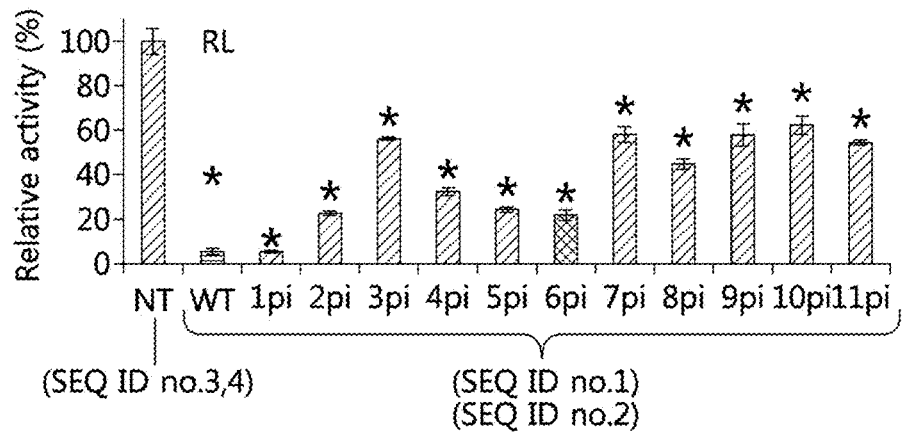
FIGS. 2a, 2b, 2c, 2d, 2e, 2f, and 2g show the effects of modified siRNAs with deoxyribonucleotide spacer (dSpacer) substitution on gene silencing activity and miRNA-like off-target effects.
Figure 2B:
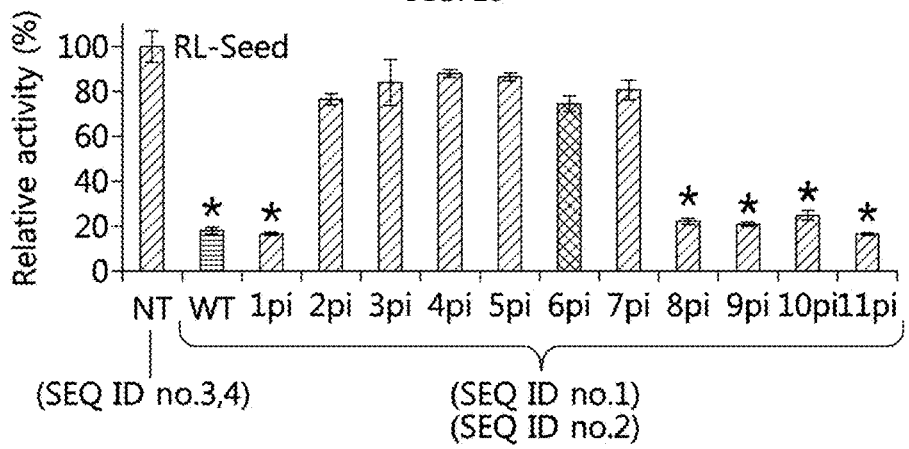
Figure 2C:
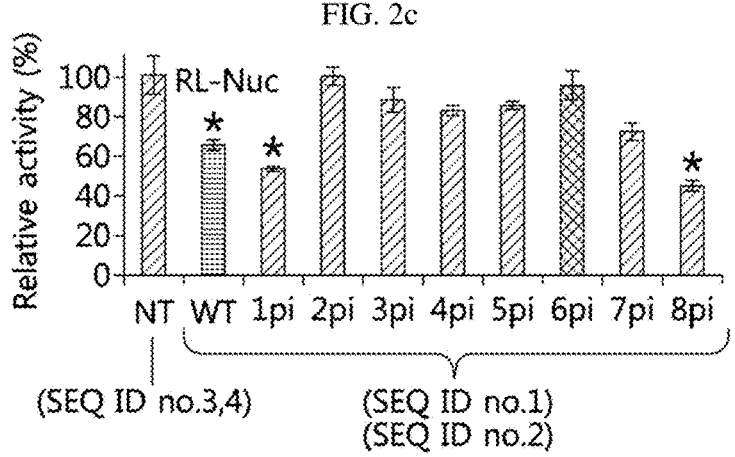

As a result, as shown in FIG. 2a, siRNA having a dSpacer substitution between position 1 and 11 from the 5' end region shows less than or equal to 60% of the activity (relative to the normalized value denominated by firefly luciferase), where the on-target effects were measured at 75 nM. Especially, although the substitution of position 2, 4, 5, or 6 reduced less than or equal to 30% of the activity, where the performance is not as much as the unmodified, the effect was still significant. However, when the miRNA-like off-target effects were estimated by using luciferase reporters where previously well-known sites such as seed sites (RL-Seed) or nucleation bulge sites (RL-Nuc) were inserted, the off-target repression was shown to be eliminated only in the case of the dSpacer substitution between positions 2 and 7, as represented in FIGS. 2b and 2c.

From the above, the dSpacer substitution between positions 2-7 from the 5' end turned out to eliminate the miRNA-like off-target effects while showing the on-target activity, wherein the abasic deoxynucleotide is a modification that cannot make base-pairing.

Figures 2D, 2E:
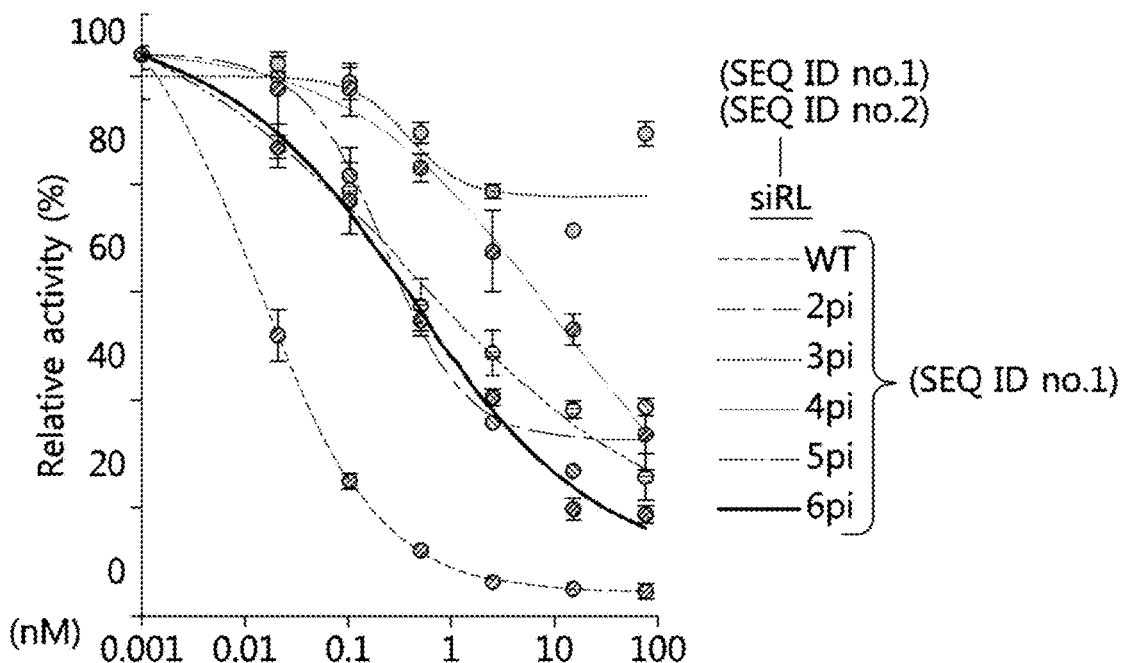

Furthermore, in order to investigate the superior on-target activity shown by the dSpacer substitution between positions 2-7 of the siRNA in detail, the on-target silencing activity was estimated across various concentrations to measure IC50 (inhibitory concentration 50) as a result, thereby validated that the substitution in position 5 or 6 is the most efficient, as represented in FIGS. 2d and 2e, wherein the substitution in position 6 especially performed the most excellent maximal inhibition rate (Imax) among the modifications that showed elimination of the off-target effects.

Figure 2F:
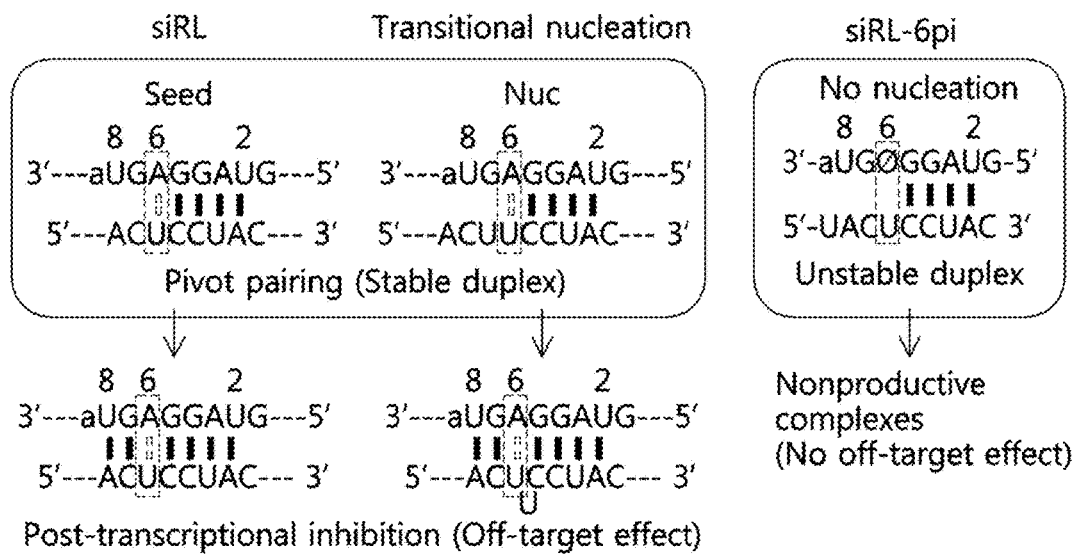

The above results well fit into the transitional nucleation model, a new mode of miRNA target recognition, as illustrated in FIG. 2f, wherein the results also match with the previous research reporting that a base-pairing in position 6 from the 5' end, especially called "pivot", is critical to recognize miRNA targets (Nat Struct Mol Biol. 2012 Feb. 12; 19(3):321-7).

Figure 2G:
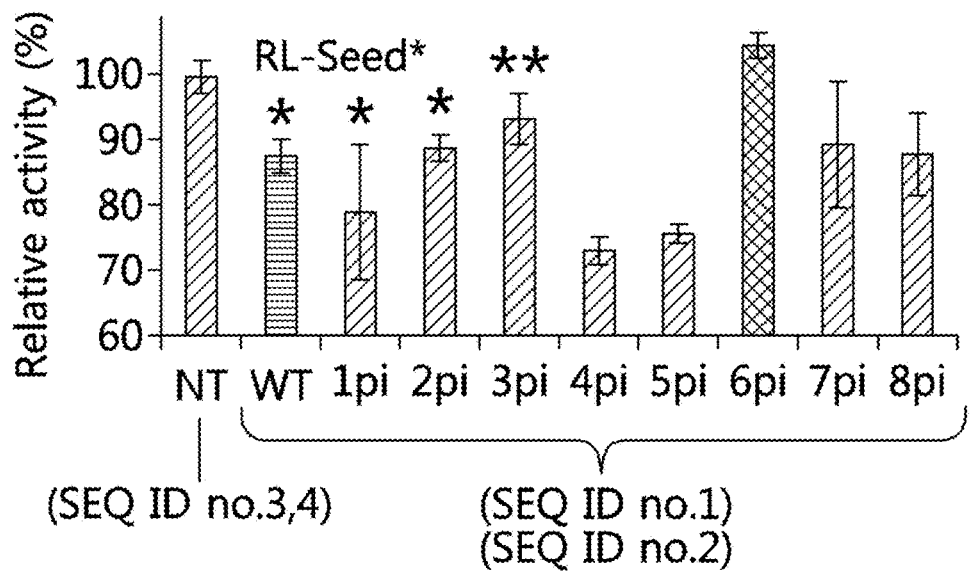

In addition, as shown in FIG. 2g, the guide strand having the single abasic deoxynucleotide substitution in position 3 or 6 from the 5' end reduced miRNA-like off-target effects mediated by the passenger strand in opposite, wherein the complete prevention can be achieved by the same modification on passenger strand, substituting a nucleotide in positions 2-7 from the 5' end region.

Based on the above, it was confirmed that the guide strand of the siRNA molecule should be appropriately used by substituting positions 2-7 from the 5' end to deoxyribonucleotide spacer (dSpacer) having defect in base-pairing, wherein the most appropriate usage is to substitute position 6 to dSpacer (6 pi), considering the effect on target gene repression and off-target avoidance.

[Example 2] Comparison of Target Gene Repression and Off-Target Effect Caused by siRNA Molecules with Ribonucleotide Spacer (rSpacer) Substitution In order to see whether the results in the example 1 above can be reproduced by a similar spacer having ribonucleotide backbone, a nucleotide in positions 2-7 of the siRL (SEQ NO: 1) was substituted to ribonucleotide spacer (rSpacer) (pi-r) where they showed elimination of off-targets before, wherein the on-target activity of the siRL was examined by calculating IC50 using the same method performed in the Example 1 above.

Figure 3B:
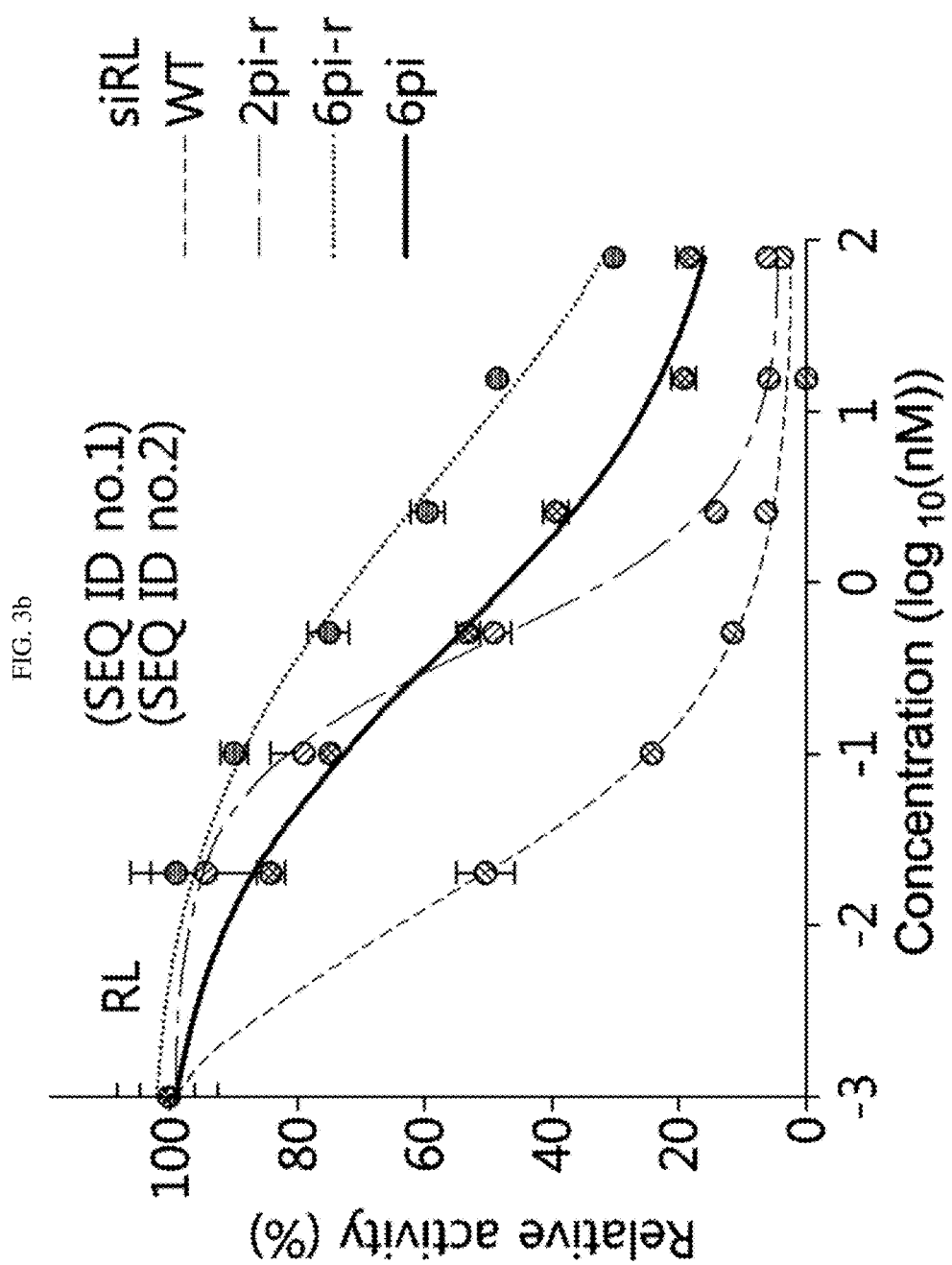
Figures 3C, 3D:
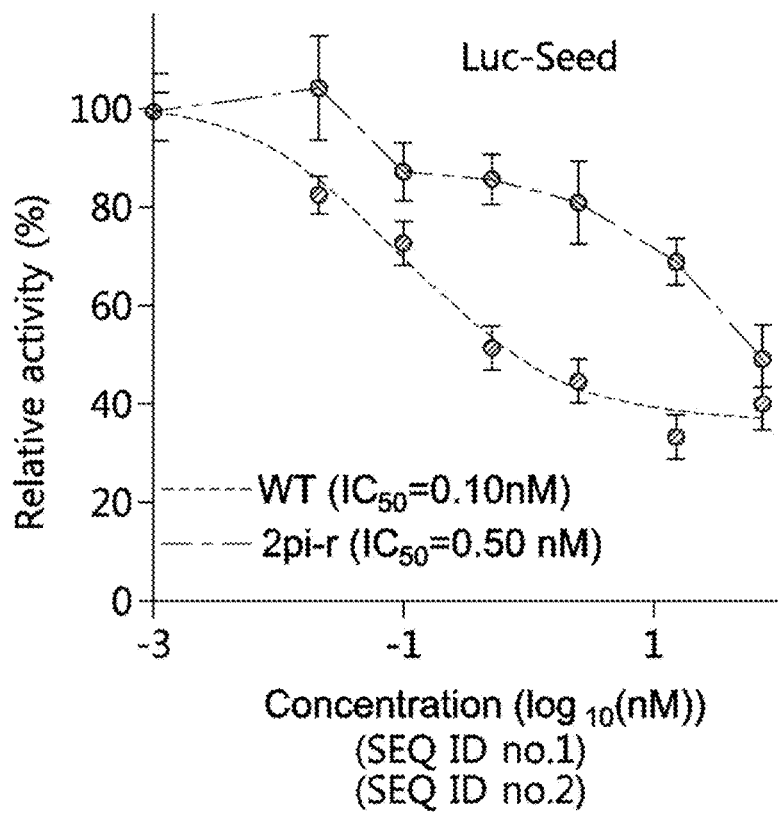
Figure 3E:
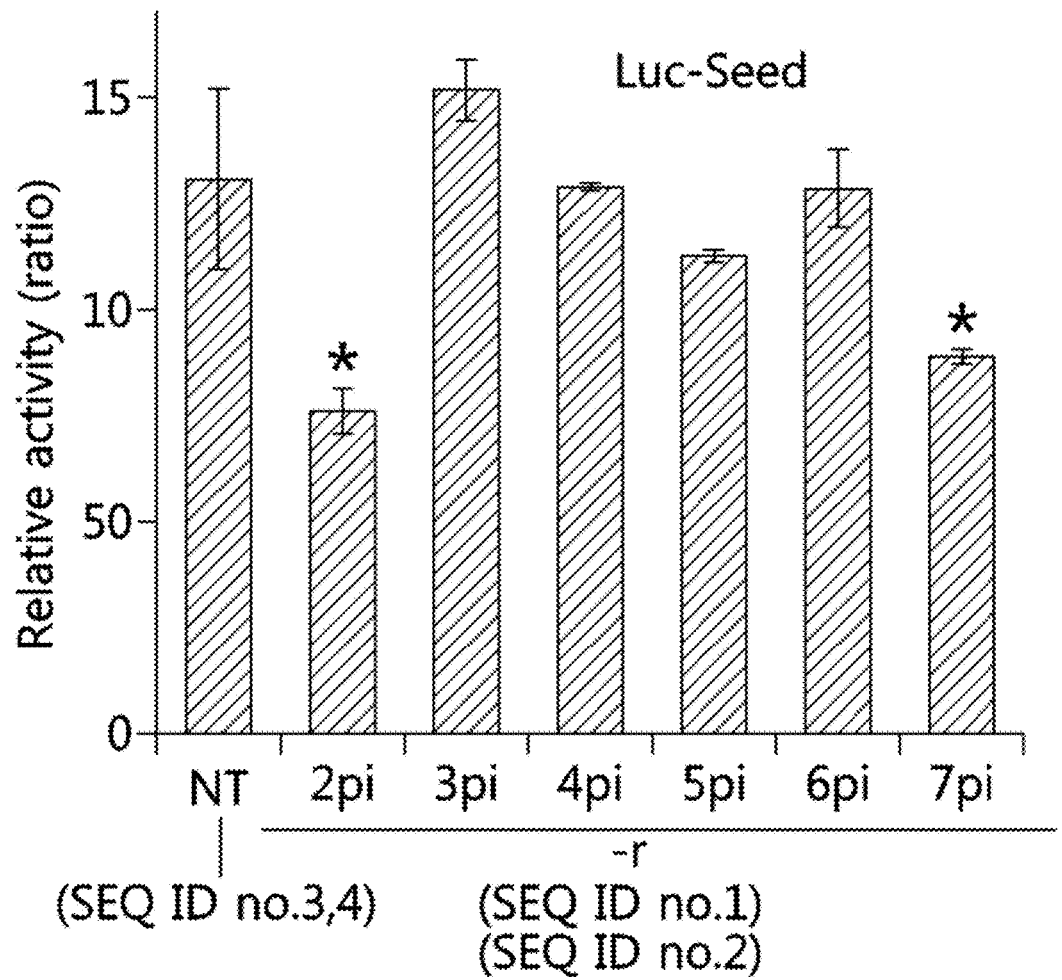

As a result, as shown in FIGS. 3a, 3b and 3c, every rSpacer substitution in position 2-7 from the 5' end showed more than or equal to 54% of maximal inhibitory rate (Imax) relative to the unmodified (WT) Among them, every modification except 2 pi-r (applied to position 2) has less on-target silencing activity than 6 pi. Exceptionally, the 2 pi-r showed superior on-target repression comparing with 6 pi, but still repressed off-targets as shown in FIG. 3d, where validated by measuring off-target effects with RL-seed according to the method in the example 1. Furthermore, when off-target effects for each modification were measured at 75 nM siRNA, it was confirmed that every modification except 2 pi-r and 7 pi-r blocks off-target effects (FIG. 3e).

Based on the above, it was confirmed that the guide strand of the siRNA molecule should be appropriately used by substituting position 3 or 6 from the 5' end to ribonucleotide spacer (rSpacer), wherein the most appropriate usage is to substitute position 6 to dSpacer (6 pi) as in Example 1 above, considering the effect on target gene repression and off-target avoidance.

Figures 4A, 4B:
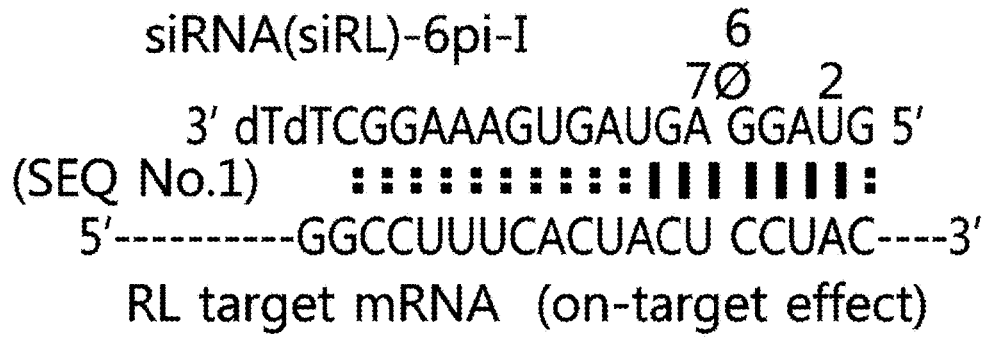
FIGS. 4a, 4b, 4c, 4d, 4e and 4f show the effects of modified siRNAs with deoxyribonucleotide spacer (dSpacer) insertion on gene silencing activity and miRNA-like off-target effects.

[Example 3] Comparison of Target Gene Silencing and Off-Target Effect Caused by siRNA Molecules with Deoxyribonucleotide Spacer (dSpacer) Insertion As sequence configuration containing deoxyribonucleotide spacer (dSpacer) in seed region, a mismatch pairing should be occurred in the part of an abasic in siRNA when it interacts with target gene RNA, wherein the abasic is made by substitution as in Example 1 and Example 2. Therefore, additionally the abasic can form a bulge when a dSpacer is inserted into the seed region of siRNA, as shown in FIG. 4a. As such, for the case of such dSpacer insertion, there changes in on-target and off-target effect were investigated. Initially, the on-target effects of siRL (SEQ NO: 1) were examined by measuring IC50 as in the method performed in example 1, wherein the siRL contains dSpacer insertion between positions 2-7 from the 5' end, wherein the positions 2-7 was reported to abolish off-target in the examples above.

Figure 4C:
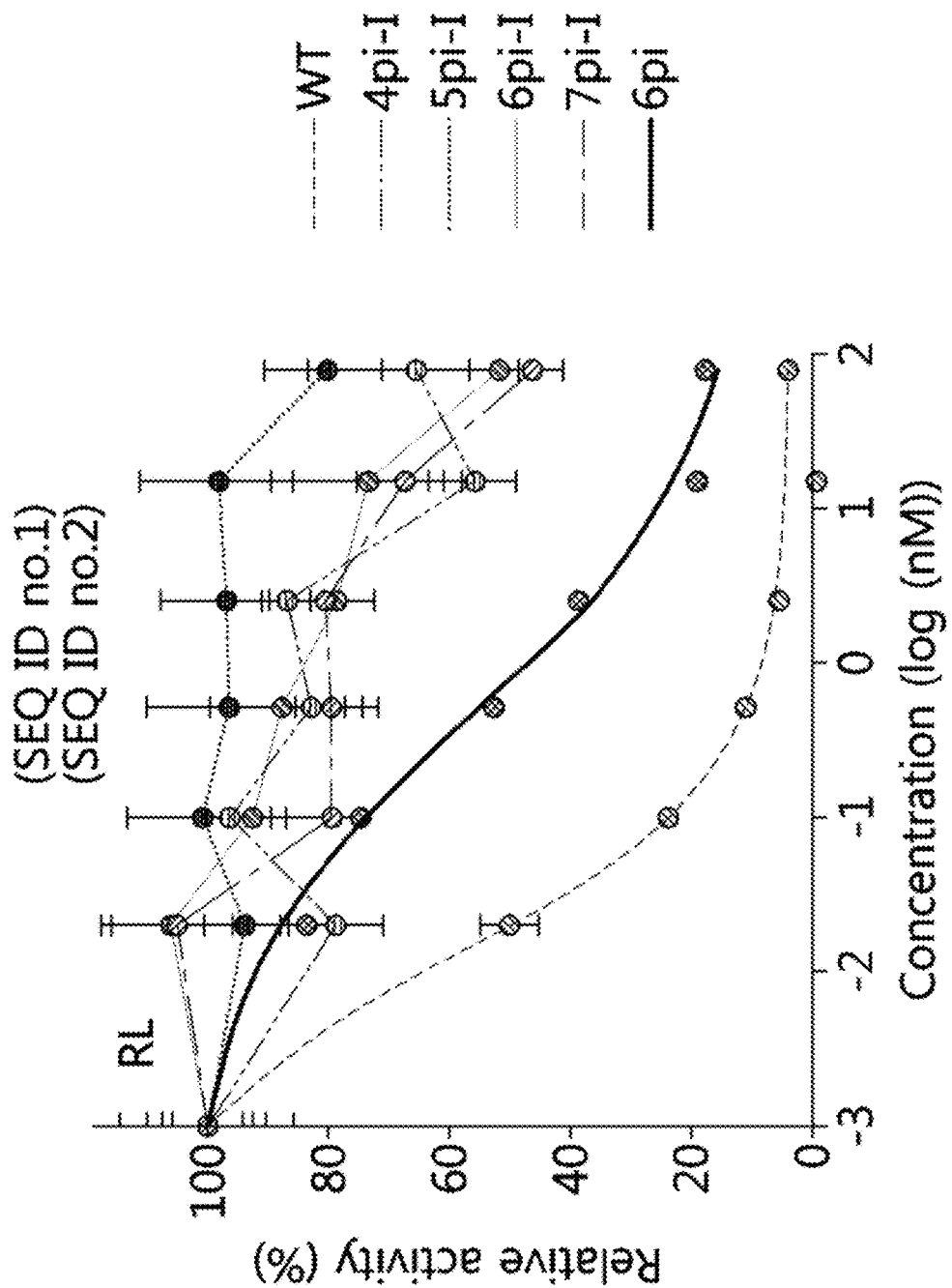
Figure 4D:
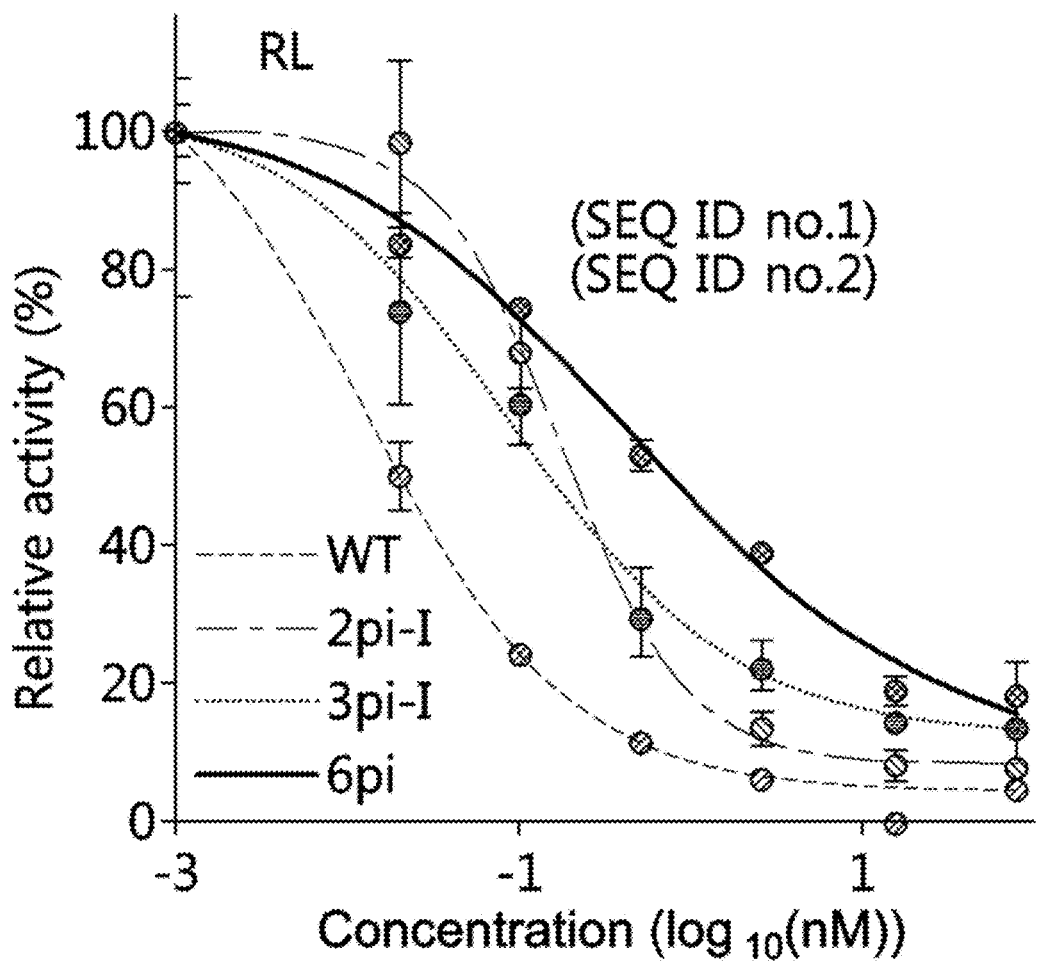
Figure 4E:
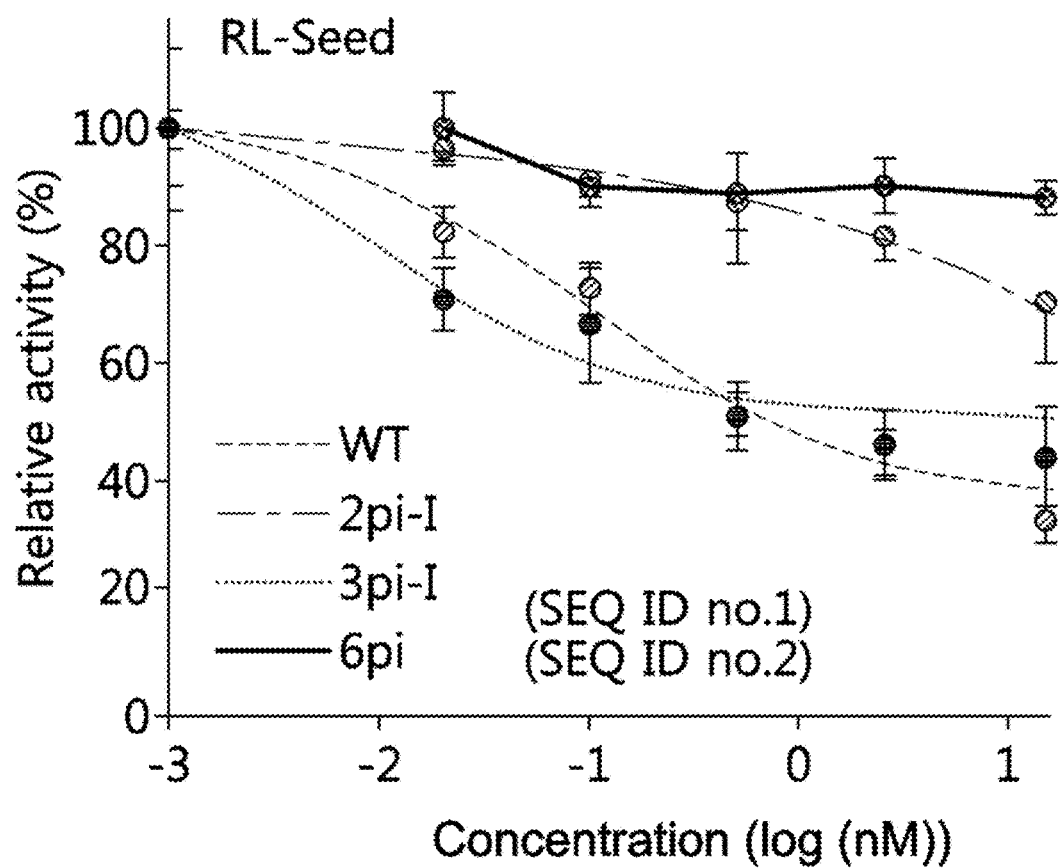
Figure 4F:
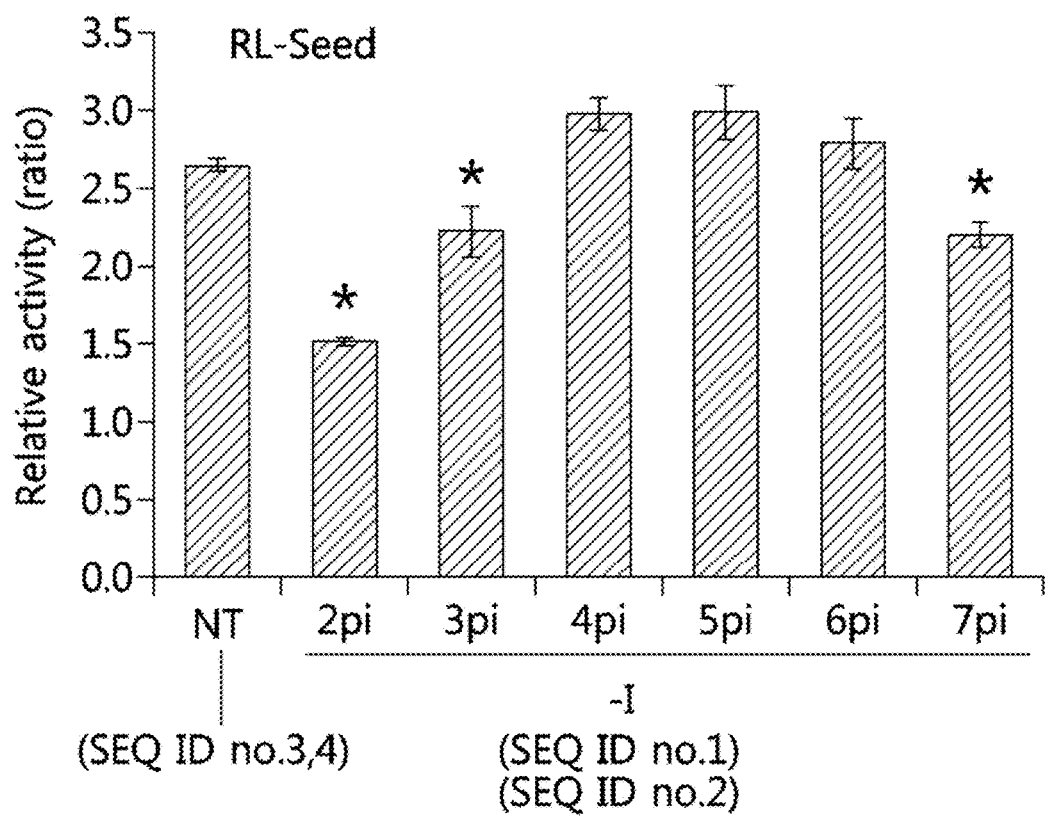

As a result, as shown in FIG. 4b, every dSpacer insertion between positions 2-7 from the 5' end showed at least 19% of maximal inhibitory rate, relative to the unmodified (WT). Additionally, as shown in FIGS. 4c and 4d, everything except 2 pi-I and 3 pi-I showed less potent on-target activity than 6 pi. Exceptionally, 2 pi-I and 3 pi-I showed better on-target activity than 6 pi, but they still silence off-targets (FIG. 4e), confirmed by the results from measuring off-target effect using RL-seed as performed in Example 1. Furthermore, as shown in FIG. 4f, all modifications (4 pi-I, 5 pi-I, 6 pi-I) except 2 pi-I, 3 pi-I and 7 pi-I abrogated off-target effects, observed at 75 nM siRNA concentration by measuring off-target effects for each modification.

In view of the above, it was confirmed that the guide strand of the siRNA molecule should be appropriately used by inserting deoxyribonucleotide spacer (dSpacer) into position 4 or 6 from the 5' end region, wherein the most appropriate usage is to substitute position 6 to dSpacer (6 pi) as in the example 1 above, considering the effect on target gene repression (on-target) and off-target avoidance.

[Example 4] Comparison of Target Gene Silencing and Off-Target Effect Caused by siRNA Molecules with Ribonucleotide Spacer (rSpacer) Insertion In order to investigate effect of ribonucleotide spacer (rSpacer) insertion into seed region (pi-rI) on the off-target effects, IC50 was measured by using the method in Example 3 above.

Figure 5A:
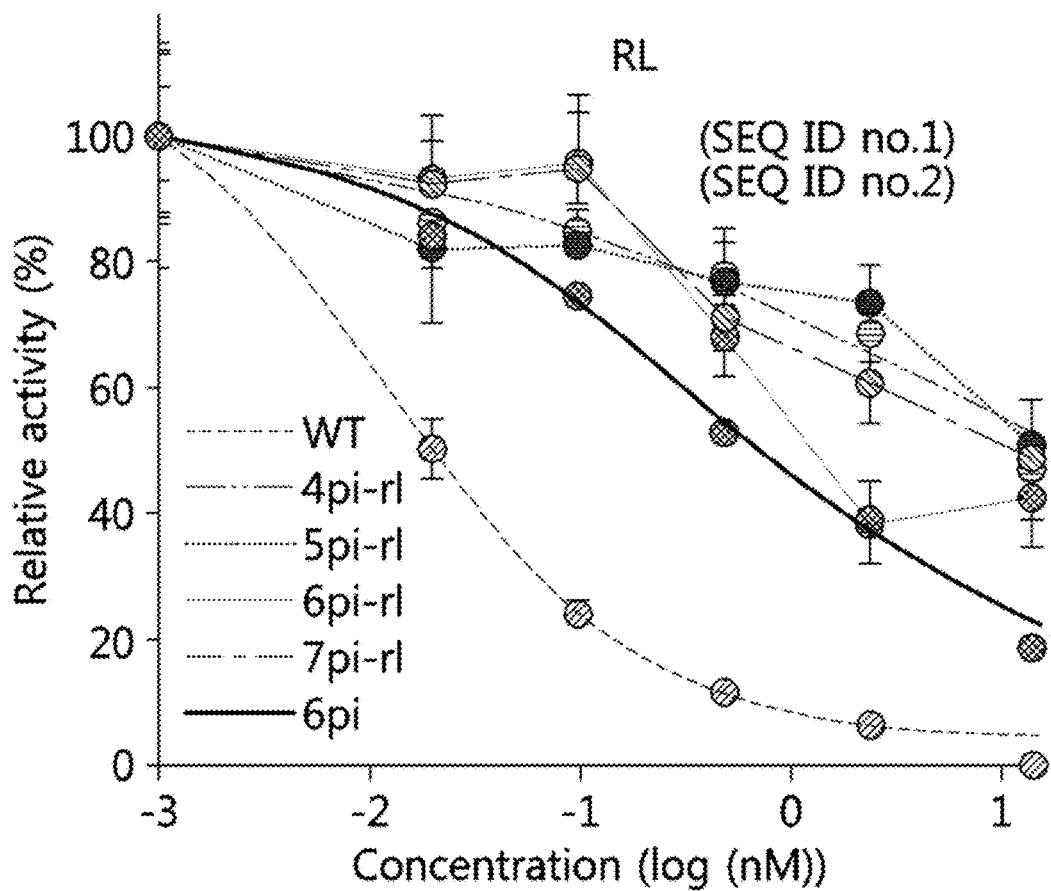
FIGS. 5a, 5b, 5c, 5d and 5e show the effects of modified siRNAs with ribonucleotide spacer (rSpacer) insertion on gene silencing activity and miRNA-like off-target effects.
Figure 5B:
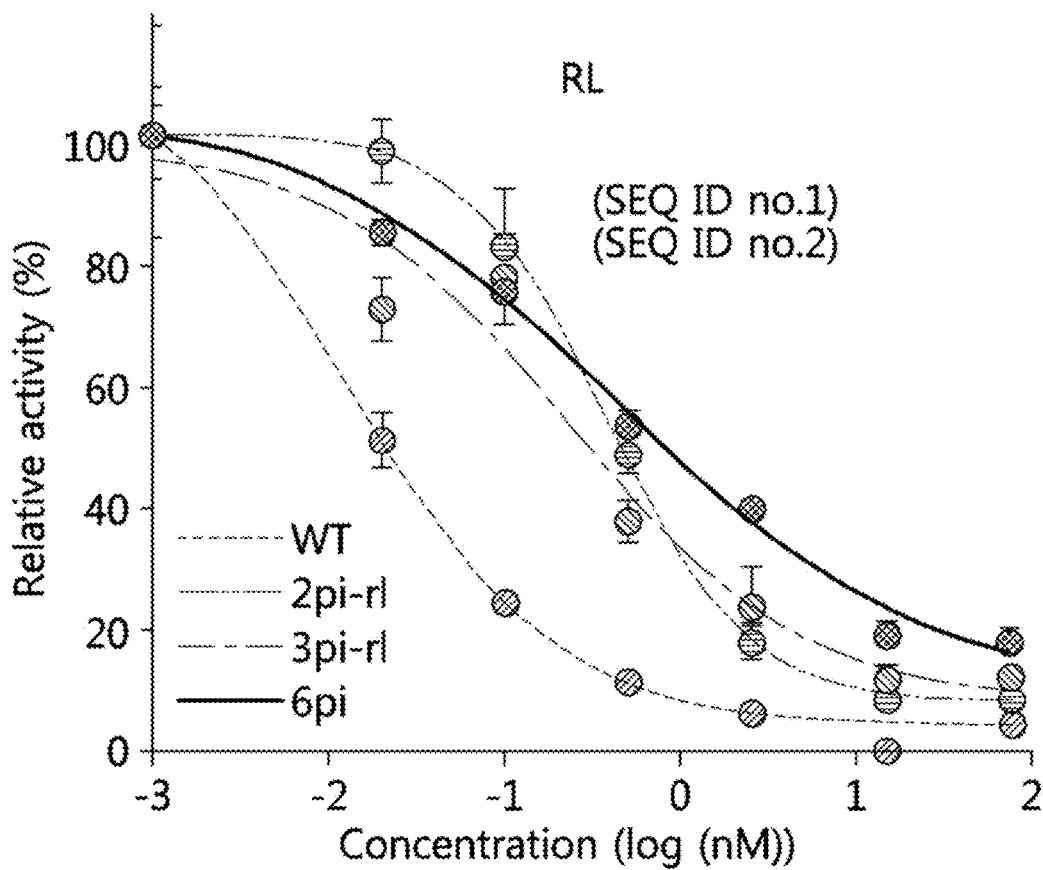
Figures 5C, 5D:
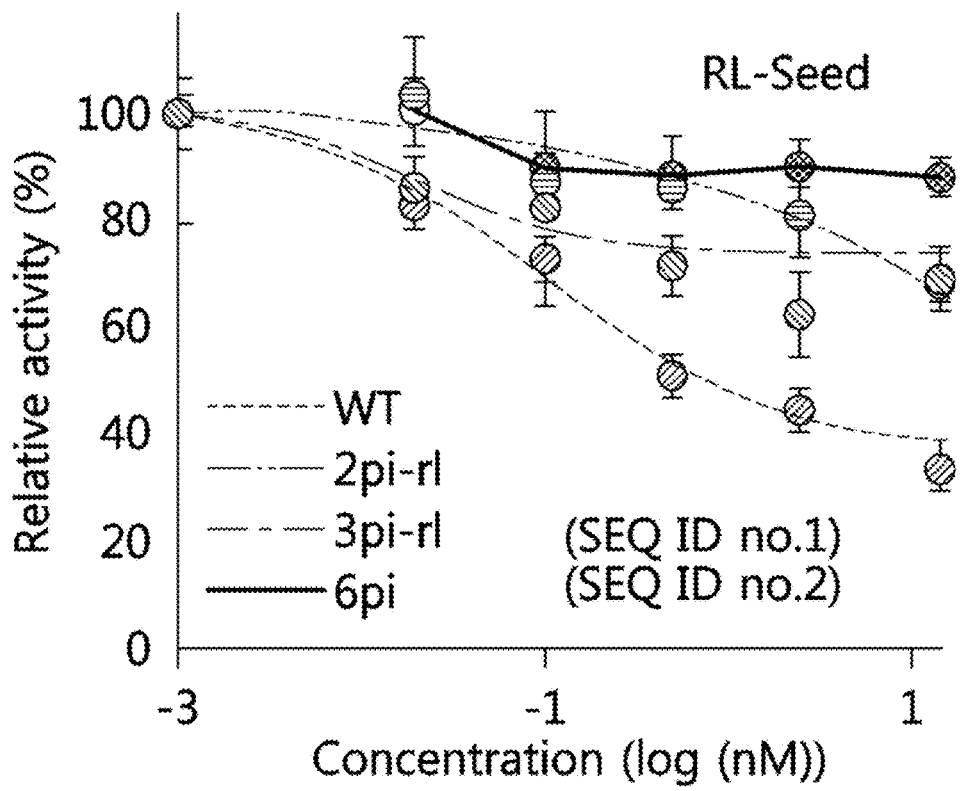

As a result, as shown in FIGS. 5a, 5b and 5c, every modification in seed region showed superior on-target activity, more than 20% of Imax. Especially, 2 pi-rI and 3 pi-rI showed potent on-target activity better than 6 pi, but they still silence off-targets as reported in FIG. 5d, wherein the measuring the off-targets was performed by using the same method in the example 1.

Figure 5E:
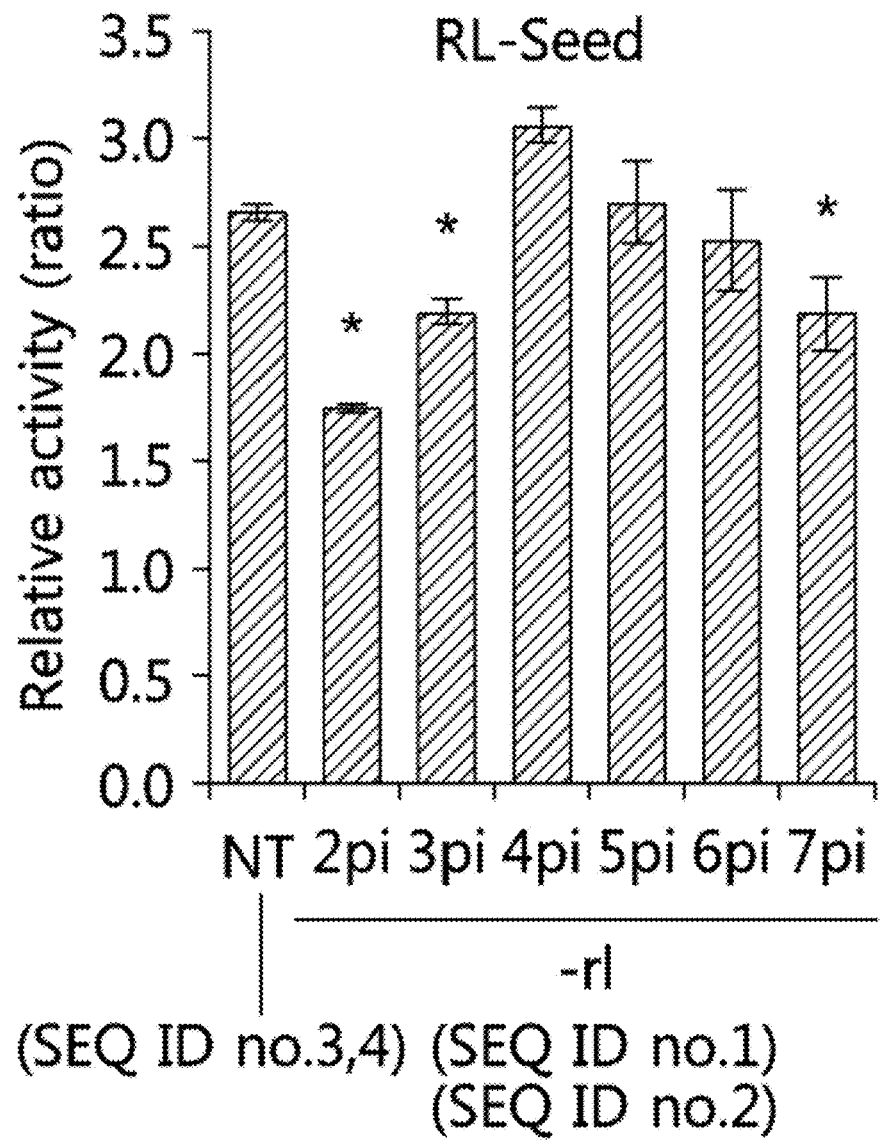

In addition, every modification (4 pi-rI, 5 pi-rI, and 6 pi-rI) except 2 pi-rI, 3 pi-rI and 7 pi-rI was observed to abrogate off-target effects as shown in FIG. 5e, wherein the off-target effects were estimated for each modification at 75 nM siRNA concentration.

In view of the above, it was confirmed that the guide strand of the siRNA molecule should be appropriately used by inserting ribonucleotide spacer (rSpacer) into position 4 or 6 from the 5' end region, wherein the most appropriate usage is to substitute position 6 to dSpacer (6 pi), considering the effect on target gene repression and off-target avoidance.

[Example 5] Loss of Function in Target Gene Regulation by microRNA Molecules Having Substitution Modification of 6th Nucleotide from the 5' End to Deoxyribonucleotide Spacer (dSpacer) and Comparison with the Effect from 2'OMe Modification As validated by the example 1 above, the siRNA molecule with abasic substitution derived from the present invention abrogates miRNA-like off-targets caused by a conventional structure of siRNA, thereby to further validated the modification by applying to miRNA, miR-124 (SEQ ID NO: 5) was modified to contain deoxynucleotide substitution in position 6 from the 5' end, then examined by performing following experiments below. Initially, the same sequence of human miR-124-3p (SEQ ID NO: 5) and the sequence containing 6 pi, dSpacer substitution in position 6, were synthesized, then cotransfected (SEQ ID NOS: 5 and 6) into HeLa cells with psi-check2 vector containing two miR-124 seed sites (the perfect complementary sequence to position 1-8 from the 5' end region). Then the luciferase activity was measured at various concentrations of RNA by using the method in example 1 above.

Figure 6A:
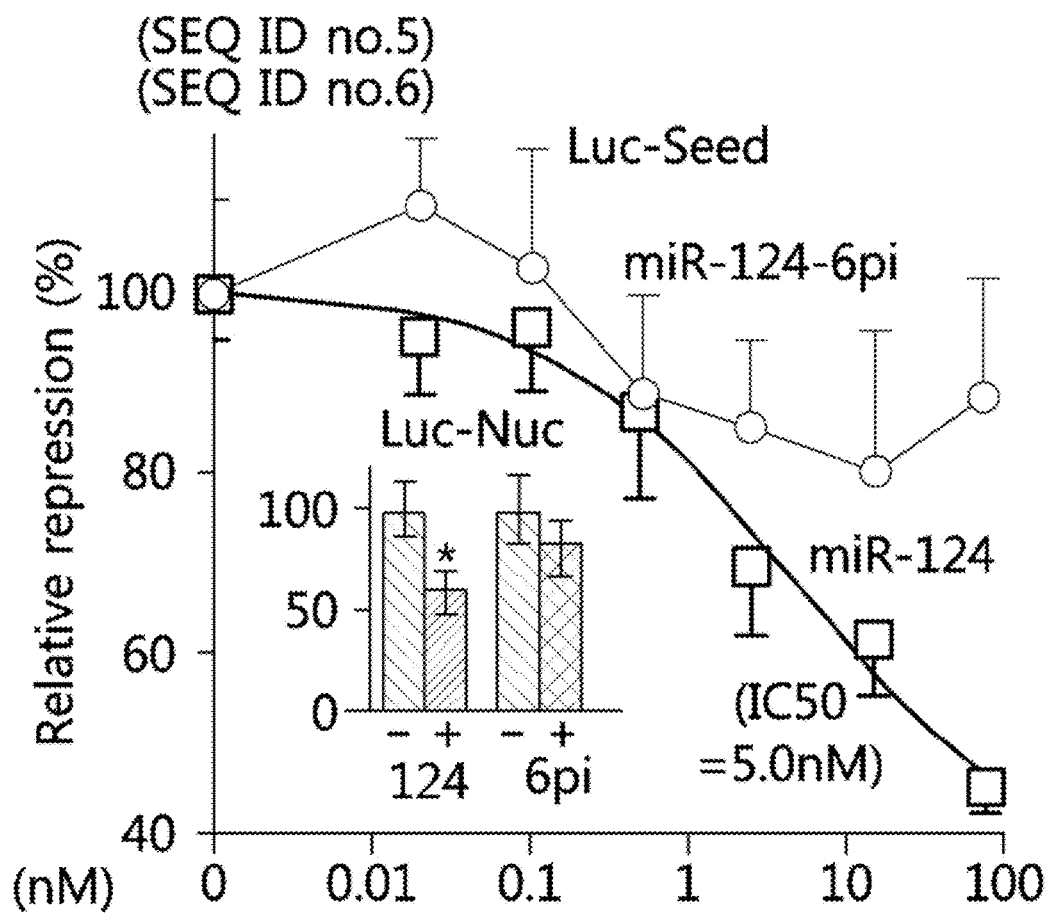
FIGS. 6a, 6b, 6c, 6d, 6e, 6f and 6g show the effects of a modified siRNA molecule, which contains deoxyribonucleotide spacer (dSpacer) substituted for sixth nucleotide from the 5' end (6 pi), on function of miRNA-mediated target gene regulation, compared with the effect from conventional siRNA modified with 2'OMe in position 2 from the 5' end.

As a result, as shown in FIG. 6a, it was confirmed that miRNA having the 6 pi, the modification of the present invention (miR-124-6 pi), cannot repress the seed sites where they are previously known to be recognized. In addition to the seed sites, we also validated that 6 pi modification cannot affect nucleation bulge sites (Nuc), the sites known to be recognized by miRNA.

Furthermore, genome wide validation was conducted to confirm whether miR-124-6 pi actually avoids repression of various genes which have been usually affected by the unmodified miR-124, wherein miR-124, miR-124-6 pi, and the control were transfected into HeLa cells where miR-124 is not expressed, wherein total RNA was extracted by using RNAeasy kit (Qiagen) after 24 hours from the transfection, thereby performing RNA-Seq analysis, a gene expression experiment based on sequencing analysis, which is provided by Otogenetics company. As a result from the experiment above, FASTAQ files were generated and further serially analyzed by using TopHat, Cufflink and Cuffdiff program, wherein values were finally normalized as log 2 ratio by using the result from original HeLa cells, wherein the values should be reported as significant by statistical analysis provided by Cuffdiff, in order to be selected for the analysis.

Figure 6B:
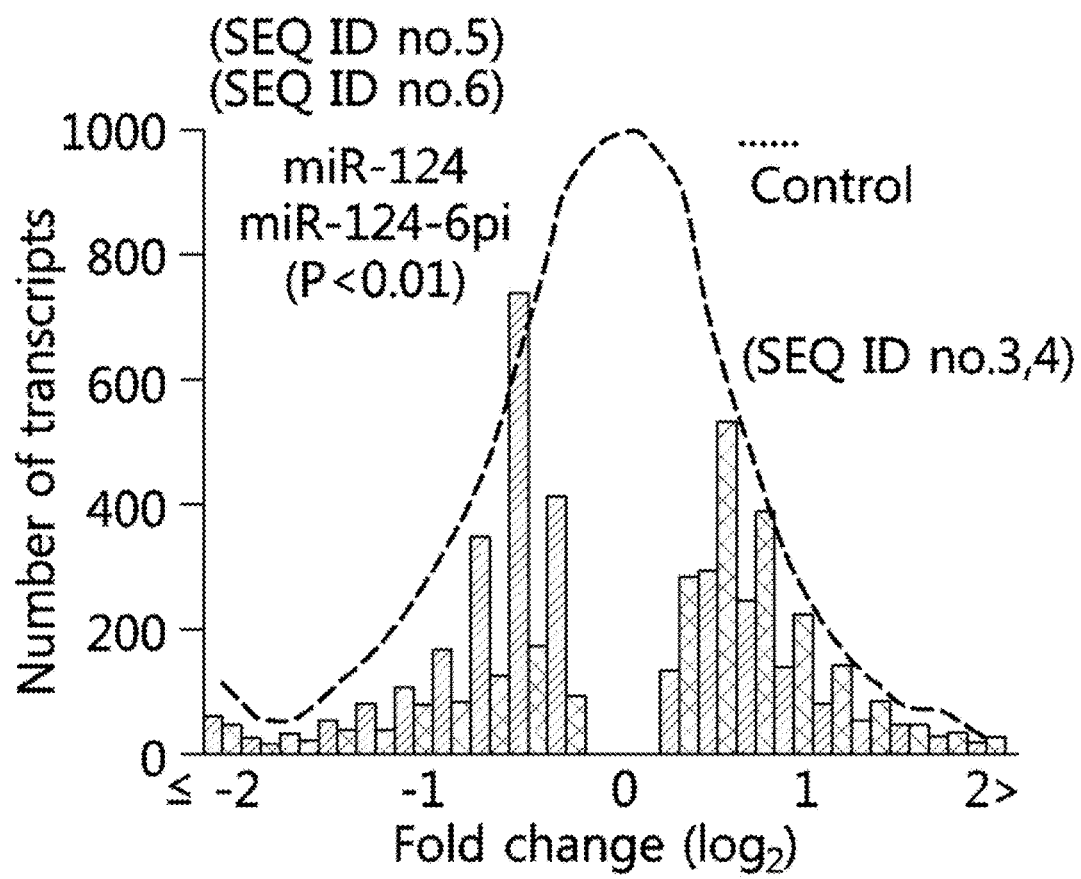
Figure 6C:
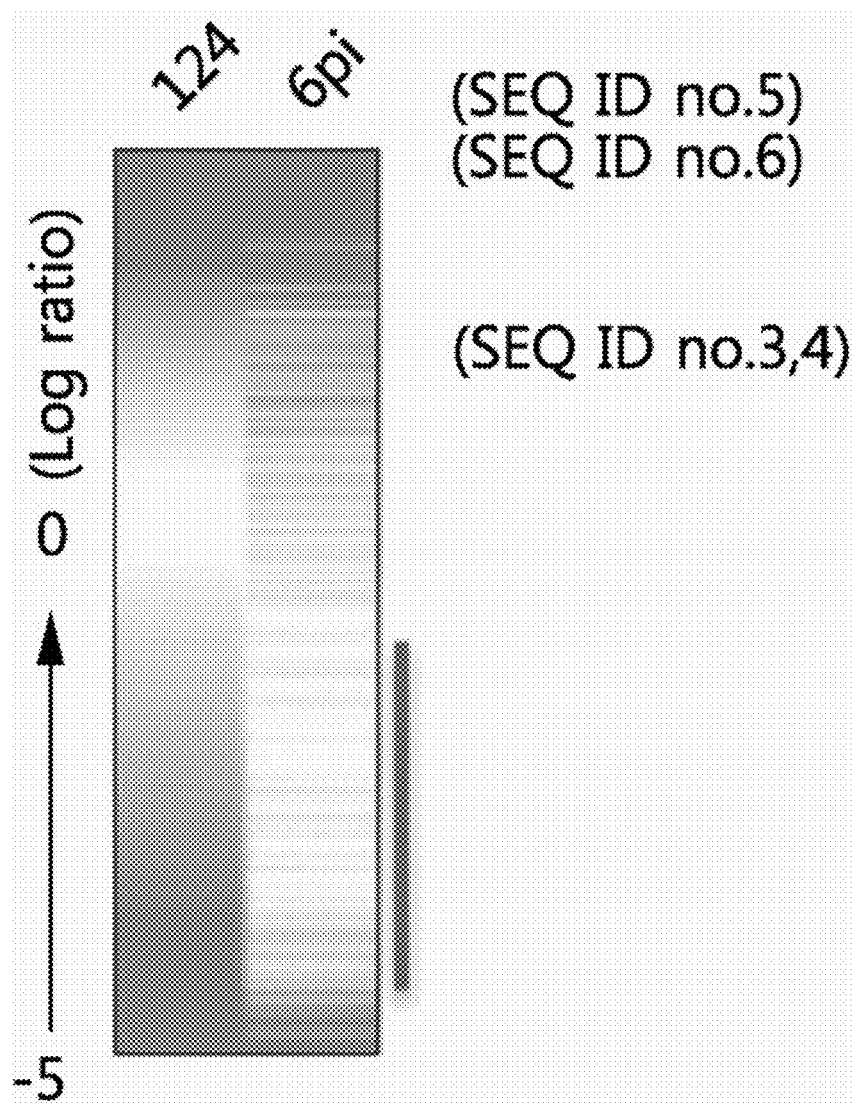

As a result, as shown in FIG. 6b, it was observed that the control showed both up- and down-regulation in gene expression at the same extent, but the miR-124 increased the significant portion of down-regulated genes, wherein, in the case of the 6 pi modification, such down-regulated genes were significantly reduced in their number. Furthermore, as shown in FIG. 6c, heatmap representation significantly showed that large number of miR-124 dependent down-regulated genes were unable to be repressed by mir-124-6 pi, wherein the extent of repression mediated by miR-124 was sorted to examine total genes for miR-124 and miR-124-6 pi, finally represented as the heatmap.

Figure 6D:
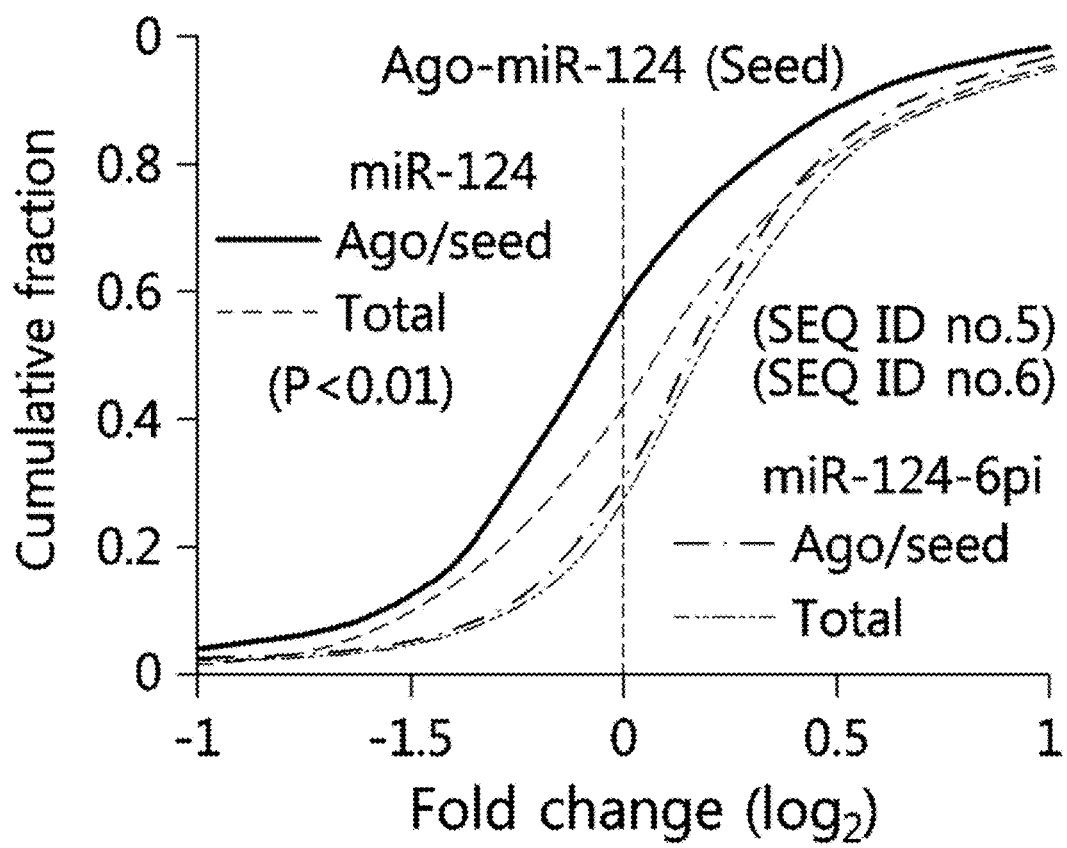

Furthermore, in order to see whether the 6 pi modification abrogates interaction between miRNA and target mRNA, potential cause of the observation above, Ago HITS-CLIP analyses was performed for miR-124 transfected HeLa cells, wherein sequences from the Ago HITS-CLIP were analyzed to generate a map of all binding sites in mRNA, then further compared with the results from original HeLa cells expressing control, thereby precisely identified Argonaute binding sites generated by miR-124 expression at genome-wide level. Such miR-124 binding sites were named as de novo Ago-miR-124 clusters, wherein their cumulative fraction was analyzed depending on the extent of repression for the comparison, focusing on the target mRNA which contains miR-124 seed sites in these binding, wherein the extent of repression was estimated by mRNA profiling results for miR-124 or miR-124-6 pi expressed HeLa cells As a result, as shown in FIG. 6d, the target mRNAs bound by miR-124 were significantly repressed relative to total mRNA expression (KS test, P<0.01), but the case of miR-124-6 pi was not statistically significant. Based on this, we confirmed that miR-124-6 pi is unable to repress conventional target mRNAs of miR-124 in genome-wide level, wherein, for the miR-124-6 pi, position 6 from the 5' end of miR-124 was modified to be substituted to abasic single deoxynucleotide.

2'OMe modification, developed by Dharmacom company, has been conventionally used to prevent siRNA off-targets. This is an empirical method which applies 2'OMe modification to position 2 from the 5' end of guide strand to prevent the corresponding miRNA-like off-target effects. The present inventors applied the 6 pi modification of the present invention to siRNA for silencing *renilla* luciferase (SEQ ID NO: 1) and also applied 2'OMe to it, wherein they evaluated the efficiency of on-target effect based on IC50 derived by measuring repression in various concentrations using the same method in Example 1 above.

Figure 6E:
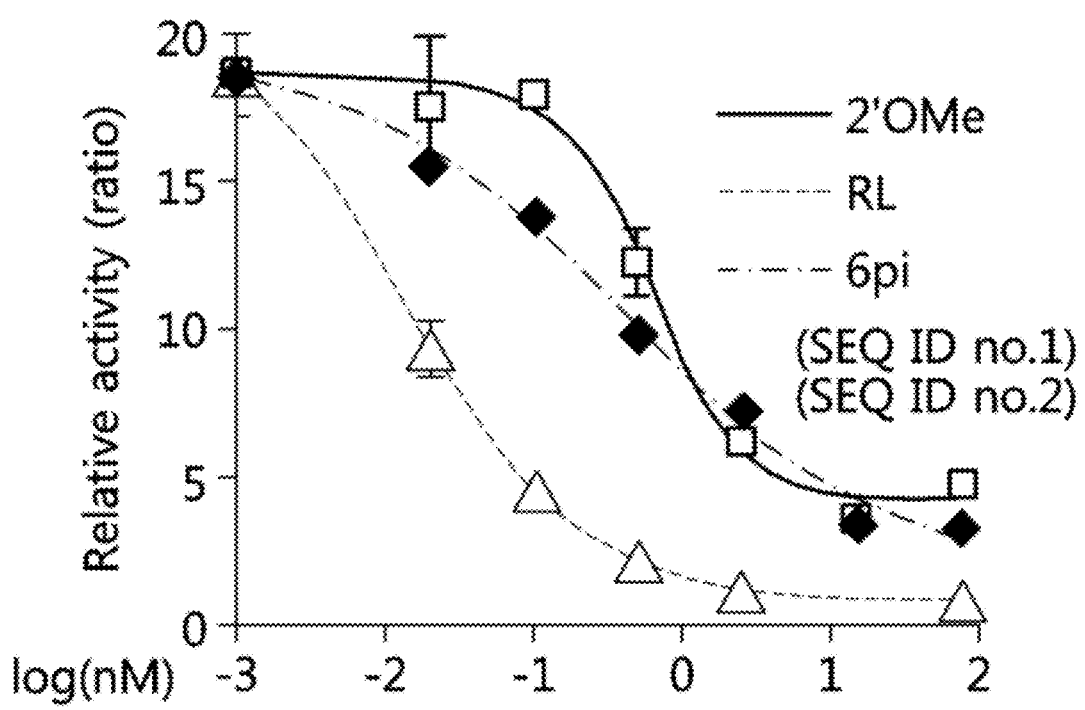
Figure 6F:
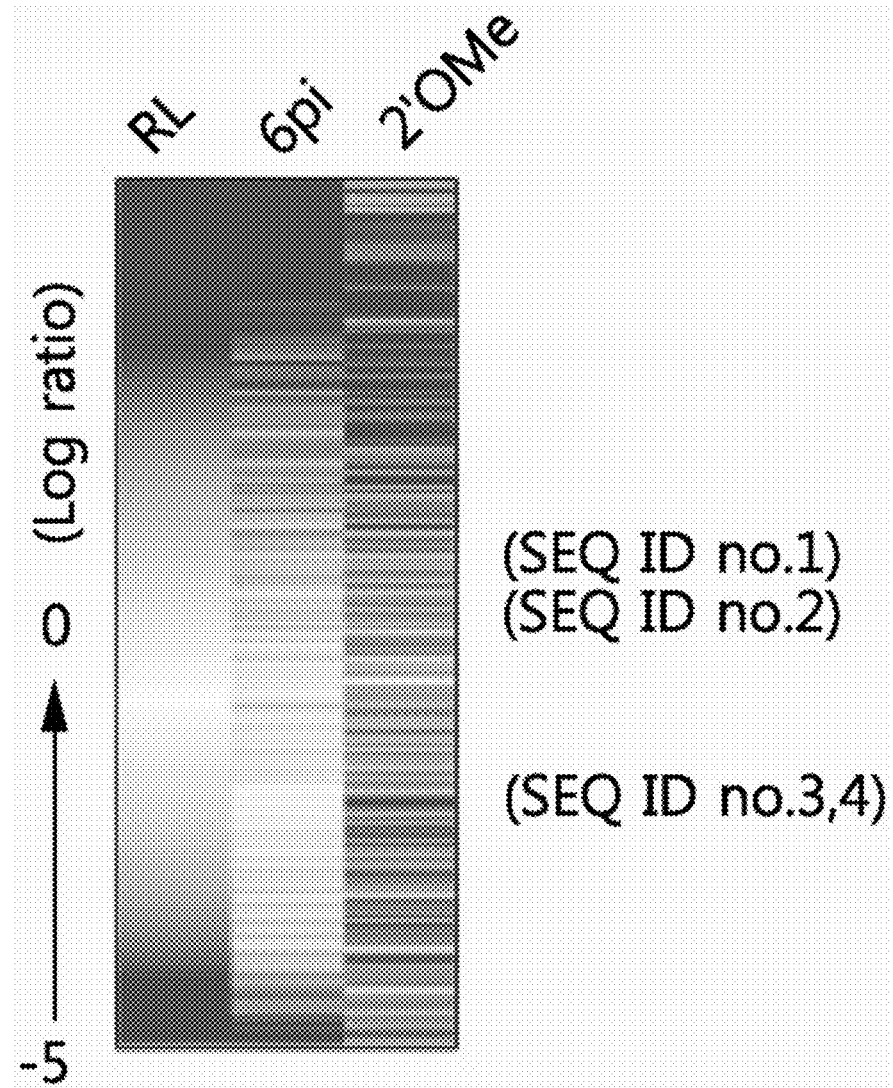

As a result, as shown in FIG. 6e, the 6 pi modification not only showed superior efficiency of the repression than 2'OMe, but also showed excellent maximal inhibition rate. Furthermore, genome-wide off-target effects were evaluated by the same RNA-seq method and heatmap analyses above, confirming that 2'OMe modification cannot abrogate off-target silencing in siRNA as much as 6 pi.

Additionally, 6 pi or 2'OMe modification was applied to miR-124, of which function is known to induce neuronal differentiation, to see whether the modification mediated abrogation of miRNA-like targeting is efficient enough to inhibit its biological function, wherein miRNA with these modifications were transfected into N2a cell (Neuro-2a, ATCC CCL-131), then examined through microscope after 72 hours from the transfection to see whether they can generate terminal neuron structures.

Figure 6G:
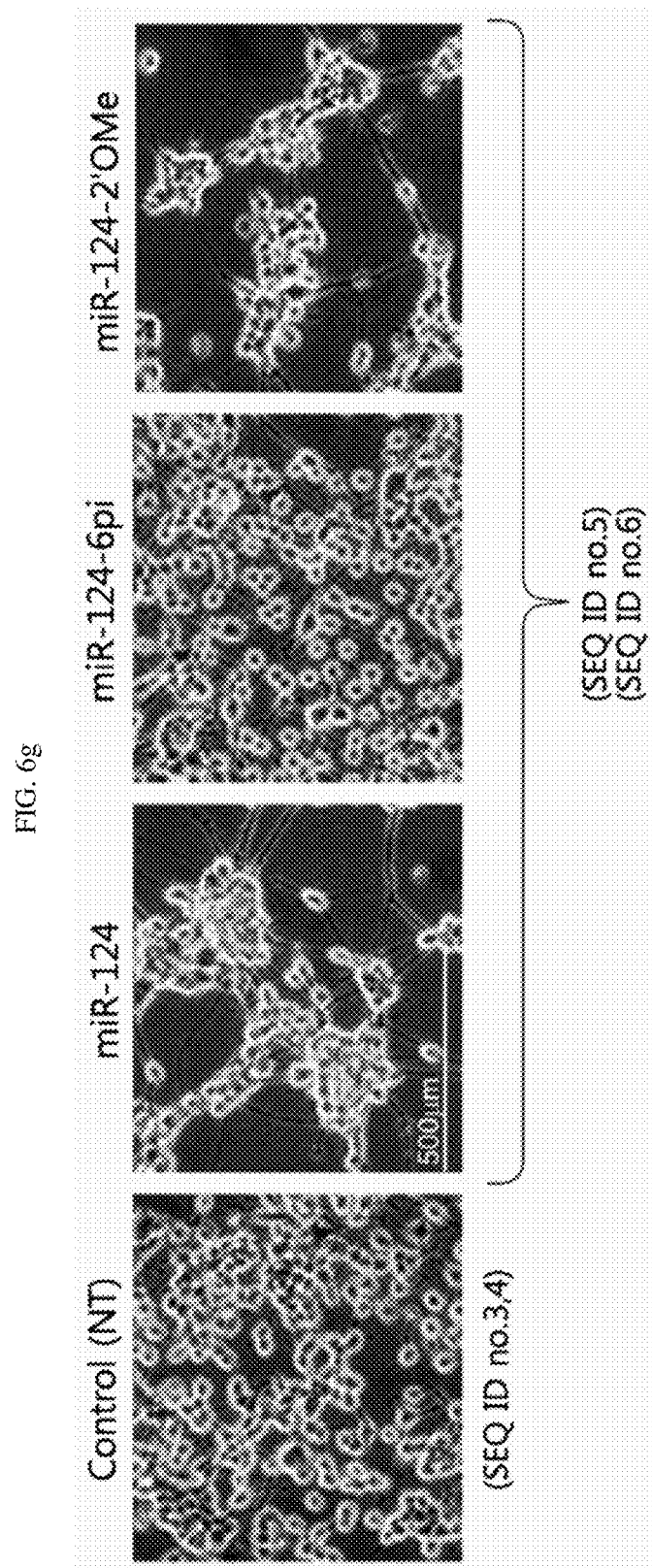

As a result, as shown in FIG. 6g, miR-124-2me still possessed the capability to induce the structure of terminal neuron, but miR-124-6 pi completed lose such ability, wherein miR-124-2me is the case where 2'OMe modification was applied.

Based on the above, considering the effect on off-target silencing, it was confirmed that the 6 pi modification shows excellent avoidance of binding and silencing of miRNA-like off-targets, thereby the 6 pi modification completely block the biological function in miRNA, wherein 6 pi modification is the substitution of position 6 from the 5' end to deoxyribonucleotide spacer (dSpacer), whereas on-target efficiency of the conventional 2'OMe modification is not better than 6 pi, wherein the 2'OMe modification only marginally reduces off-targets, showing the limitation that the off-target cannot be completely blocked

Figure 7A:
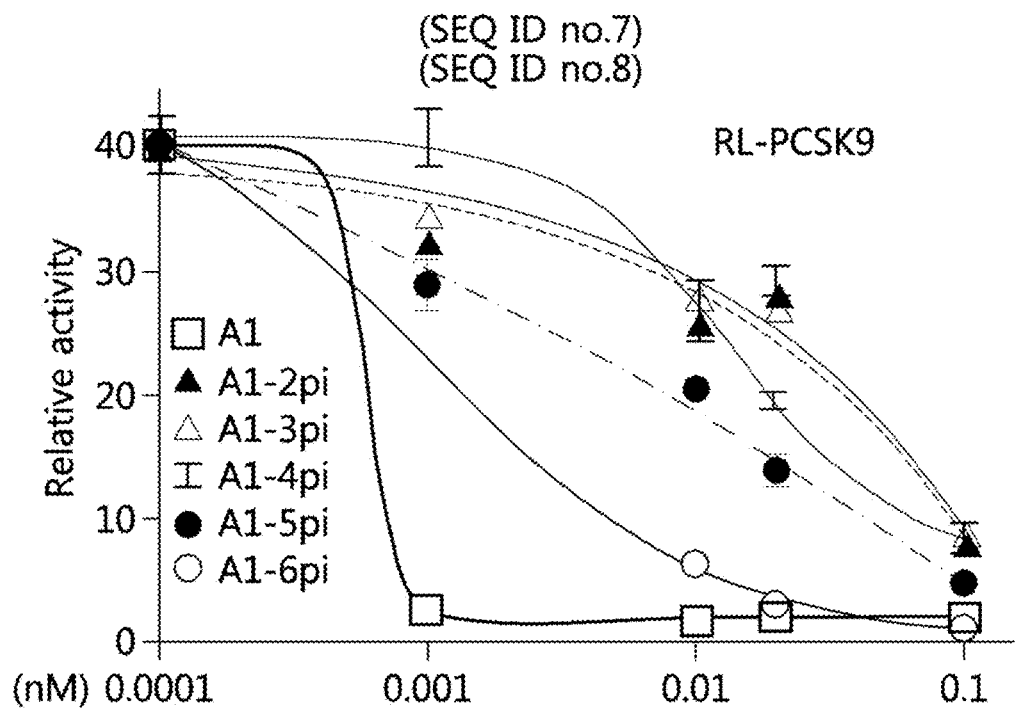
FIGS. 7a, 7b, 7c, 7d, 7e, 7f, 7g. 7h and 7i show the results evaluating off-target effects in cells with PCSK9 siRNAs containing the modification of the present invention, 6 pi.
Figure 7B:
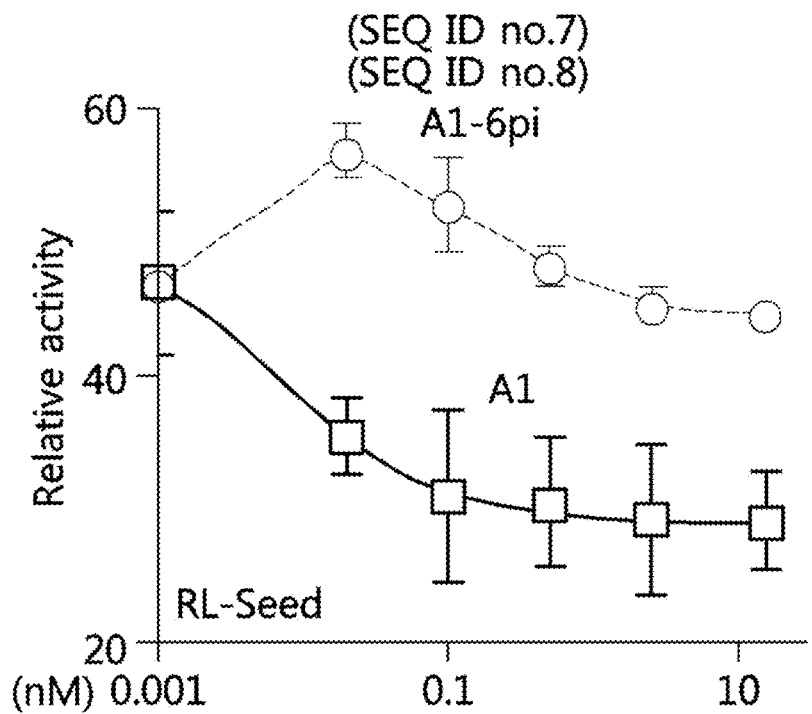
Figure 7C:
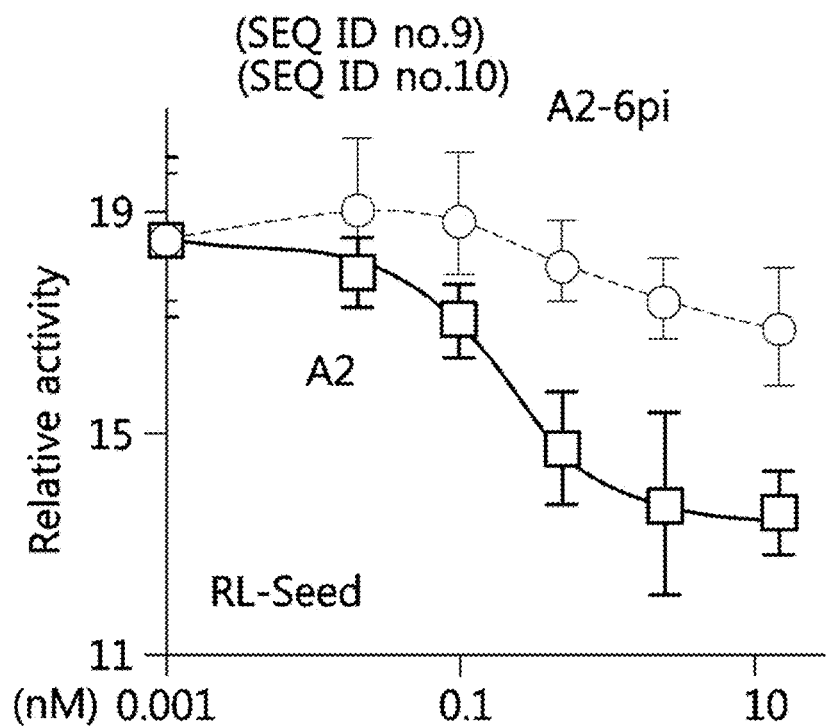
Figure 7D:
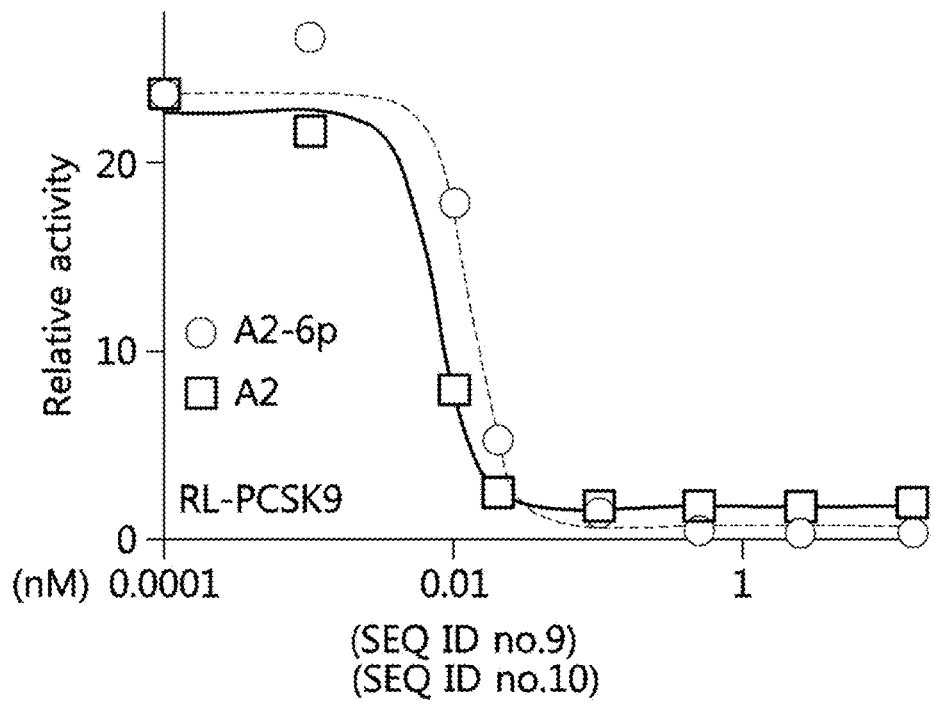

[Example 6] Off-Target Effects of siRNA Developed for Reducing Plasma Cholesterol and Comparison of Improvement by Applying Spacer Modification In order to evaluate the effect of the present invention, the modification was applied to siRNA sequences of which purpose of usage can be expanded from experiments to therapeutics, wherein the siRNA sequences were developed to lower plasma cholesterol by repressing PCSK9 gene in liver through inducing RNA interference, wherein the experiments were performed for PCS-A1 (A1, SEQ ID NOS: 7 and 8) and PCS-A2 (A2, SEQ ID NOS: 9 and 10) (Proc Natl Acad Sci USA. 2008 Aug. 19; 105(33):11915-20), which were developed by Alnylam company. The on-target activity was compared for A1 (SEQ ID NO: 7) with different position of abasic modification by measuring luciferase activity using the same method in example 1, showing that A1-6 pi has the most superior efficiency of target gene silencing and, as represented in FIG. 7a, it also completely abrogates off-target effect mediated by the seed region. A2 (SEQ ID NO: 9) has the same sequence as A1, but contains 2'OMe modification in several positions to solve the problem of innate immune response and also to improve RNA stability, wherein the 6 pi modification in A2 siRNA molecule also abrogates off-targets as validated in FIG. 7c, estimated by the luciferase reporter assay using the same method in Example 1. Additionally, as represented in FIG. 7d, A2-6 pi showed almost the same on-target silencing activity as the unmodified A2, observed by measuring IC50 using the luciferase reporter.

Since it was observed that every siRNA for PCSK9 gene caused miRNA-like off-target effects in luciferase reporter assays, additional experiments were performed in human liver cancer cell line, HepG2 (ATCC HB-8065), to validate the off-target effects actually happening in liver cell. Initially we examined whether A2 can efficiently reduce PCSK mRNA as siRNA for PCSK9 gene, wherein the A2 and the A2-6 pi siRNAs were transfected into HepG2 cells using Lipofectamine RNAiMAX (Invitrogen) reagent according to the provided protocol, then total RNA was extracted after 24 hours by RNeasy kit (Qiagen) and reverse transcribed by Superscript III RT (Invitrogen) according to the provided protocol, thereby amount of PCSK9 mRNA was quantitated by performing qPCR with SYBR® Green PCR Master Mix (Applied Biosystems) and normalized by GAPDH mRNA level.

Figure 7E:
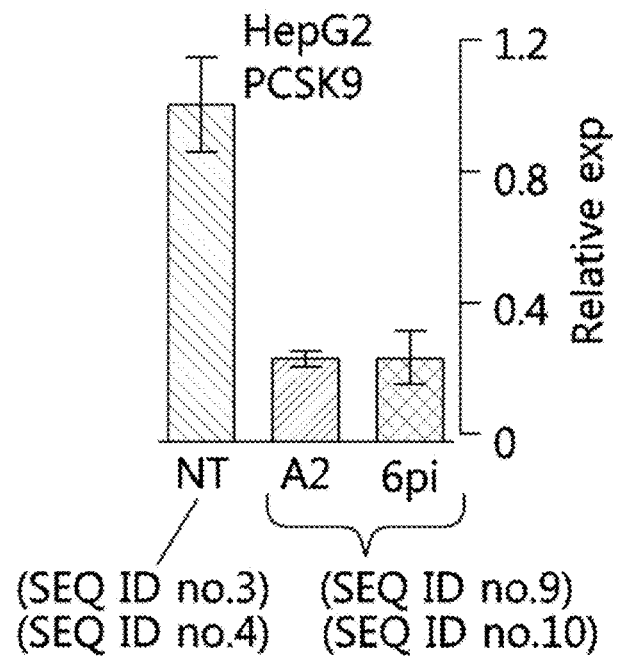

As a result, A2 and A2-6 pi are validated for on-target effects that they both efficiently repress PCSK9, as shown in FIG. 7e.

After that, NSR RNA-Seq method (Nat Methods. 2009 September; 6(9):647-9) was used to construct the library from total RNA, wherein total mRNA expression was investigated by analyzing the library using HiSeq2000 sequence analyzer (Illumina company), thereby genome-wide expression was analyzed with heatmap representation by using the same method in Example 2.

Figure 7F:
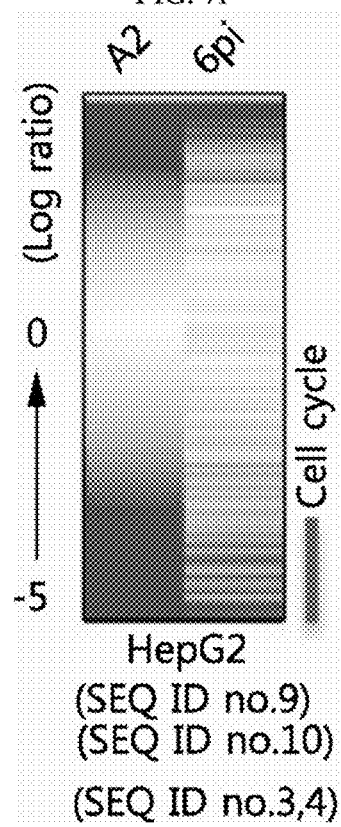

As a result, as shown in FIG. 7f, it was observed that mRNA level of off-target genes suppressed by A2 was recovered by 6 pi modification.

Furthermore, the off-target genes showing such changes were analyzed by performing GO (gene ontology) analysis using DAVID program (Nature Protoc. 2009; 4(1):44-57), thereby finding that many genes with cell cycle related functions were significantly silenced via off-target effects. To confirm the putative off-target effects, corresponding siRNAs were transfected into HepG2, synchronized for cell cycle by eliminating 10% serum (FBS) from the media for 24 hours, then analyzed for cell cycle after 48 hours by using propodium iodide and FACS machine.

Figure 7G:
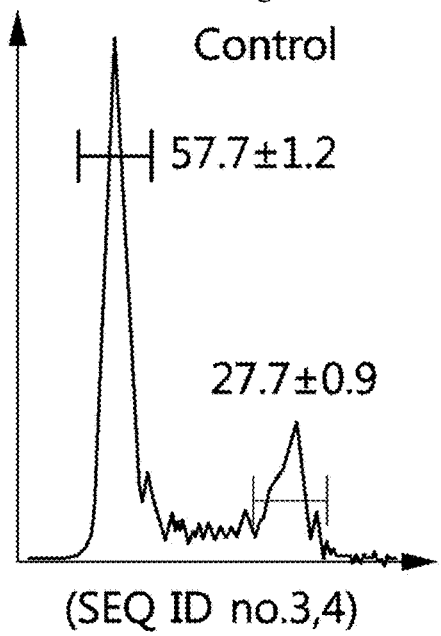
Figure 7H:
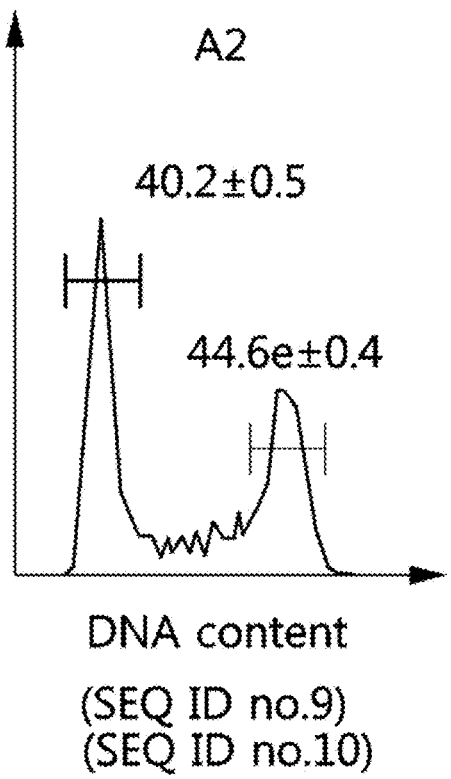
Figure 7I:
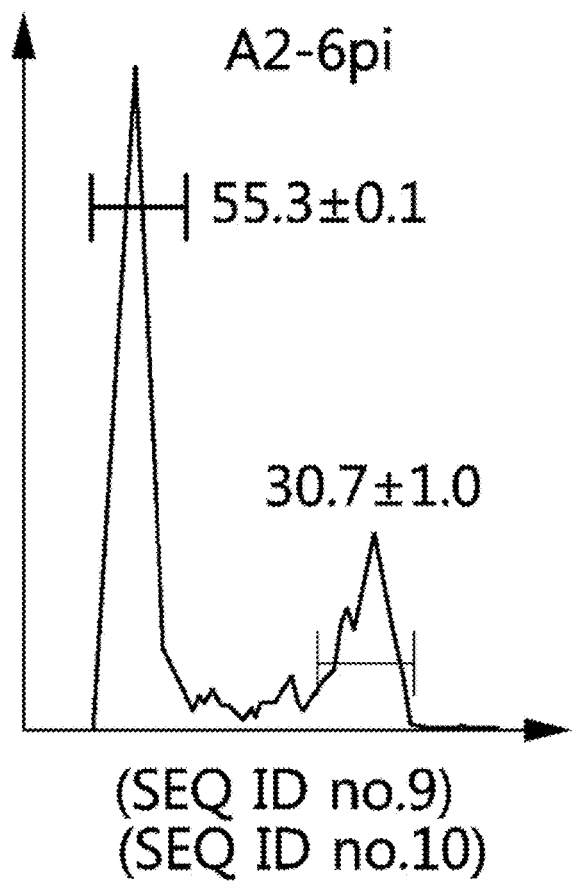

As a result, as shown in FIGS. 7g, 7h and 7i, defect in cell cycle was observed as expected when A2 siRNA molecule was expressed, especially wherein cell cycle arrest in G1/G2 was increased, but the phenotype was disappeared when 6 pi was introduced.

Based on the above, it was confirmed that siRNAs for PCSK9 causes deleterious cell cycle arrest in human liver cell as unexpected off-target effects, but such adverse off-target side effects can be blocked by applying the 6 pi modification of the present invention, wherein the 6 pi also maintains on-target silencing activity.

[Example 7] Off-Target Effects Caused by PCSK9 siRNA Through In Vivo Deliver in Mouse and Evaluation of the Improvement by Applying Spacer Modification In order to estimate off-target effects in vivo, siRNA was delivered to liver tissue by using 7 weeks-old mice (C57/BL6) for the experiments, wherein the evaluation was performed for the off-target effects which was analyzed for PCSK9 siRNAs (SEQ ID NOS: 9 and 10) in Example 6. Each siRNA was delivered to liver tissue by injecting 5 mg/kg of siRNA via tail veins of 5 mice (tail-vein injection), then the mice were sacrificed after 48 hours to dissect liver tissue and extract blood for the experiments. Initially, total RNA including small RNA was extracted from the part of dissected liver tissues using miRNeasy kit (Qiagen), then the amount of each delivered siRNA and the target mRNA, PCSK9, was quantitated by qPCR. For quantification of siRNA, we followed the protocol (Biotechniques. 2005 October; 39(4):519-25) using poly(A) tailing Kit (Ambion), which first attached adenosines to the 3' end of RNAs, wherein reverse transcription was performed by Superscript III RT (Invitrogen) using oligo-dT containing a specific sequence, thereby qPCR was conducted with SYBR® Green PCR Master Mix (Applied Biosystems) and by using the pair of DNA primers, one recognizes the specific sequence in oligo-dT and the other has the same sequence of siRNA. The Quantitation of PCSK9 mRNA was conducted by the same method in example 6. The amount of total plasma cholesterol was measured by ELISA method using the kit from Wako company according to the provided protocol.

Figure 8A:
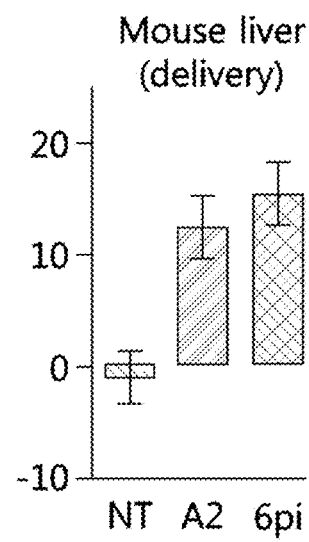
Figure 8B:
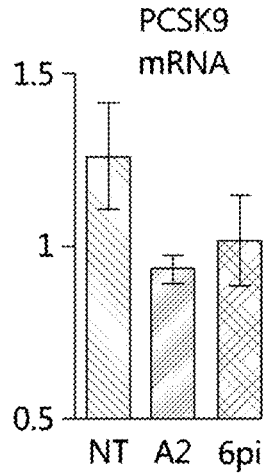
Figure 8C:
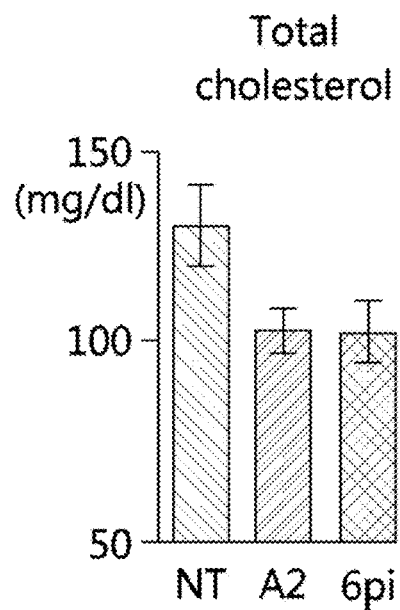

As a result, as shown in FIGS. 8a, 8b and 8c. A2-6 pi, modified to have the spacer, was validated to be delivered to the liver tissue, repress PCS K9 mRNA, and reduce plasma cholesterol as well as A2 siRNA (SEQ ID NO: 9).

Furthermore, RNA-Seq analyses were conducted by following the same method in example 5 above, wherein total RNA was obtained from the live tissue where the delivery of each siRNA was confirmed.

Figure 8D:
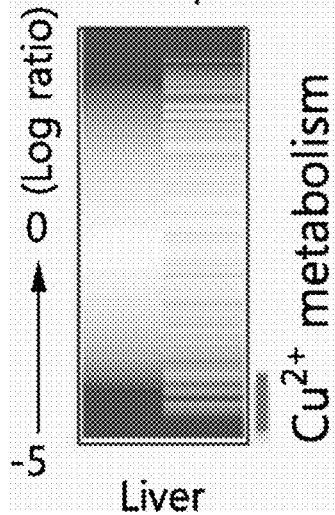

By analyzing the results as heatmap representation, as shown in FIG. 8d, the 6 pi modification was confirmed to reduce genome-wide off-targets.

In addition, functions of off-targets was examined by using GO analysis, applying to genes repressed by A2 siRNA, wherein it was found that off-targets play roles in copper ion metabolism in liver tissue, thereby defect in copper ion metabolism was expected, examined by using the mouse liver cell, NCTC clone 1469 (Korean cell line bank). In detail, control, A2, or A2-6 pi siRNA was transfected into NCTC clone 1469 using lipofectamine 2000, and amount of copper ion was quantified by using QuantiChrom Copper Assay Kit (bio systems) at 72 hours after transfection.

Figure 8F:
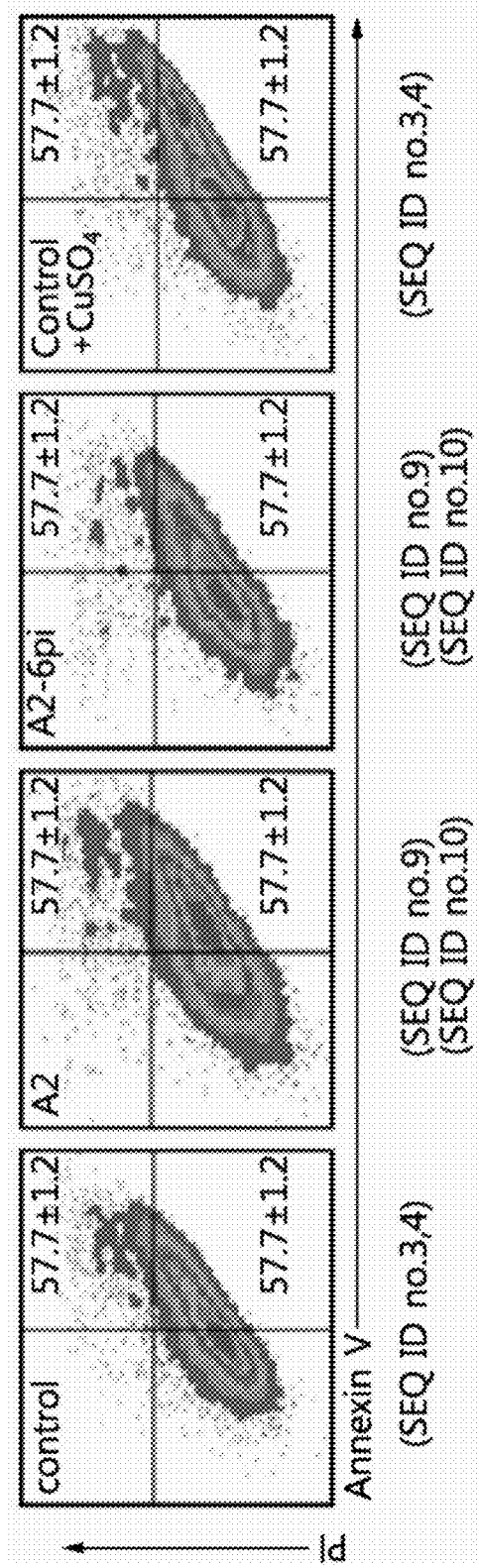

As a result, as shown in FIG. 8e, it was validated that cellular copper ion in increased by A2 but not increased by A2-6 pi. Increase of copper ion in liver tissue is known to induce cell death, thus cell death was quantitated by using Annexin V: FITC Apoptosis Detection Kit II (BD Pharmingen), wherein the assay was performed at 72 hours after transfection, wherein the transfection was performed for the expression of control (SEQ ID NOS: 3 and 4), A2, and A2-6 pi into NCTC clone 1469, wherein FACS was used after the stain with PI and Annexin V according to the provided protocol, wherein A2 induced cell death was observed as the similar extent to the result from 32 uM CuSO4 treatment, but in the case of A2-6 pi the cell death was disappeared as shown in FIG. 8f.

Based on the results above, the siRNAs for PCSK9 is turned out to suppress the copper ion metabolism as unexpected off-target phenotypes when it was injected into mice and delivered to liver tissue, thereby increasing copper concentration in liver tissue and inducing cell death as unexpected adverse side effects. Nevertheless, it is turned out that 6 pi modification of the present invention abrogates adverse off-target effects even in vivo as well, while maintaining efficiency of on-target silencing against PCSK9.

[Example 8] Comparison of Target Gene Silencing and Off-Target Effect Between Deoxyribonucleotide Spacer (dSpacer) Substituent and Conventional Substituent Modified for Inhibiting Off-Target Effects Modified by the present invention validated to abrogate off-target effect and to silence the target gene, a dSpacer substituent was compared with conventional modified substituents for the performance in suppressing off-target effects by measuring IC50 using the same method in Example 1, wherein the dSpacer substituent contains a deoxynucleotide spacer substituted for a nucleotide in the position 6.

First, as a conventional substituent, a method of introducing a mismatch into position 2-8 from the 5' end was applied, introducing mismatch base-pairing into position 6 from the 5' end of miR-124 (miR-124-6 mm, SEQ ID NOS: 13 and 14), wherein IC50 was measured. As a result, represented in FIGS. 9a, 9b, 9c and 9d, miR-124-6 mm showed superior silencing activity to perfectly complement target (perfect match target) as much as the unmodified miR-124 (both IC50=0.02 nM, SEQ ID NOS: 11 and 12), but it did not repress miR-124 seed targets (positions 2-8 from the 5' end).

Figure 9A:
FIGS. 9a, 9b, 9c, 9d, 9e, 9f, 9g, 9h, 9i and 9j show the result comparing the present invention with conventional siRNAs having mismatch base-pairing, 2'OMe modification and UNA modification in position 6 from the 5' end and siRNA duplex with introduction of bulge in position 2, examining the effect on gene silencing activity and miRNA-like off-target effects.
Figure 9B:
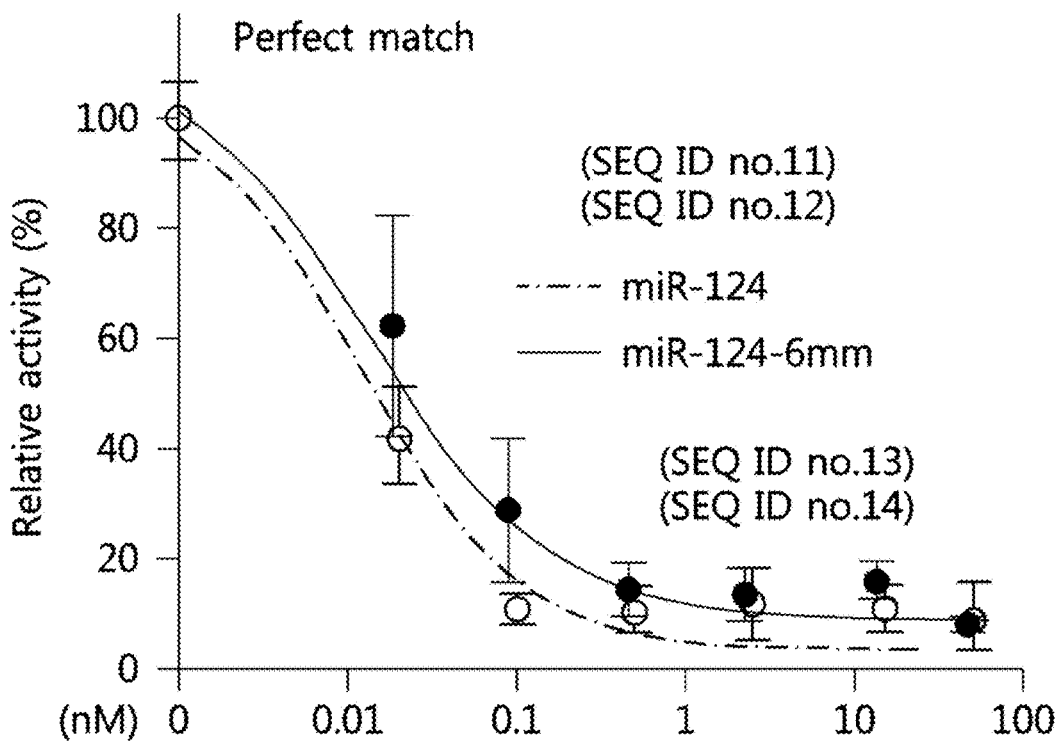
Figure 9C:
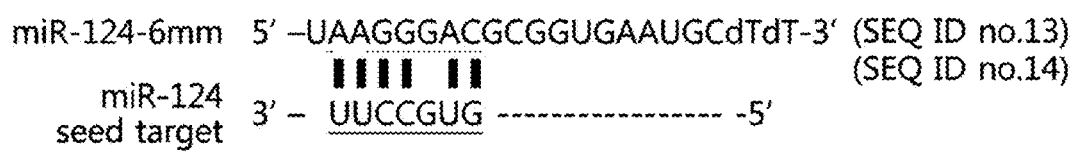
Figure 9D:
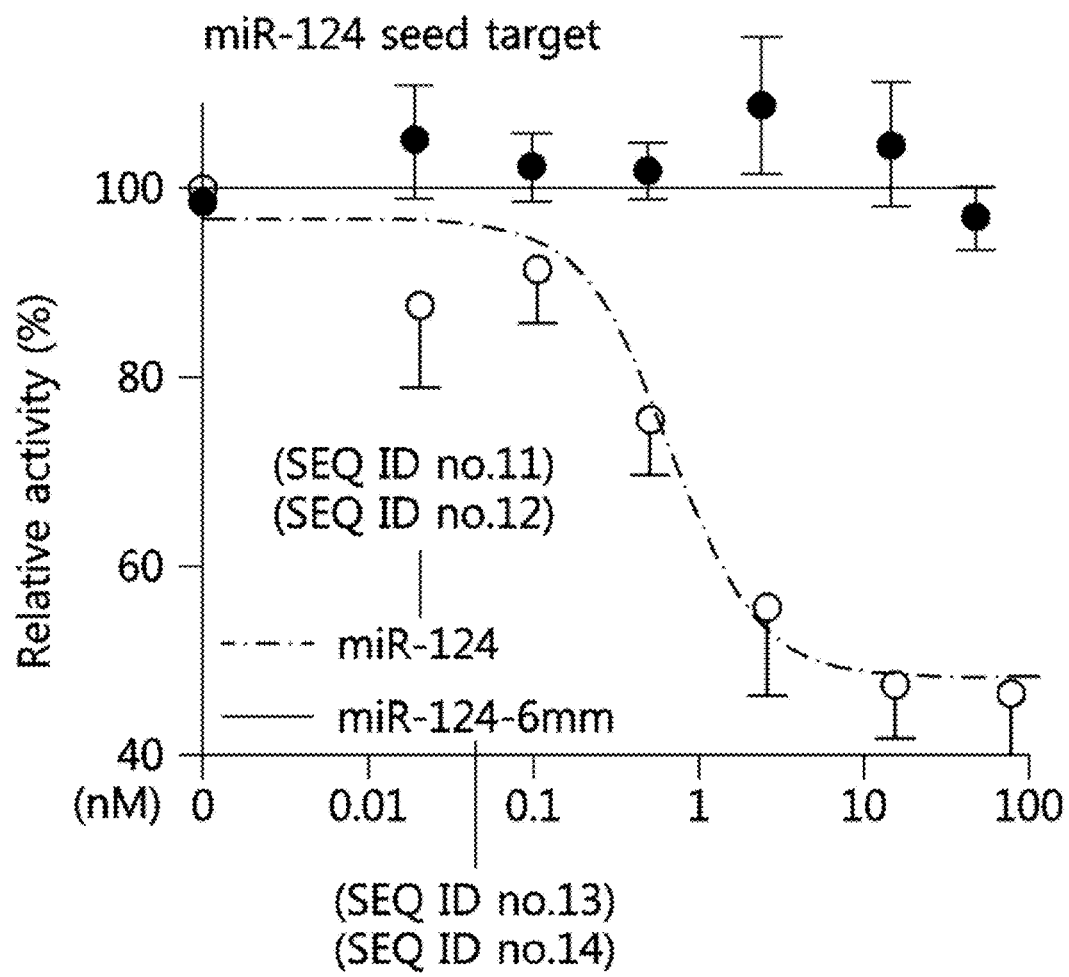
Figure 9E:
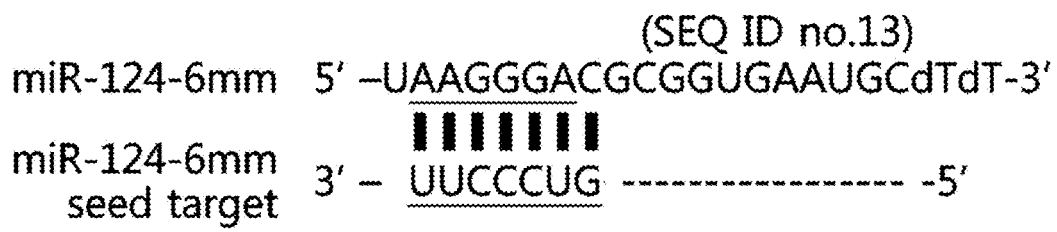
Figure 9F:
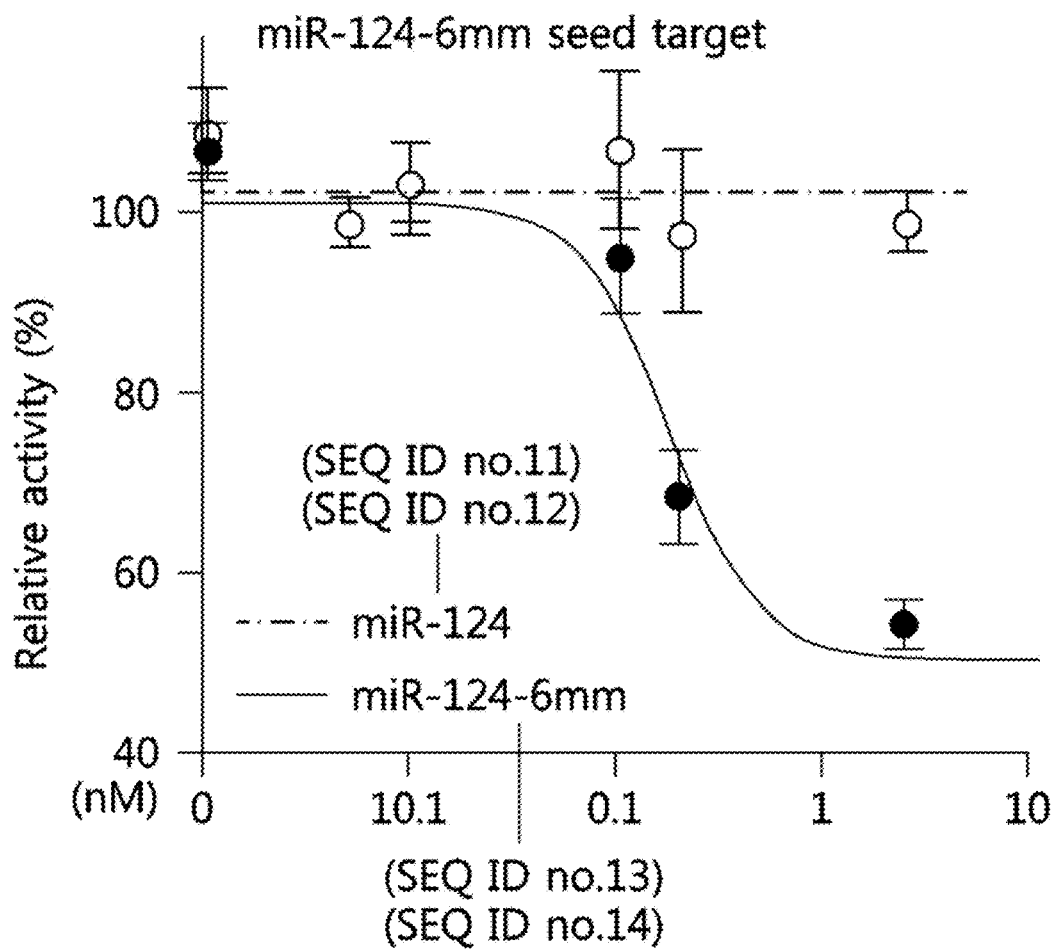

Nevertheless, the introduction of mismatch base-pairing can recognize new sequences as seed targets depending on changes in nucleotide base, thereby off-target effects can be produced by new sequence matches to the seed where the mismatch was introduced. Thus, when a mismatch was introduced to position 6 from the 5' end of miR-124, repression of a new sites which can interact with a new seed was examined by measuring IC50, wherein the new site can be recognized through consecutive base-pairings from positions 2-8 from the 5' end containing. As a result, as shown in FIGS. 9e and 9f, the new seed pairing target, which can be recognized through consecutive base-pairings from positions 2-8 from the 5' end, was silenced as much as observed in the unmodified miR-124.

Figure 9G:
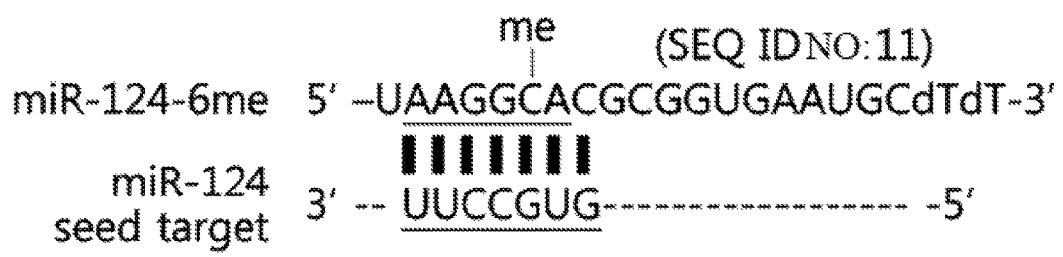
Figure 9H:
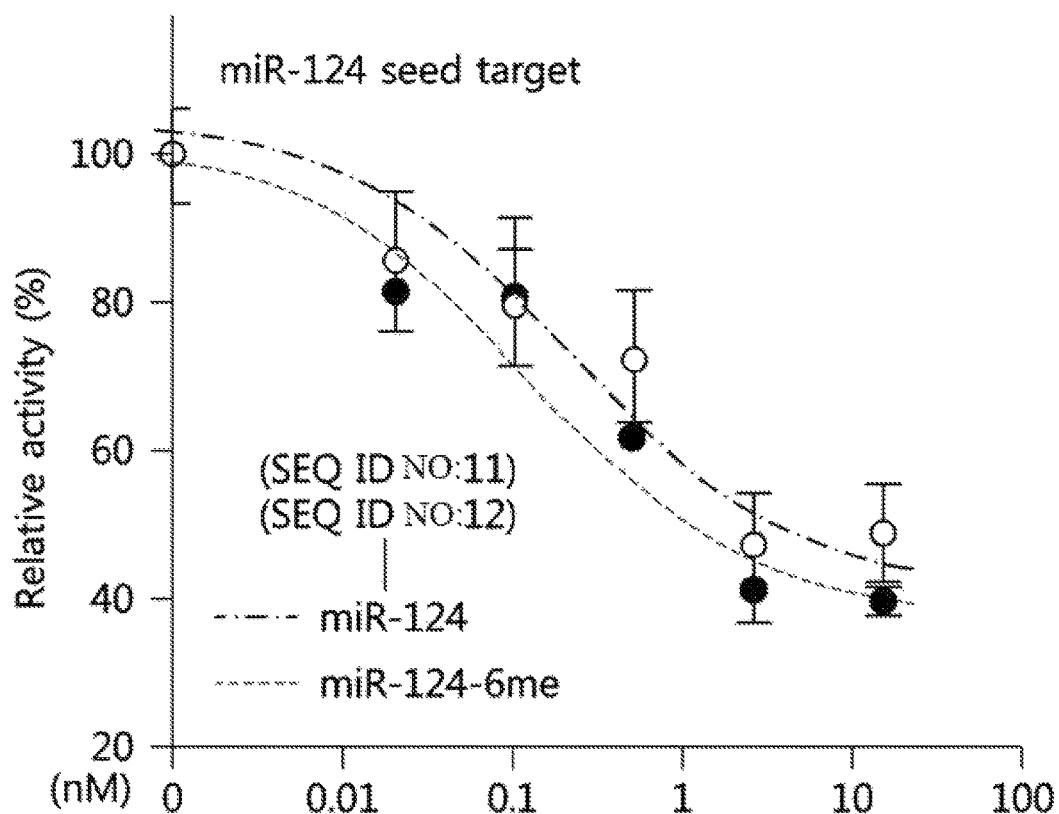

In addition, as shown in FIGS. 9g and 9h, conventional 2'OMe modification was applied to position 6 from the 5' end of miR-124, examined by IC50 measurement, wherein seed sites were still silenced as much as observed in the unmodified miR-124, wherein the seed sites could work as off-targets in the case of siRNA.

Based on the results above, it was confirmed that the method introducing a conventional mismatch to position 6 from the 5' end can prevent off-targets of initial seed pairing sites, but it has limitation that it causes off-targets of new seed pairing sites, altered by introducing the mismatch. Furthermore, the conventional 2'OMe modification cannot reduce off-targets at all when it is applied to position 6 from the 5' end.

Figure 9I:
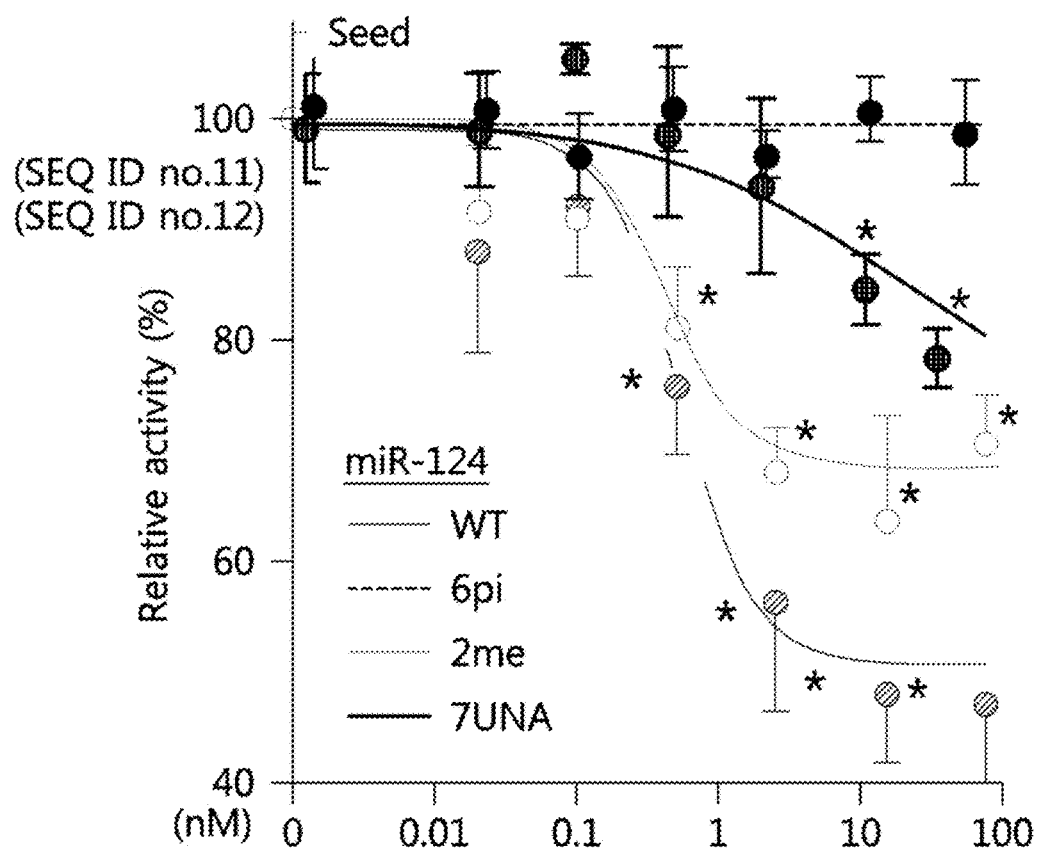

Next, for the comparison of other modifications, the 2'OMe modification in position 2 from the 5' end (2me) and the UNA modification in position 7 from 5' end (7UNA) were applied to miR-124, wherein their effects were measured by the same method performed in Example 1 above, wherein the other modifications were known to applied the position other than sixth nucleotide and effectively prevent off-targets. As a result, represented in FIG. 9i, both 2me (IC50=0.9 nM) and 7UNA (IC50=7.2 nM) were observed to only marginally reduce off-target effect compared with the unmodified miR-124 (IC50=0.7 nM), but the abasic deoxy nucleotide substitution of the present invention (6 pi) completely eliminated the off-target effect.

Figure 9J:
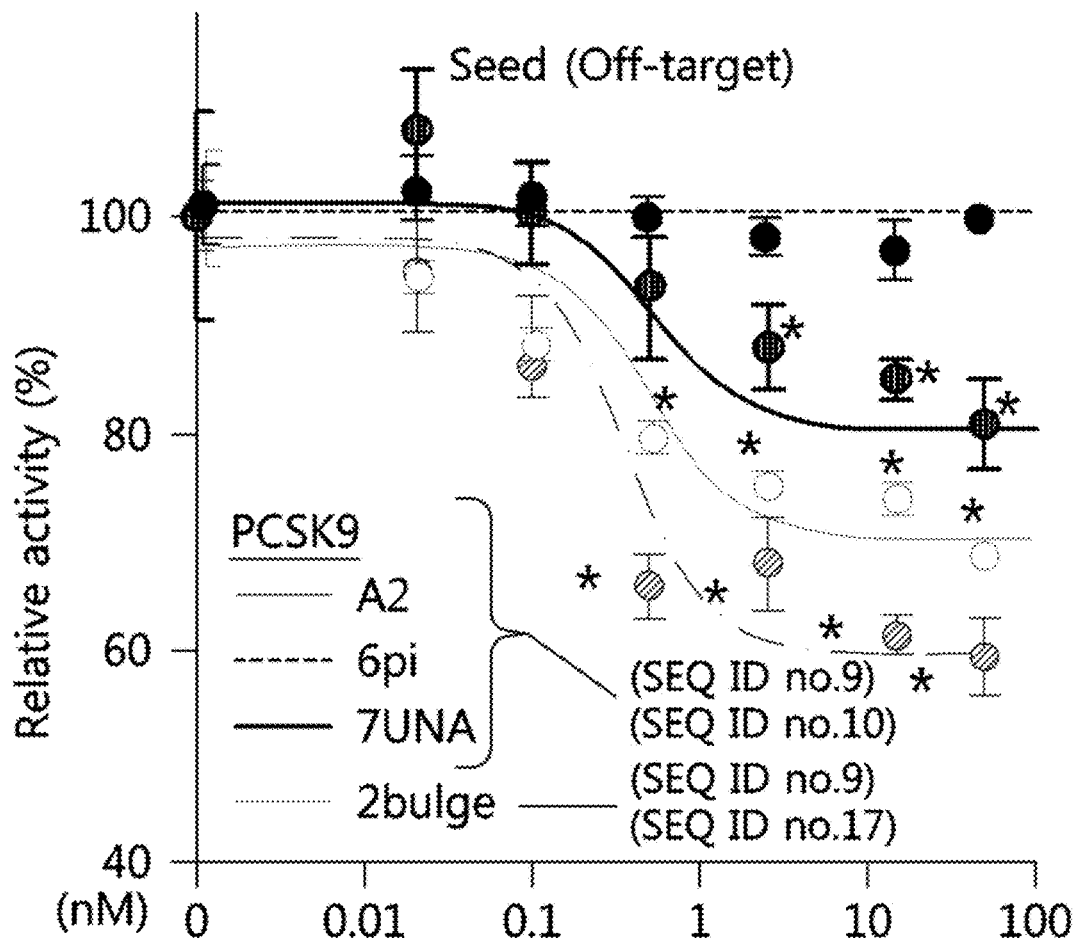

Furthermore, as shown in FIG. 9j, we observed that 7UNA applied to A2 (SEQ ID NO: 9) can reduce some off-target effects, but cannot completely abrogate it, wherein the A2 is the siRNA for silencing PCSK9 gene as on-target. Additionally, other method introducing a bulge was applied to A2 and examined for its effect, showing reduction of some off-target effects but not complete abrogation, wherein the method introducing a bulge was conventionally generated by changing a nucleotide to form single nucleotide bulge in position 2 from the 5' end of the guide strand in the siRNA duplex structure (SEQ ID NOS: 9 and 17).

Based on the above, it was confirmed that every conventional method with usage for inhibiting off-target effect can reduce some off-target effects, but has limitation that it cannot completely eliminate off-target effect, whereas the present invention completely abolish the off-target effects.

[Example 9] Comparison of Target Gene Silencing and Off-Target Effect for siRNA Molecules with No Base in Position 6 from the 5' End by C3 Substitution, Wherein the C3 Substitution Makes Covalent Bonding Between 5th and 7th Nucleotide Based on the observation in example 8, it is speculated that the reason to perform complete elimination of off-target effects by the siRNA-6 pi is that base in position 6 becomes unable to base-pair with off-targets through this region, wherein the siRNA-6 pi has substitution of position 6 from the 5' end to dSpacer (6 pi). Thus, in theory, any spacer modification making no base in position 6 from the 5' end is expected to eliminate off-target effect, wherein the spacer modification can be anything only if it can afford to be substituted to single nucleotide occupancy, although its backbone is not nucleotide.

Figure 10:
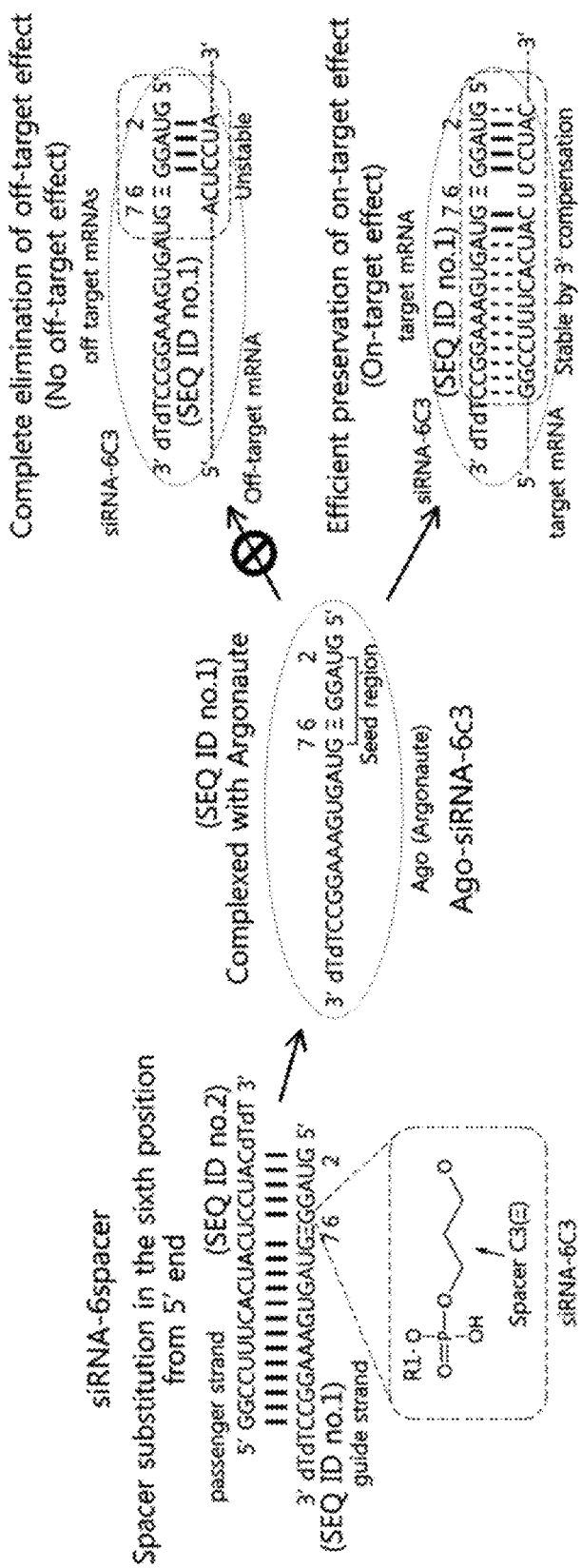
FIG. 10 shows a diagram for the single strand from the RNA interference-inducing nucleic acid, where the position 6 from the 5' end is substituted to a spacer, wherein the spacer is a hydrogen carbon chain comprising at least 3 carbons, alkyl group, affecting activity of repressing gene expression and suppressing miRNA-like off-target effects.

Therefore, as examples illustrated in FIG. 10, the present inventors expanded the spacer modification from dSpacer substitution of position 6 from the 5' end shown in FIG. 1 to covalent bonding, wherein the covalent bonding can be anything maintaining the abasic skeleton of position 6 from the 5' end, thus designing the most minimized spacer linking between 5th and 7th nucleotide. In other words, as the most minimized spacer occupying size of a nucleotide in position 6, C3 spacer, which comprises of phosphoryl group and three carbon molecules, was used for designing the modification. Using the C3 modification as the minimum standard of a spacer without nucleotide, a novel RNA interference-inducing nucleic acid has been invented, expecting complete elimination of off-target effect together with conservation of on-target efficiency as much as in abasic nucleotide substitution, wherein the modification is applied to position 6 from the 5' end.

Initially, as illustrated in FIG. 11a, the C3 spacer was adopted and applied to position 6 from the 5' end of miR-124 (SEQ NOS: 11 and 12) (miR-124-6c3), making covalent bonding between 5th and 7th nucleotide as shown in FIG. 11b, wherein IC50 was measured to investigate and compare the effect on on-target and off-target, wherein the C3 spacer is the most minimized spacer modification with covalent bonding and no base.

As a result, as shown in FIG. 11c, miR-124-6c3 (IC50=0.01 nM) was observed to show better efficiency of repressing the perfect match target than miR-124-6 pi (IC50=0.15 nM) and its efficiency of silencing the perfect match was the same as the unmodified miR-124 (IC50=0.01 nM), wherein the perfect match corresponds to siRNA on-target.

Figure 11D:
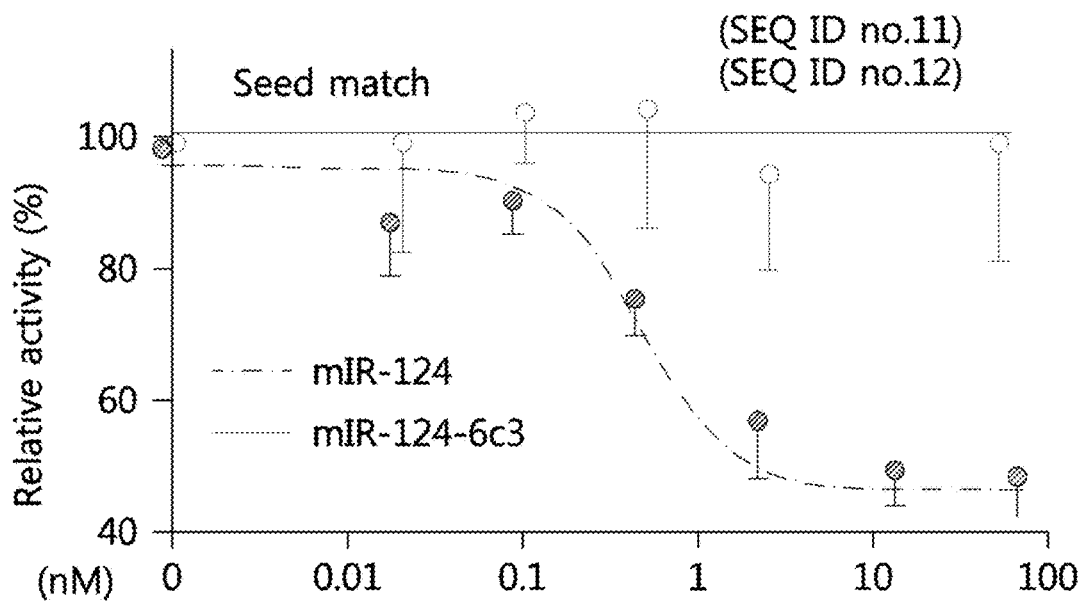
Figure 11E:
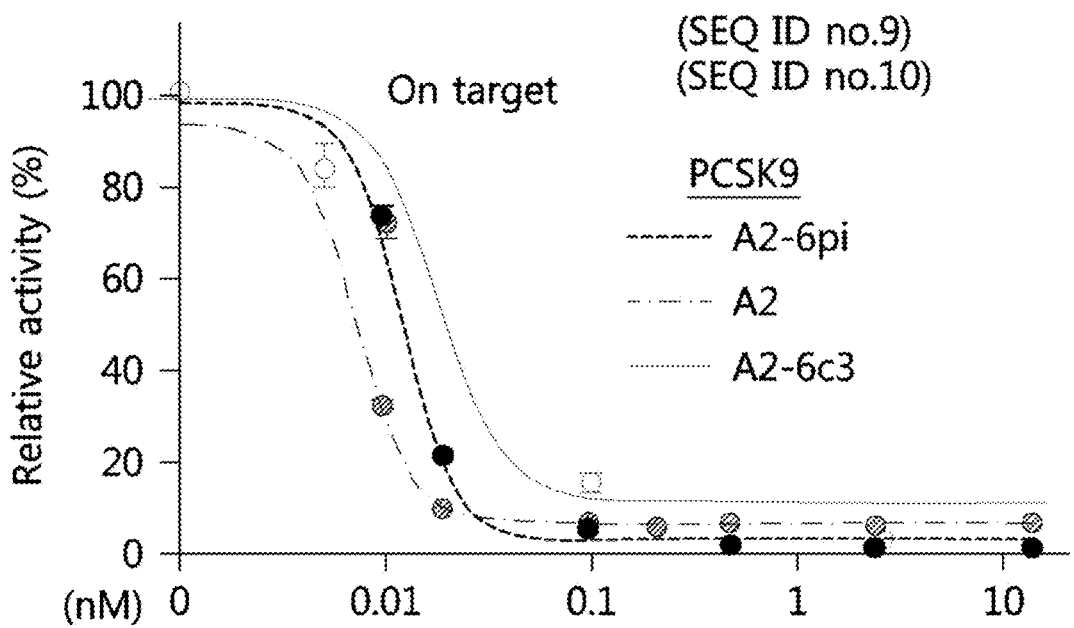
Figure 11F:
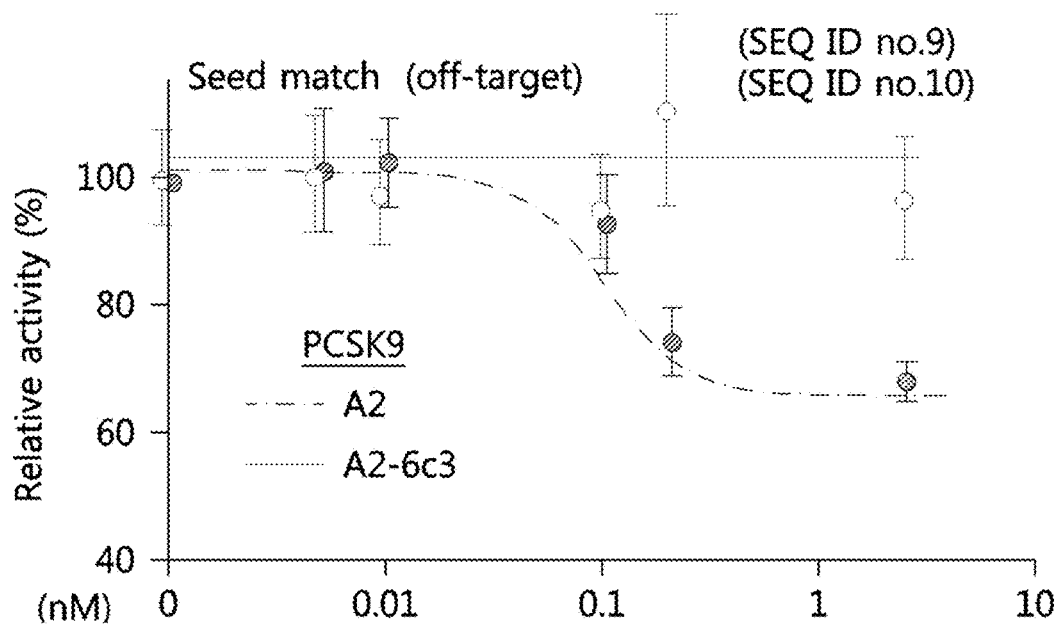
Figure 11G:
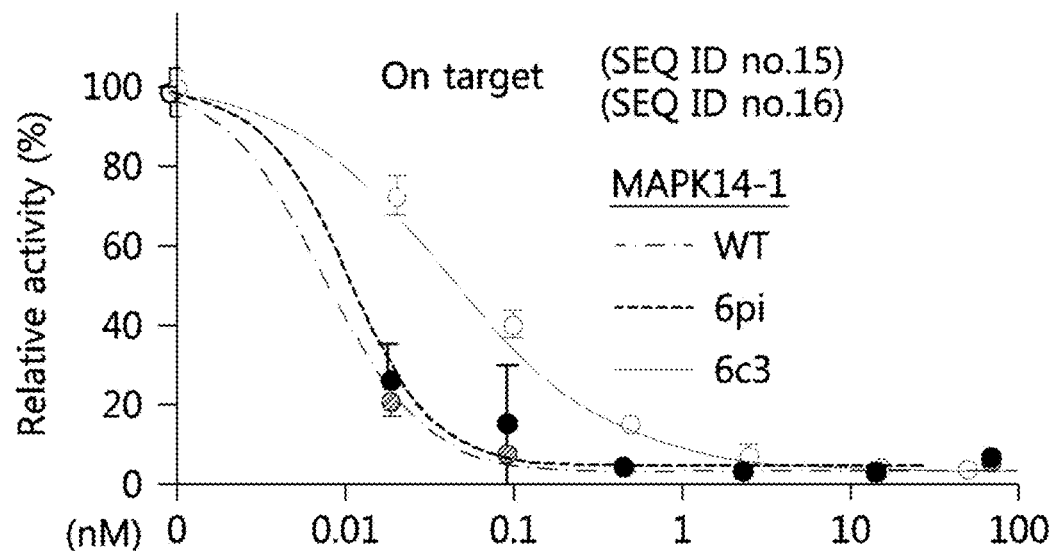
Figure 11H:
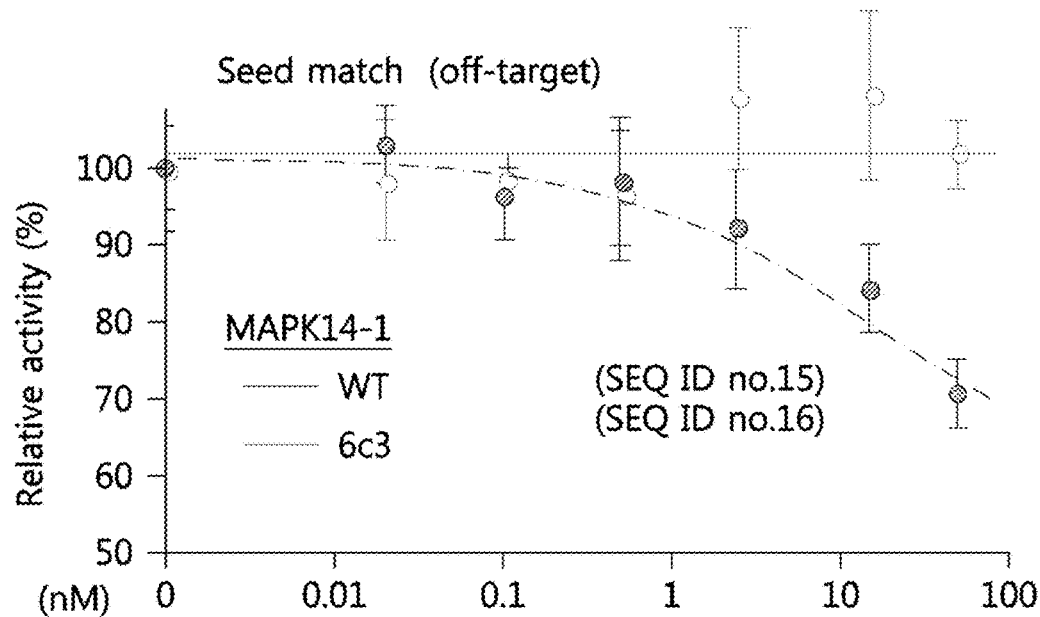
Figure 11I:
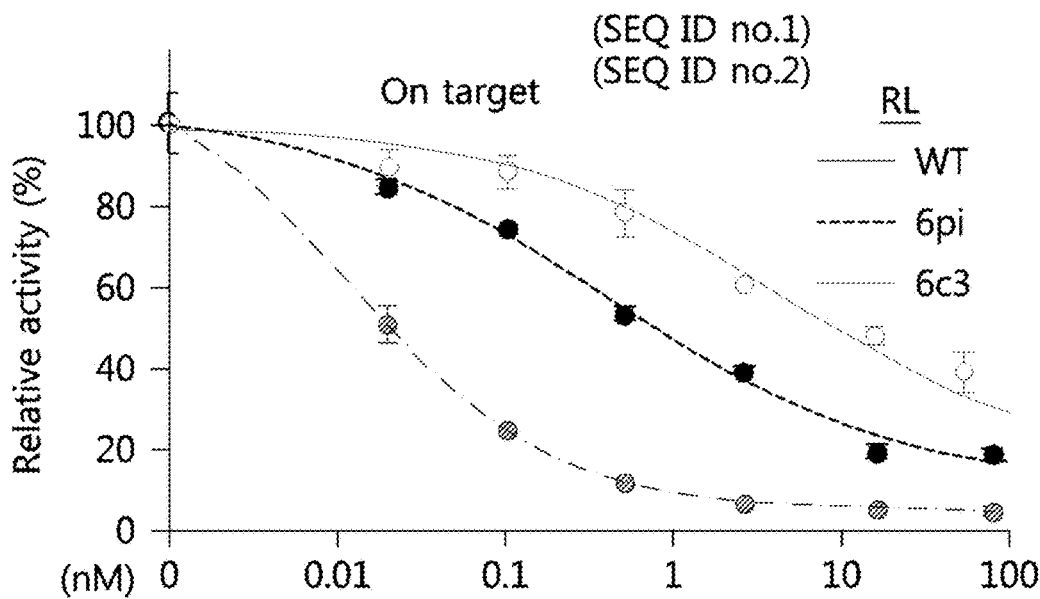
Figure 11J:
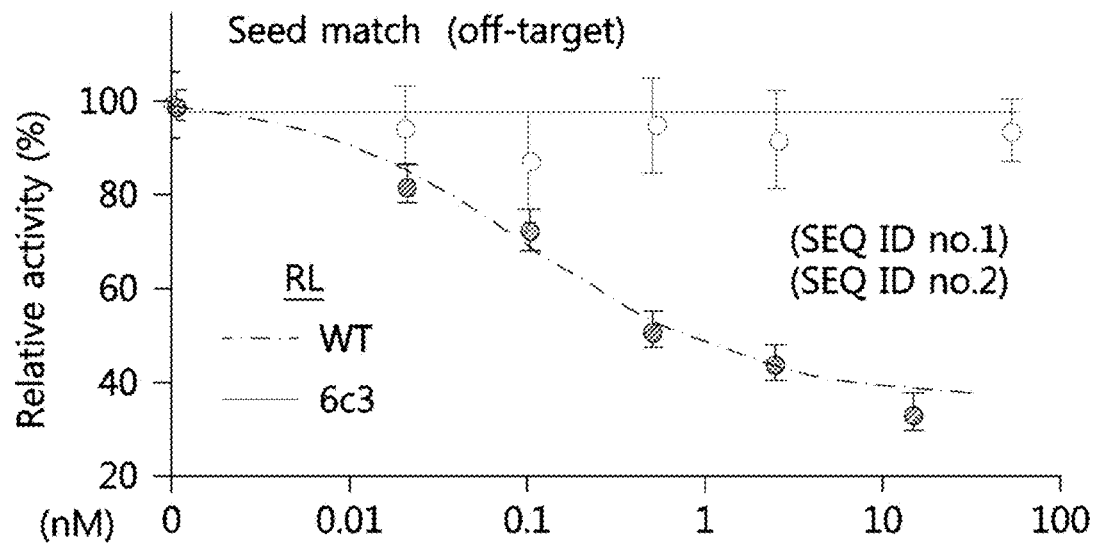

Furthermore, as shown in FIG. 11d, it was observed that silencing activity to seed pairing sites was completed disappeared when C3 was applied to position 6 from the 5' end of miR-124, wherein seed pairing sites mediate off-target effects in siRNA.

In addition, the C3 spacer was applied to position 6 from the 5' end of A2 (SEQ ID NO: 9); siRNA for silencing PCSK9 gene, siMAPK14-1 (SEQ ID NO: 15); siRNA for silencing MAPK14 gene (Jackson, A. L., et al., Rna, 12(7): 1179), or siRL, showing superior on-target activity together with complete abrogation of off-target effect in every case, wherein the results were validated by measuring IC50 as represented in FIGS. 11e, 11f, 11g, 11h, 11i and 11j.

Based on the statement above, we found the C3 spacer which is minimal abasic form in position 6, existing as covalent bonding between 5th and 7th nucleotide in siRNA, wherein the C3 spacer allows the backbone without nucleotide, wherein the spacer can be any covalent bonding only if its size is affordable to be substituted to a single nucleotide occupancy, thereby completely abrogating off-target repression while conserving the better or the same efficiency of on-target silencing from 6 pi.

[Example 10] Evaluation of the Effect from the Spacer Substation in Position 1-2 from the 3' End of siRNA Molecules on miRNA-Like Off-Targets Mediated by 3' End Compensatory Pairing and On-Target Gene Silencing The off-target effect caused by siRNA is majorly mediated by recognizing target genes like miR NA through base-pairing with the seed region in sequence dependent manner. In the case that miRNA recognizes targets in vivo, it is reported that miRNAs repress target genes through compensatory pairings within the 3' end region (3'-compensatory pairing) when the binding between seed region and target becomes weak (Cell. 2009; 136:215-233). Accordingly, miRNA-like off-target effect could be occurred by the mechanism of the 3'-compensatory pairing, requiring the method to prevent it.

Figure 12:
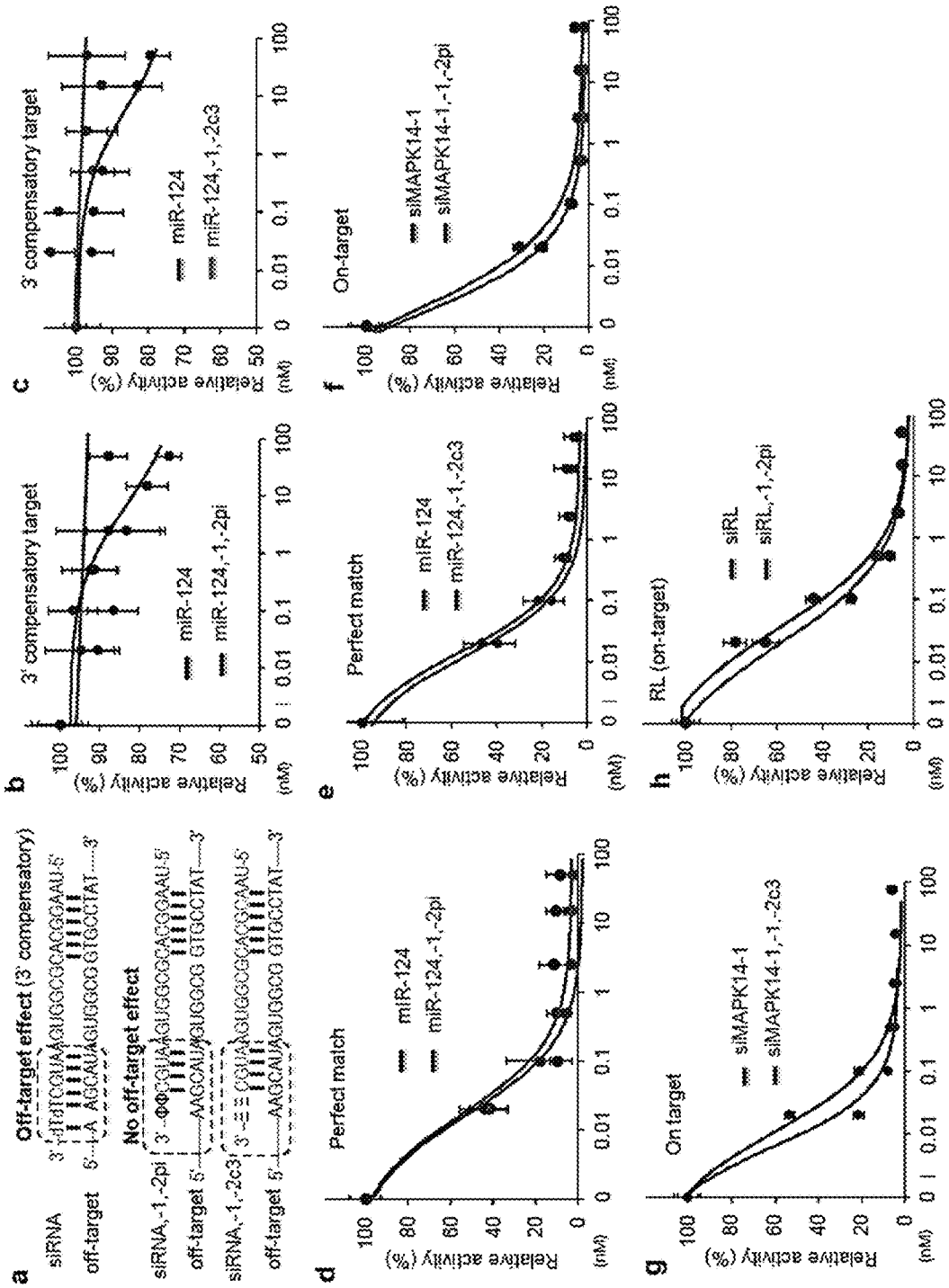
FIG. 12a, 12b, 12c, 12d, 12e, 12f, 12g and 12h represents the results for the modified siRNA of which positions 1-2 from the 3' end are substituted to the spacer, wherein activity of repressing gene expression and miRNA-like off-target effects mediated by 3'-compensatory pairing are evaluated.

Conventional siRNAs generally contain deoxynucleotide thymidine (dT) in positions 1-2 from the 3' end, forming overhang structure in the double-stranded siRNAs. In the case of dT, since it can base-pair to adenosine (A), it could participate in 3'-compensatory pairing and induce miRNA-like off-target effect. Therefore, in order to block the off-target effect mediated by such 3'-compensatory pairing, spacer substitution modification can be applied to positions 1-2 from the 3' end as illustrated in FIG. 12a. In other words, the present inventors gave attention to the fact that conventional double-stranded siRNA structure can be maintained even in the case of applying dSpacer of C3 spacer to positions 1-2 from the 3' end, making them as abasic nucleotide spacer, wherein efficiency of on-target activity can be maintained as superior, but off-target effects mediated by 3'-compensatory pairing can be eliminated, thereby invented the present RNA interference-inducing nucleic acids.

For this, after substituting positions 1-2 from the 3' end of miR-124 (SEQ ID NOS: 11 and 12) to abasic spacer modification, the on-target effect and off-target effect mediated by 3'-compensatory pairing were investigated by measuring IC50 using the same method in FIG. 8 above. As a result represented in FIG. 12b or FIG. 12c, we observed that the unmodified miR-124 showed target repression mediated by 3'-compensatory pairing like siRNA off-target silencing, but such off-target effects were completely disappeared when 1st and 2nd nucleotides from the 3' end were substituted to either dSpacer or C3 spacer.

Like this, when the first and second nucleotides from the 3' end of double-stranded miR-124 were substituted to abasic spacer, such as dSpacer (pi) or C3 spacer (IC50=0.02 nM), the same on-target silencing effect was observed as in the unmodified miR-124 (IC50=0.02 nM), wherein the on-target silencing effect was examined by using perfect complementary pairing target, on-target in siRNA, as represented in FIGS. 12d and 12e.

Additionally, when pi or c3 was applied as a spacer to position 1-2 from the 3' end of siMAP14-1 (SEQ ID NOS: 15 and 16) or siRL (SEQ ID NOS: 1 and 2), the same on-target repression activity was observed as in the unmodified, as represented in FIGS. 12f and 12h.

Based on the results above, it was confirmed that the RNA interference-inducing nucleic acids, of which 1st and 2nd nucleotides from the 3' end were substituted to abasic spacer with covalent bonds, have activity to avoid off-target effect mediated by 3'-compensatory pairing while maintaining the activity of silencing the target gene.

Although the preferred embodiments of the present invention have been disclosed for illustrative purposes, one skilled in the art will appreciate that various modifications, additions and substitutions are possible, without departing from the scope and spirit of the invention. Therefore, it should be understood that the above-described embodiments are illustrative but not restrictive in all aspects.

INDUSTRIAL APPLICABILITY

According to the present invention, the RNA interference-inducing nucleic acid provides a novel modified form, showing target selectivity and specificity by abrogating off-target effects and also maintaining activity of silencing target gene expression, wherein the off-target problem, which causes inaccuracy and adverse side effects in the usage of conventional RNA interference, can be solved by offering such RNA interference-inducing nucleic acids, thereby it can be widely used as a method for silencing gene expression for research and for gene therapy without concerning.

What is claim is:

1. An RNA interference-inducing nucleic acid molecule comprising at least one nucleic acid strand, the at least one nucleic acid strand comprising a modification at the sixth position from the 5' end of the nucleic acid strand, and optional further modifications at each of the first and second position from the 3' end of the nucleic acid strand,
wherein each modification is a replacement of a nucleotide residue at the position with a spacer,
wherein the spacer is selected from the group consisting of an abasic deoxyribonucleotide analog which does not include a nucleobase, and a C3 alkyl group.

2. The RNA interference-inducing nucleic acid molecule of claim 1, wherein the at least one nucleic acid strand is capable of binding to argonaute protein and inducing RNA interference.

3. The RNA interference-inducing nucleic acid molecule of claim 1, wherein the nucleic acid strand further comprises a mismatch base pairing with an RNA of a target gene by a substitution or a bulge by an insertion.

4. The RNA interference-inducing nucleic acid molecule of claim 1, which is selected from the group consisting of siRNA, miRNA, shRNA, DsiRNA, siRNA, ss-siRNA, piRNA, endo-siRNA and asiRNA.

5. A gene silencing composition comprising the RNA interference-inducing nucleic acid molecule of claim 1.

6. A gene silencing kit comprising the RNA interference-inducing nucleic acid molecule of claim 1.

7. A method for silencing a target gene in a cell, the method comprising a step of introducing the RNA interference-inducing nucleic acid molecule of claim 1 into the cell.

8. A method for suppressing off-target effects mediated by a guide strand of the RNA interference-inducing nucleic acid molecule of claim 1, the method comprising a step of introducing the RNA interference-inducing nucleic acid molecule into a cell,
wherein the at least one nucleic acid strand, which comprises the modification, of claim 1 is the guide strand.

9. A method for suppressing off-target effects mediated by a passenger strand of the RNA interference-inducing nucleic acid molecule of claim 1, the method comprising a step of introducing the RNA interference-inducing nucleic acid molecule into a cell,
wherein the at least one nucleic acid strand, which comprises the modification, of claim 1 is the passenger strand.

10. The RNA interference-inducing nucleic acid molecule of claim 1 further comprising a chemical modification.

11. The RNA interference-inducing nucleic acid molecule of claim 1, wherein the at least one nucleic acid strand comprises the optional further modifications.

12. The gene silencing composition of claim 5, wherein the at least one nucleic acid strand comprises the optional further modifications.

13. The gene silencing composition of claim 6, wherein the at least one nucleic acid strand comprises the optional further modifications.

14. The method of claim 7, wherein the at least one nucleic acid strand comprises the optional further modifications.

15. The method of claim 8, wherein the at least one nucleic acid strand comprises the optional further modifications.

16. The method of claim 9, wherein the at least one nucleic acid strand comprises the optional further modifications.

* * * * *

SEQUENCE LISTING

```
<160> NUMBER OF SEQ ID NOS: 17

<210> SEQ ID NO 1
<211> LENGTH: 21
<212> TYPE: RNA
<213> ORGANISM: Artificial Sequence
<220> FEATURE:
<223> OTHER INFORMATION: siRL Guide
<220> FEATURE:
<221> NAME/KEY: modified_base
<222> LOCATION: (1)
<223> OTHER INFORMATION: n = guanosine or abasic deoxyribonucleotide
<220> FEATURE:
<221> NAME/KEY: modified_base
<222> LOCATION: (2)
<223> OTHER INFORMATION: n = uridine, abasic deoxyribonucleotide,
    abasic ribonucleotide, or 2'-O-methyluridine
<220> FEATURE:
<221> NAME/KEY: modified_base
<222> LOCATION: (3)
<223> OTHER INFORMATION: n = adenosine, abasic deoxyribonucleotide, or
    abasic ribonucleotide
<220> FEATURE:
<221> NAME/KEY: modified_base
<222> LOCATION: (4)
<223> OTHER INFORMATION: n = guanosine, abasic deoxyribonucleotide, or
    abasic ribonucleotide
<220> FEATURE:
<221> NAME/KEY: modified_base
<222> LOCATION: (5)
<223> OTHER INFORMATION: n = guanosine, abasic deoxyribonucleotide, or
    abasic ribonucleotide
<220> FEATURE:
<221> NAME/KEY: modified_base
<222> LOCATION: (6)
<223> OTHER INFORMATION: n = adenosine, abasic deoxyribonucleotide,
    abasic ribonucleotide, or propyl spacer
```

```
<220> FEATURE:
<221> NAME/KEY: modified_base
<222> LOCATION: (7)
<223> OTHER INFORMATION: n = guanosine, abasic deoxyribonucleotide, or
      abasic ribonucleotide
<220> FEATURE:
<221> NAME/KEY: modified_base
<222> LOCATION: (8)
<223> OTHER INFORMATION: n = uridine or abasic deoxyribonucleotide
<220> FEATURE:
<221> NAME/KEY: modified_base
<222> LOCATION: (9)
<223> OTHER INFORMATION: n = adenosine or abasic deoxyribonucleotide
<220> FEATURE:
<221> NAME/KEY: modified_base
<222> LOCATION: (10)
<223> OTHER INFORMATION: n = guanosine or abasic deoxyribonucleotide
<220> FEATURE:
<221> NAME/KEY: modified_base
<222> LOCATION: (11)
<223> OTHER INFORMATION: n = uridine or abasic deoxyribonucleotide
<220> FEATURE:
<221> NAME/KEY: modified_base
<222> LOCATION: (20)
<223> OTHER INFORMATION: n = deoxythymidine
<220> FEATURE:
<221> NAME/KEY: modified_base
<222> LOCATION: (21)
<223> OTHER INFORMATION: n = deoxythymidine

<400> SEQUENCE: 1
nnnnnnnnnn ngaaaggccn n                                                    21

<210> SEQ ID NO 2
<211> LENGTH: 21
<212> TYPE: RNA
<213> ORGANISM: Artificial Sequence
<220> FEATURE:
<223> OTHER INFORMATION: siRL Passenger
<220> FEATURE:
<221> NAME/KEY: modified_base
<222> LOCATION: (20)
<223> OTHER INFORMATION: n = deoxythymidine
<220> FEATURE:
<221> NAME/KEY: modified_base
<222> LOCATION: (21)
<223> OTHER INFORMATION: n = deoxythymidine

<400> SEQUENCE: 2
ggccuuucac uacuccuacn n                                                    21

<210> SEQ ID NO 3
<211> LENGTH: 24
<212> TYPE: RNA
<213> ORGANISM: Artificial Sequence
<220> FEATURE:
<223> OTHER INFORMATION: NT Guide
<220> FEATURE:
<221> NAME/KEY: modified_base
<222> LOCATION: (1)
<223> OTHER INFORMATION: n = 2'-O-methyluridine
<220> FEATURE:
<221> NAME/KEY: modified_base
<222> LOCATION: (2)
<223> OTHER INFORMATION: n = 2'-O-methyladenosin
<220> FEATURE:
<221> NAME/KEY: modified_base
<222> LOCATION: (23)
<223> OTHER INFORMATION: n = deoxythymidine
<220> FEATURE:
<221> NAME/KEY: modified_base
<222> LOCATION: (24)
<223> OTHER INFORMATION: n = deoxythymidine
```

```
<400> SEQUENCE: 3
nncucuuucu aggagguugu gann                                          24

<210> SEQ ID NO 4
<211> LENGTH: 24
<212> TYPE: RNA
<213> ORGANISM: Artificial Sequence
<220> FEATURE:
<223> OTHER INFORMATION: NT Passenger
<220> FEATURE:
<221> NAME/KEY: modified_base
<222> LOCATION: (1)
<223> OTHER INFORMATION: n = 2'-O-methyluridine
<220> FEATURE:
<221> NAME/KEY: modified_base
<222> LOCATION: (2)
<223> OTHER INFORMATION: n = 2'-O-methylcytidine
<220> FEATURE:
<221> NAME/KEY: modified_base
<222> LOCATION: (23)
<223> OTHER INFORMATION: n = deoxythymidine
<220> FEATURE:
<221> NAME/KEY: modified_base
<222> LOCATION: (24)
<223> OTHER INFORMATION: n = deoxythymidine

<400> SEQUENCE: 4
nnacaaccuc cuagaaagag uann                                          24

<210> SEQ ID NO 5
<211> LENGTH: 20
<212> TYPE: RNA
<213> ORGANISM: Artificial Sequence
<220> FEATURE:
<223> OTHER INFORMATION: miR-124-3p
<220> FEATURE:
<221> NAME/KEY: modified_base
<222> LOCATION: (6)
<223> OTHER INFORMATION: n = cytidine or abasic deoxyribonucleotide

<400> SEQUENCE: 5
uaaggnacgc ggugaaugcc                                               20

<210> SEQ ID NO 6
<211> LENGTH: 22
<212> TYPE: RNA
<213> ORGANISM: Artificial Sequence
<220> FEATURE:
<223> OTHER INFORMATION: miR-124-5p

<400> SEQUENCE: 6
cguguucaca gcggaccuug au                                            22

<210> SEQ ID NO 7
<211> LENGTH: 21
<212> TYPE: RNA
<213> ORGANISM: Artificial Sequence
<220> FEATURE:
<223> OTHER INFORMATION: siRNAs for PCSK9 A1 giude
<220> FEATURE:
<221> NAME/KEY: modified_base
<222> LOCATION: (2)
<223> OTHER INFORMATION: n = uridine or abasic deoxyribonucleotide
<220> FEATURE:
<221> NAME/KEY: modified_base
<222> LOCATION: (3)
<223> OTHER INFORMATION: n = cytidine or abasic deoxyribonucleotide
<220> FEATURE:
<221> NAME/KEY: modified_base
<222> LOCATION: (4)
<223> OTHER INFORMATION: n = cytidine or abasic deoxyribonucleotide
```

```
<220> FEATURE:
<221> NAME/KEY: modified_base
<222> LOCATION: (5)
<223> OTHER INFORMATION: n = guanosine or abasic deoxyribonucleotide
<220> FEATURE:
<221> NAME/KEY: modified_base
<222> LOCATION: (6)
<223> OTHER INFORMATION: n = adenosine or abasic deoxyribonucleotide
<220> FEATURE:
<221> NAME/KEY: modified_base
<222> LOCATION: (20)
<223> OTHER INFORMATION: n = deoxythymidine
<220> FEATURE:
<221> NAME/KEY: modified_base
<222> LOCATION: (21)
<223> OTHER INFORMATION: n = deoxythymidine

<400> SEQUENCE: 7
unnnnnauaa acuccaggcn n                                               21

<210> SEQ ID NO 8
<211> LENGTH: 21
<212> TYPE: RNA
<213> ORGANISM: Artificial Sequence
<220> FEATURE:
<223> OTHER INFORMATION: siRNAs for PCSK9 A1 passenger
<220> FEATURE:
<221> NAME/KEY: modified_base
<222> LOCATION: (20)
<223> OTHER INFORMATION: n = deoxythymidine
<220> FEATURE:
<221> NAME/KEY: modified_base
<222> LOCATION: (21)
<223> OTHER INFORMATION: n = deoxythymidine

<400> SEQUENCE: 8
gccuggaguu uauucggaan n                                               21

<210> SEQ ID NO 9
<211> LENGTH: 21
<212> TYPE: RNA
<213> ORGANISM: Artificial Sequence
<220> FEATURE:
<223> OTHER INFORMATION: siRNAs for PCSK9 A2 guide
<220> FEATURE:
<221> NAME/KEY: modified_base
<222> LOCATION: (6)
<223> OTHER INFORMATION: n = adenosine, abasic deoxyribonucleotide or
      propyl spacer
<220> FEATURE:
<221> NAME/KEY: modified_base
<222> LOCATION: (7)
<223> OTHER INFORMATION: n = adenosine or adenine unlocked nucleic acid
<220> FEATURE:
<221> NAME/KEY: modified_base
<222> LOCATION: (8)
<223> OTHER INFORMATION: n = 2'-O-methyluridine
<220> FEATURE:
<221> NAME/KEY: modified_base
<222> LOCATION: (15)
<223> OTHER INFORMATION: n = 2'-O-methylcytidine
<220> FEATURE:
<221> NAME/KEY: modified_base
<222> LOCATION: (20)
<223> OTHER INFORMATION: n = deoxythymidine
<220> FEATURE:
<221> NAME/KEY: modified_base
<222> LOCATION: (21)
<223> OTHER INFORMATION: n = deoxythymidine

<400> SEQUENCE: 9
uuccgnnnaa acucnaggcn n                                               21
```

```
<210> SEQ ID NO 10
<211> LENGTH: 21
<212> TYPE: RNA
<213> ORGANISM: Artificial Sequence
<220> FEATURE:
<223> OTHER INFORMATION: siRNAs for PCSK9 A2 passenger
<220> FEATURE:
<221> NAME/KEY: modified_base
<222> LOCATION: (2)
<223> OTHER INFORMATION: n = 2'-O-methylcytidine
<220> FEATURE:
<221> NAME/KEY: modified_base
<222> LOCATION: (3)
<223> OTHER INFORMATION: n = 2'-O-methylcytidine
<220> FEATURE:
<221> NAME/KEY: modified_base
<222> LOCATION: (4)
<223> OTHER INFORMATION: n = 2'-O-methyluridine
<220> FEATURE:
<221> NAME/KEY: modified_base
<222> LOCATION: (9)
<223> OTHER INFORMATION: n = 2'-O-methyluridine
<220> FEATURE:
<221> NAME/KEY: modified_base
<222> LOCATION: (10)
<223> OTHER INFORMATION: n = 2'-O-methyluridine
<220> FEATURE:
<221> NAME/KEY: modified_base
<222> LOCATION: (11)
<223> OTHER INFORMATION: n = 2'-O-methyluridine
<220> FEATURE:
<221> NAME/KEY: modified_base
<222> LOCATION: (13)
<223> OTHER INFORMATION: n = 2'-O-methyluridine
<220> FEATURE:
<221> NAME/KEY: modified_base
<222> LOCATION: (14)
<223> OTHER INFORMATION: n = 2'-O-methyluridine
<220> FEATURE:
<221> NAME/KEY: modified_base
<222> LOCATION: (15)
<223> OTHER INFORMATION: n = 2'-O-methylcytidine
<220> FEATURE:
<221> NAME/KEY: modified_base
<222> LOCATION: (20)
<223> OTHER INFORMATION: n = deoxythymidine
<220> FEATURE:
<221> NAME/KEY: modified_base
<222> LOCATION: (21)
<223> OTHER INFORMATION: n = deoxythymidine

<400> SEQUENCE: 10
gnnnggagnn nannnggaan n                                              21

<210> SEQ ID NO 11
<211> LENGTH: 21
<212> TYPE: RNA
<213> ORGANISM: Artificial Sequence
<220> FEATURE:
<223> OTHER INFORMATION: miR-124 Guide
<220> FEATURE:
<221> NAME/KEY: modified_base
<222> LOCATION: (2)
<223> OTHER INFORMATION: n = adenosine or 2'-O-methyadenosine
<220> FEATURE:
<221> NAME/KEY: modified_base
<222> LOCATION: (6)
<223> OTHER INFORMATION: n = cytidine, 2'-O-methycytidine,
      abasic deoxyribonucleotide, or propyl spacer
<220> FEATURE:
<221> NAME/KEY: modified_base
<222> LOCATION: (7)
<223> OTHER INFORMATION: n = adenosine or adenine unlocked nucleic acid
<220> FEATURE:
<221> NAME/KEY: modified_base
<222> LOCATION: (20)
<223> OTHER INFORMATION: n = deoxythymidine
```

<220> FEATURE:
<221> NAME/KEY: modified_base
<222> LOCATION: (21)
<223> OTHER INFORMATION: n = deoxythymidine

<400> SEQUENCE: 11
unaggnncgc ggugaaugcn n    21

<210> SEQ ID NO 12
<211> LENGTH: 21
<212> TYPE: RNA
<213> ORGANISM: Artificial Sequence
<220> FEATURE:
<223> OTHER INFORMATION: miR-124 Passenger
<220> FEATURE:
<221> NAME/KEY: modified_base
<222> LOCATION: (20)
<223> OTHER INFORMATION: n = deoxythymidine
<220> FEATURE:
<221> NAME/KEY: modified_base
<222> LOCATION: (21)
<223> OTHER INFORMATION: n = deoxythymidine

<400> SEQUENCE: 12
gcauucaccg cgugccuuan n    21

<210> SEQ ID NO 13
<211> LENGTH: 21
<212> TYPE: RNA
<213> ORGANISM: Artificial Sequence
<220> FEATURE:
<223> OTHER INFORMATION: miR-124 6mm Guide
<220> FEATURE:
<221> NAME/KEY: modified_base
<222> LOCATION: (20)
<223> OTHER INFORMATION: n = deoxythymidine
<220> FEATURE:
<221> NAME/KEY: modified_base
<222> LOCATION: (21)
<223> OTHER INFORMATION: n = deoxythymidine

<400> SEQUENCE: 13
uaagggacgc ggugaaugcn n    21

<210> SEQ ID NO 14
<211> LENGTH: 21
<212> TYPE: RNA
<213> ORGANISM: Artificial Sequence
<220> FEATURE:
<223> OTHER INFORMATION: miR-124 6mm Passenger
<220> FEATURE:
<221> NAME/KEY: modified_base
<222> LOCATION: (20)
<223> OTHER INFORMATION: n = deoxythymidine
<220> FEATURE:
<221> NAME/KEY: modified_base
<222> LOCATION: (21)
<223> OTHER INFORMATION: n = deoxythymidine

<400> SEQUENCE: 14
gcauucaccg cgucccuuan n    21

<210> SEQ ID NO 15
<211> LENGTH: 21
<212> TYPE: RNA
<213> ORGANISM: Artificial Sequence
<220> FEATURE:
<223> OTHER INFORMATION: siRNA for MAPK14-1 Guide

```
<220> FEATURE:
<221> NAME/KEY: modified_base
<222> LOCATION: (6)
<223> OTHER INFORMATION: n = cytidine, abasic deoxyribonucleotide, or
      propyl spacer
<220> FEATURE:
<221> NAME/KEY: modified_base
<222> LOCATION: (20)
<223> OTHER INFORMATION: n = deoxythymidine
<220> FEATURE:
<221> NAME/KEY: modified_base
<222> LOCATION: (21)
<223> OTHER INFORMATION: n = deoxythymidine

<400> SEQUENCE: 15
aaccgnaguu cucguaggn n                                                    21

<210> SEQ ID NO 16
<211> LENGTH: 21
<212> TYPE: RNA
<213> ORGANISM: Artificial Sequence
<220> FEATURE:
<223> OTHER INFORMATION: siRNA for MAPK14-1 Passenger
<220> FEATURE:
<221> NAME/KEY: modified_base
<222> LOCATION: (20)
<223> OTHER INFORMATION: n = deoxythymidine
<220> FEATURE:
<221> NAME/KEY: modified_base
<222> LOCATION: (21)
<223> OTHER INFORMATION: n = deoxythymidine

<400> SEQUENCE: 16
ccuacagaga acugcgguun n                                                   21

<210> SEQ ID NO 17
<211> LENGTH: 20
<212> TYPE: RNA
<213> ORGANISM: Artificial Sequence
<220> FEATURE:
<223> OTHER INFORMATION: A2 2bulge
<220> FEATURE:
<221> NAME/KEY: modified_base
<222> LOCATION: (2)
<223> OTHER INFORMATION: n = 2'-O-methylcytidine
<220> FEATURE:
<221> NAME/KEY: modified_base
<222> LOCATION: (3)
<223> OTHER INFORMATION: n = 2'-O-methylcytidine
<220> FEATURE:
<221> NAME/KEY: modified_base
<222> LOCATION: (4)
<223> OTHER INFORMATION: n = 2'-O-methyluridine
<220> FEATURE:
<221> NAME/KEY: modified_base
<222> LOCATION: (9)
<223> OTHER INFORMATION: n = 2'-O-methyluridine
<220> FEATURE:
<221> NAME/KEY: modified_base
<222> LOCATION: (10)
<223> OTHER INFORMATION: n = 2'-O-methyluridine
<220> FEATURE:
<221> NAME/KEY: modified_base
<222> LOCATION: (11)
<223> OTHER INFORMATION: n = 2'-O-methyluridine
<220> FEATURE:
<221> NAME/KEY: modified_base
<222> LOCATION: (13)
<223> OTHER INFORMATION: n = 2'-O-methyluridine
<220> FEATURE:
<221> NAME/KEY: modified_base
<222> LOCATION: (14)
<223> OTHER INFORMATION: n = 2'-O-methyluridine
```

```
<220> FEATURE:
<221> NAME/KEY: modified_base
<222> LOCATION: (15)
<223> OTHER INFORMATION: n = 2'-O-methylcytidine
<220> FEATURE:
<221> NAME/KEY: modified_base
<222> LOCATION: (19)
<223> OTHER INFORMATION: n = deoxythymidine
<220> FEATURE:
<221> NAME/KEY: modified_base
<222> LOCATION: (20)
<223> OTHER INFORMATION: n = deoxythymidine

<400> SEQUENCE: 17
gnnnggagnn nannnggann                                          20
```